United States Patent
Sant et al.

(10) Patent No.: US 10,039,858 B2
(45) Date of Patent: Aug. 7, 2018

(54) BIODEGRADABLE POLY(ESTER AMIDE) ELASTOMERS AND USES THEREFOR

(71) Applicant: University of Pittsburgh—Of the Commonwealth System of Higher Education, Pittsburgh, PA (US)

(72) Inventors: Shilpa Sant, Pittsburgh, PA (US); Vinayak Sant, Pittsburgh, PA (US)

(73) Assignee: University of Pittsburgh—Of the Commonweatlh System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/227,187

(22) Filed: Aug. 3, 2016

(65) Prior Publication Data
US 2017/0035932 A1 Feb. 9, 2017

Related U.S. Application Data

(60) Provisional application No. 62/200,364, filed on Aug. 3, 2015.

(51) Int. Cl.
| | | |
|---|---|---|
| A61L 27/18 | (2006.01) | |
| A61F 2/24 | (2006.01) | |
| A61L 27/58 | (2006.01) | |
| C12N 5/00 | (2006.01) | |
| C08G 69/48 | (2006.01) | |
| A61L 27/54 | (2006.01) | |
| A61L 27/38 | (2006.01) | |

(52) U.S. Cl.
CPC ........... *A61L 27/18* (2013.01); *A61L 27/3804* (2013.01); *A61L 27/54* (2013.01); *C08G 69/48* (2013.01); *A61L 2300/102* (2013.01); *A61L 2300/624* (2013.01); *A61L 2430/20* (2013.01); *C08G 2230/00* (2013.01); *C12N 2533/30* (2013.01)

(58) Field of Classification Search
CPC ........... A61L 2300/624; A61L 2430/20; A61L 27/3804; A61L 27/54; C08L 71/02; C08G 2230/00; C12N 2533/30
See application file for complete search history.

(56) References Cited

U.S. PATENT DOCUMENTS

2007/0003753 A1\* 1/2007 Asgari ............... A61L 27/28
428/315.5

FOREIGN PATENT DOCUMENTS

WO 2007082305 A3 7/2007
WO 2008144514 A2 11/2008

OTHER PUBLICATIONS

Patel et al. (Biomaterials. May 2013; 34(16) 3970-3983).*
Cheng et al. (Adv. Mater. 2011, 23, H95-H100).*
Akhilesh et al.; "Anisotropic poly (glycerol sebacate)-poly (E-caprolactone) electrospun fibers promote endothelial cell guidance"; Biofabrication; 2015; pp. 1-11; vol. 7.
Allcock et al.; Contemporary Polymer Chemistry: Third Edition; 2003; pp. 1-15.
Amsden; "Curable, biodegradable elastomers: emerging biomaterials for drug delivery and tissue engineering"; Soft Matter; 2007; pp. 1335-1348; vol. 3.
Badrossamay et al.; "Engineering hybrid polymer-protein super-aligned nanofibers via rotary jet spinning"; Biomaterials; 2014; pp. 3188-3197; vol. 35.
Bae et al.; "Development of functional biomaterials with micro- and nanoscale technologies for tissue engineering and drug delivery applications"; J Tissue Eng Regen Med.; 2014; pp. 1-14; vol. 8:1.
Barakat et al.; "VEGF inhibitors for the treatment of neovascular age-related macular degeneration"; Expert Opin. Investig. Drugs; 2009; pp. 637-646; vol. 18:5.
Bat et al.; "Biodegradable elastomers for biomedical applications and regenerative medicine"; Regen. Med.; 2014; pp. 385-398; vol. 9:3.
Bettinger et al.; "Amino alcohol-based degradable poly(ester amide) elastomers"; Biomaterials; 2008; pp. 2315-2325; vol. 29:15.
Bettinger et al.; "In vitro and in vivo degradation of poly(1,3-diamino-2-hydroxypropane-co-polyol sebacate) elastomers"; J Biomed Mater Res; 2009; pp. 1077-1088; vol. 91A.
Bettinger; "Synthesis and microfabrication of biomaterials for soft-tissue engineering"; Pure Appl. Chem.; 2009; pp. 2183-2201; vol. 81:12.
Bhardwaj et al.; "Electrospinning: A fascinating fiber fabrication technique"; Biotechnology Advances; 2010; pp. 325-347; vol. 28.
Bian et al.; "tissue engineering of functional skeletal muscle: challenges and recent advances"; IEEE Eng Med Biol Mag.; 2008; pp. 109-113; vol. 27:5.
Bruggeman et al.; "Biodegradable Poly(polyol sebacate) Polymers"; Biomaterials; 2008; pp. 4726-4735; vol. 29:36.
Carey et al.; Advanced Organic Chemistry, Fifth Edition; Part A: Structure and Mechanisms; 2007; pp. 1-1210.
Carraher et al.; "Synthesis of Reactants and Intermediates for Polymers"; Carraher's Polymer Chemistry: Eight Edition; 2011; pp. 553-572.
Castiglione et al.; "Effect of Cross-Linking Properties on the Vibrational Dynamics of Cyclodextrins-Based Polymers: An Experimental-Numerical Study"; J. Phys. Chem. B; 2012; pp. 7952-7958; vol. 116.
Ceonzo et al.; "Polyglycolic acid induced inflammation: Role of hydrolysis and resulting complement activation1"; Tissue Eng.; 2006; pp. 301-308; vol. 12:2.
Chapman et al.; "Surveying for Surfaces that Resist the Adsorption of Proteins"; J. Am. Chem. Soc.; 2000; pp. 8303-8304; vol. 122.

(Continued)

*Primary Examiner* — Anna Falkowitz
(74) *Attorney, Agent, or Firm* — The Webb Law Firm

(57) ABSTRACT

Provided herein are biodegradable poly(ester amide) elastomers, methods of making the elastomers, and methods of using the elastomers, for example for tissue engineering. The elastomers can be used for preparation of tissue prostheses, such as a heart valve leaflet, a heart valve, cartilage, myocardium, blood vessels, smooth muscle, skeletal muscle, or other tissues. Also provided herein are semiquantitative FTIR methods for determining structure of a poly (ester amide) elastomer.

20 Claims, 37 Drawing Sheets
(9 of 37 Drawing Sheet(s) Filed in Color)

(56) References Cited

OTHER PUBLICATIONS

Chappelow et al.; "Neovascular Age-Related Macular Degeneration: Potential Therapies"; Drugs; 2008; pp. 1029-1036; vol. 68:8.
Chen et al.; "A comparative study on in vitro enzymatic degradation of poly(glycerol sebacate) and poly(xylitol sebacate)"; RSC Advances; 2012; pp. 4125-4134; vol. 2.
Chen et al.; "Characterisation of a soft elastomer poly(glycerol sebacate) designed to match the mechanical properties of myocardial tissue"; Biomaterials; 2008; pp. 47-57; vol. 29.
Chen et al.; "Elastomeric biomaterials for tissue engineering"; Progress in Polymer Science; 2013; pp. 584-671; vol. 38.
Cheung et al.; "Current Progress in Tissue Engineering of Heart Valves: Multiscale Problems, Multiscale Solutions"; Expert Opin Biol Ther.; 2015; pp. 1155-1172; vol. 15:8.
Courtney et al.; "Design and analysis of tissue engineering scaffolds that mimic soft tissue mechanical anisotropy"; Biomaterials; 2006; pp. 3631-3638; vol. 27.
De et al.; "Equilibrium Swelling and Kinetics of pH-Responsive Hydrogels: Models, Experiments, and Simulations"; Journal of Microelectromechanical Systems; 2002; pp. 544-555; vol. 11:5.
Deng et al.; "In vitro degradation and release profiles for poly-dl-lactide-poly(ethlyene glycol) microspheres containing human serum albumin"; Journal of Controlled Release; 2001; pp. 165-173; vol. 71.
Engelmayr, Jr. et al.; "Accordion-Like Honeycombs for Tissue Engineering of Cardiac Anisotropy"; Nat Mater.; 2008; pp. 1003-1010; vol. 7:12.
Eslami et al.; "Fiber-reinforced hydrogel scaffolds for heart valve tissue engineering"; Journal of Biomaterials Applications; 2014; pp. 399-410; vol. 29:3.
Flory; Principles of Polymer Chemistry; Cornell University Press; Ithaca, NY; 1953; pp. 1-687.
Fu et al.; "Electrospun gelatin/PCL and collagen/PLCL scaffolds for vascular tissue engineering"; International Journal of Nanomedicine; 2014; pp. 2335-2344; vol. 9.
Gaharwar et al.; "Anisotropic Poly (glycerol sebacate)-Poly (E-caprolactone) Electrospun Fibers Promote Endothelial Cell Guidance"; Biofabrication; 2016; pp. 1-19; vol. 7:1.
Gao et al.; "Poly(glycerol sebacate) supports the proliferation and phenotypic protein expression of primary baboon vascular cells"; J. Biomed Mater Res; 2007; pp. 1070-1075; vol. 83A.
Gooch; Encyclopedic Dictionary of Polymers; 2nd edition; Springer; New York; 2010; pp. 1-1008.
Hakuli et al.; "FT-IR in the Quantitative Analysis of Gaseous Hydrocarbon Mixtures"; Anal. Chem.; 1995; pp. 1881-1886; vol. 67.
Hasan et al.; "Biomechanical properties of native and tissue engineered heart valve constructs"; Journal of Biomechanics; 2014; pp. 1949-1963; vol. 47.
Holzapfel et al.; "Biomechanics of Soft Tissue in Cardiovascular Systems"; SpringerWien New York; 2003; pp. 1-27.
Huebsch et al.; "Inspiration and application in the evolution of biomaterials"; Nature; 2009; pp. 426-432; vol. 462:7272.
Jaafar et al.; "Improving fluorescence imaging of biological cells on biomedical polymers"; Acta Biomaterialia; 2011; pp. 1588-1598; vol. 7.
Jie et al.; "H-Nuclear magnetic resonance spectroscopic studies of saturated, acetylenic and ethylenic triacylglycerols"; Chemistry and Physics of Lipids; 1995; pp. 155-171; vol. 77.
Karrer et al.; "PPS-PEG surface coating to reduce thrombogenicity of small diameter ePTFE vascular grafts"; The International Journal of Artificial Organs; 2005; pp. 993-1002; vol. 28:10.
Khan et al.; "Advanced Materials for Co-Delivery of Drugs and Genes in Cancer Therapy"; Adv. Healthcare Mater.; 2012; pp. 373-392; vol. 1.
Kidane et al.; "A novel nanocomposite polymer for development of synthetic heart valve leaflets"; Acta Biomaterialia; 2009; pp. 2409-2417; vol. 5.
Kim et al.; "Emerging nanotechnology approaches in tissue engineering and regenerative medicine"; International Journal of Nanomedicine; 2014; pp. 1-5; vol. 9.
Knop et al.; "Poly(ethylene glycol) in Drug Delivery: Pros and Cons as Well as Potential Alternatives"; Angew. Chem. Int. Ed.; 2010; pp. 6288-6308; vol. 49.
Ko et al.; "Surface characterization and platelet adhesion studies of plasma-sulphonated polyethylene"; Biomaterials; 1993; pp. 657-664; vol. 14:9.
Korossis et al.; "Tissue Engineering of Cardiac Valve Prostheses II: Biomechanical Characterization of Decellularized Porcine Aortic Heart Valves"; The Journal of Heart Valve Disease; 2002; pp. 463-471; vol. 11.
Langer et al.; "Designing materials for biology and medicine"; Nature; 2004; pp. 487-492; vol. 428.
Lee et al.; "Biodegradable elastomer for soft tissue engineering"; European Polymer Journal; 2009; pp. 3249-3256; vol. 45.
Li et al.; "Biodegradable soft elastomers: synthesis/properties of materials and fabrication of scaffolds"; RSC Advances; 2012; pp. 8229-8242; vol. 2.
Li; "Synthesis, Characterization and Properties of Vinyl Ester Matrix Resins"; Dissertation submitted to the Faculty of the Virginia Polytechnic Institute and State University; 1998.
Zhou et al.; "Biodegradable poly(E-caprolactone)-poly(ethylene glycol) block copolymers: characterization and their use as drug carriers for a controlled delivery system"; Biomaterials; 2003; pp. 3563-3570; vol. 24.
Zhu et al.; "Preparation, Characterization, and Properties of Polylactide (PLA)—Poly(ethylene Glycol) (PEG) Copolymers: A Potential Drug Carrier"; Journal of Applied Polymer Science; 1990; pp. 1-9; vol. 39.
Li et al.; "Succinic Acid Based Biodegradable Thermoplastic Poly-(ester urethane) Elastomers: Effects of Segment Ratios and Lengths on Physical Properties"; Ind. Eng. Chem. Res.; 2014; pp. 1404-1414; vol. 53.
Liu et al.; "Functionalized Synthetic Biodegradable Polymer Scaffolds for Tissue Engineering"; Macromol. Biosci.; 2012; pp. 911-919; vol. 12.
Liu et al.; "Synthesis, preparation, in vitro degradation, and application of novel degradable bioelastomers—A review"; Progress in Polymer Science; 2012; pp. 715-765; vol. 37.
Lyu et al.; "Degradability of Polymers for Implantable Biomedical Devices"; Int. J. Mol. Sci.; 2009; pp. 4033-4065; vol. 10.
Makadia et al.; "Poly Lactic-co-Glycolic Acid (PLGA) as Biodegradable Controlled Drug Delivery Carrier"; Polymers (Basel).; 2011; pp. 1377-1397; vol. 3:3.
Martina et al.; "Biodegradable polymers applied in tissue engineering research: a review"; Polym. Int.; 2007; pp. 145-157; vol. 56.
Masoumi et al.; "Electrospun PGS: PCL Microfibers Align Human Valvular Interstitial Cells and Provide Tunable Scaffold Anisotropy"; Adv Healthc Mater; 2014; pp. 929-939; vol. 3:6.
Mendelson et al.; "Heart Valve Tissue Engineering: Concepts, Approaches, Progress, and Challenges"; Annals of Biomedical Engineering; 2006; pp. 1799-1819; vol. 34:12.
Mukundan et al.; "Nanofibrous composite scaffolds of poly(ester amides) with tunable physicochemical and degradation properties"; European Polymer Journal; 2015; pp. 21-35; vol. 68.
Muller et al.; "Rubber and Rubber Balloons: Paradigms of Thermodyanics"; Springer; New York; 2004; pp. 20-34.
Nagura et al.; "Anti-Thrombogenicity of Styrene-Butadiene-Styrene Triblock Copolymer Grafted with Poly(ethylene glycol)s"; J Appl Polym Sci; 2009; pp. 2462-2476; vol. 113.
Nair et al.; "Biodegradable polymers as biomaterials"; Prog Polym Sci; 2007; pp. 762-798; vol. 32.
Nijst et al.; "Synthesis and Characterization of Photocurable Elastomers from Poly(glycerol-co-sebacate)"; Biomacromolecules; 2007; pp. 3067-3073; vol. 8:10.
Pandey et al.; "FTIR Spectroscopy: A Tool for Quantitative Analysis of Ciprofloxacin in Tablets"; Indian J Pharm Sci.; 2012; pp. 86-90; vol. 74:1.
Parry et al.; "A comparison of the size distribution of collagen fibrils in connective tissues as a function of age and a possible relation

(56) References Cited

OTHER PUBLICATIONS between fibril size distribution and mechanical properties"; Proc. R. Soc. Lond. B.; 1978; pp. 305-321; vol. 203.
Pascault et al.; "Thermosetting Polymers"; Marcel Dekkers, Inc.; New York; 2002; pp. 1-28.
Patel et al.; "Highly elastomeric poly(glycerol sebacate)-co-poly-(ethylene glycol) amphiphilic block copolymers"; Biomaterials; 2013; pp. 3970-3983; vol. 34:16.
Pelipenko et al.; "Critical attributes of nanofibers: Preparation, drug loading, and tissue regeneration"; International Journal of Pharmaceutics; 2015; pp. 57-74; vol. 484.
Pielichowski et al.; "Differential Scanning Calorimetry Studies on Poly(ethylene Glycol) with Different Molecular Weights for Thermal Energy Storage Materials"; Polym. Adv. Technol.; 2002; pp. 690-696; vol. 13.
Place et al.; "Complexity in biomaterials for tissue engineering"; Nature Materials; 2009; pp. 457-470; vol. 8.
Rai et al.; "Synthesis, properties and biomedical applications of poly(glycerol sebacate) (PGS): A review"; Progress in Polymer Science; 2012; pp. 1051-1078; vol. 37.
Rudin; The Element of Polymer Science and Engineering: Second Edition; Academic Press; New York; 1999; pp. 373-443.
Sant et al.; "Biomimetic Gradient Hydrogels for Tissue Engineering"; Can J Chem Eng; 2010; pp. 899-911; vol. 88:6.
Sant et al.; "Effect of biodegradation and de novo matrix synthesis on the mechanical properties of VIC-seeded PGS-PCL scaffolds"; Acta Biomater; 2013; pp. 5963-5973; vol. 9:4.
Sant et al.; "Effect of polymer architecture on surface properties, plasma protein adsorption, and cellular interactions of pegylated nanoparticles"; J Biomed Mater Res; 2008; pp. 885-895; vol. 87A.
Sant et al.; "Effect of porosity on the release kinetics of propafenone-loaded PEG-g-PLA nanoparticles"; Journal of Controlled Release; 2005; pp. 203-214; vol. 107.
Sant et al.; "Hybrid PGS-PCL Microfibrous Scaffolds with Improved Mechanical and Biological Properties"; J Tissue Eng Regen Med; 2011; pp. 283-291; vol. 5:4.
Sant et al.; "Microporous Structure and Drug Release Kinetics of Polymeric Nanoparticles"; Langmuir; 2008; pp. 280-287; vol. 24.
Shameli et al.; "Synthesis and Characterization of Polyethylene Glycol Mediated Silver Nanoparticles by the Green Method"; Int. J. Mol. Sci.; 2012; pp. 6639-6650; vol. 13.
Shaw et al.; Introduction to Polymer Viscoelasticity: Third Edition; 2005; John Wiley & Sons, Inc.; pp. 1-327.
Shi et al.; "Recent Advances in Synthetic Bioelastomers"; Int. J. Mol. Sci.; 2009; pp. 4223-4256; vol. 10.
Shih et al.; "Synthesis and Evaluation of Poly(hexamethylene-urethane) and PEG-Poly(hexamethylene-urethane) and Their Cholesteryl Oleyl Carbonate Composites for Human Blood Biocompatibility"; Molecules; 2011; pp. 8181-8197; vol. 16.
Sohier et al.; "The potential of anisotropic matrices as substrate for heart valve engineering"; Biomaterials; 2014; pp. 1833-1844; vol. 35.
Soliman et al.; "Controlling the porosity of fibrous scaffolds by modulating the fiber diameter and packing density"; J Biomed Mater Res Part A; 2011; pp. 566-574; vol. 96A.
Storey et al.; "Degradable polyurethane networks based on D,L-lactide, glycolide, E-caprolactone, and trimethylene carbonate homopolyester and copolyester triols"; Polymer; 1994; pp. 830-838; vol. 35:4.
Stuckey et al.; "Magnetic Resonance Imaging Evaluation of Remodeling by Cardiac Elastomeric Tissue Scaffold Biomaterials in a Rat Model of Myocardial Infarction"; Tissue Engineering: Part A; pp. 3395-3402; vol. 16:11.
Sun et al.; "The influence of lactic on the properties of Poly (glycerol-sebacate-lactic acid)"; Materials Science and Engineering C; 2009; pp. 178-182; vol. 29.
Suyatma et al.; "Effects of Hydrophilic Plasticizers on Mechanical, Thermal, and Surface Properties of Chitosan Films"; J. Agric. Food Chem.; 2005; pp. 3950-3957; vol. 53.
Tong et al.; "Controlling the Fibroblastic Differentiation of Mesenchymal Stem Cells Via the Combination of Fibrous Scaffolds and Connective Tissue Growth Factor"; Tissue Engineering: Part A; 2011; pp. 2773-2785; vol. 17:21/22.
Trotta et al.; "Synthesis and characterization of a hyper-branched water-soluble B-cyclodextrin polymer"; Beilstein J. Org. Chem.; 2014; pp. 2586-2593; vol. 10.
Tseng et al.; "Anisotropic Poly(Ethylene Glycol)/Polycaprolactone Hydrogel-Fiber Composites for Heart Valve Tissue Engineering"; Tissue Engineering: Part A; 2014; pp. 2634-2645; vol. 20:19/20.
Ubaghs et al.; "Synthesis and characterization of alternating poly(amide urea)s and poly(amide urethane urethane)s from E-caprolactam, diamines, and diphenyl carbonate or ethylene carbonate"; e-Polymers; 2003; pp. 1-16; vol. 068.
Wang et al.; "A tough biodegradable elastomer"; Nature Biotechnology; 2002; pp. 602-606; vol. 20.
Wang et al.; "Biodegradable microfluidic scaffolds for tissue engineering from amino alcohol-based poly(ester amide) elastomers"; Organogenesis; 2010; pp. 212-216; vol. 6:4.
Wang et al.; "Fully Biodegradable Airway Stents Using Amino Alcohol-Based Poly(ester amide) Elastomers"; Adv Healthc Mater; 2013; pp. 1329-1336; vol. 2:10.
Wang et al.; "In vivo degradation characteristics of poly(glycerol sebacate)"; J Biomed Mater Res; 2003; pp. 192-197; vol. 66A.
Xu et al.; "Mechanically tissue-like elastomeric polymers and their potential as a vehicle to deliver functional cardiomyocytes"; Journal of the Mechanical Behavior of Biomedical Materials; 2013; pp. 354-365; vol. 28.
Xue et al.; "PEGylated poly(ester amide) elastomers with tunable physico-chemical, mechanical and degradation properties"; European Polymer Journal; 2015; pp. 163-179; vol. 72.
Xue et al.; "Semiquantitative FTIR Analysis of the Crosslinking Density of Poly(ester amide)-Based Thermoset Elastomers"; Macromol. Mater. Eng.; 2016; pp. 296-305; vol. 301.
Yang et al.; "Novel Citric Acid-Based Biodegradable Elastomers for Tissue Engineering"; Adv. Mater.; 2004; pp. 511-516; vol. 16:6.

* cited by examiner (a)

| APS | Elastic Modulus (MPa) | Crosslinking Density (N, mol m$^{-3}$) | RSD of N (%) | Amide I: carbonyl (ratio 1) | RSD of ratio 1 (%) | Amide II: carbonyl (ratio 2) | RSD of ratio 2 (%) |
|---|---|---|---|---|---|---|---|
| 12 h | 2.12 | 285.7 | 21.1 | 1.05 | 2.1 | 1.07 | 2.5 |
| 24 h | 3.25 | 438.0 | 15.6 | 0.75 | 1.9 | 0.78 | 2.1 |
| 48 h | 4.24 | 570.7 | 17.7 | 0.69 | 2.4 | 0.73 | 3 |
| 72 h | 4.55 | 612.5 | 23.9 | 0.65 | 2.3 | 0.70 | 3.4 |

RSD: relative standard deviation

|  | Ratio 1 | Ratio 2 |
|---|---|---|
| Number of XY Pairs | 4 | 4 |
| Pearson r | -0.9517 | -0.9439 |
| R squared | 0.9058 | 0.8910 |
| P value (two-tailed) | 0.0483 | 0.0561 |

● Amide I:Carbonyl (Ratio 1)
■ Amide II:Carbonyl (Ratio 2)

| (b) APS-10PEG 1K | Elastic Modulus (MPa) | Crosslinking Density (N, mol m⁻³) | RSD of N (%) | Amide I: carbonyl (ratio 1) | RSD of ratio 1 (%) | Amide II: carbonyl (ratio 2) | RSD of ratio 2 (%) |
|---|---|---|---|---|---|---|---|
| 12 h | 0.43 | 57.9 | 12.1 | 0.80 | 1.3 | 0.96 | 2.4 |
| 24 h | 1.23 | 165.8 | 13.3 | 0.61 | 2.5 | 0.73 | 3.5 |
| 48 h | 1.88 | 253.4 | 23.5 | 0.52 | 2.1 | 0.66 | 4.1 |
| 72 h | 2.78 | 374.7 | 19.7 | 0.46 | 1.4 | 0.39 | 2.3 |

RSD: relative standard deviation

|  | Ratio 1 | Ratio 2 |
|---|---|---|
| Number of XY Pairs | 4 | 4 |
| Pearson r | -0.9598 | -0.9889 |
| R squared | 0.9211 | 0.9780 |
| P value (two-tailed) | 0.0402 | 0.0111 |

(a)

(b)

(c)

| Polymer Scaffold | $T_g$ (°C) | $T_c$ (°C) | $\Delta H_c$ (Jg⁻¹) | $T_m$ (°C) | $\Delta H_m$ (Jg⁻¹) |
|---|---|---|---|---|---|
| PCL | NA | 30.6 | 50.0 | 55.6 | 58.4 |
| APS/PCL | -1.4 | 32.7 | 11.6 | 56.9 | 15.3 |
| APS-15PEG/PCL | -14.5 | 32.1 | 26.5 | 56.1 | 23.7 |
| APS-25PEG/PCL | -16.4 | 30.8 | 31.7 | 56.2 | 29.4 |
| APS-40PEG/PCL | -23.9 | 29.9 | 38.3 | 57.7 | 34.6 |

(a)

(b)

SEQUENCE LISTING

```
<160> NUMBER OF SEQ ID NOS: 21

<210> SEQ ID NO 1
<211> LENGTH: 5
<212> TYPE: PRT
<213> ORGANISM: Homo sapiens

<400> SEQUENCE: 1

Ile Lys Leu Leu Ile
1               5

<210> SEQ ID NO 2
<211> LENGTH: 4
<212> TYPE: PRT
<213> ORGANISM: Homo sapiens

<400> SEQUENCE: 2

Arg Glu Asp Val
1

<210> SEQ ID NO 3
<211> LENGTH: 5
<212> TYPE: PRT
<213> ORGANISM: Homo sapiens

<400> SEQUENCE: 3

Arg Gly Asp Ser Pro
1               5

<210> SEQ ID NO 4
<211> LENGTH: 4
<212> TYPE: PRT
<213> ORGANISM: Homo sapiens
```

```
<400> SEQUENCE: 4

Arg Gly Asp Val
1

<210> SEQ ID NO 5
<211> LENGTH: 5
<212> TYPE: PRT
<213> ORGANISM: Homo sapiens

<400> SEQUENCE: 5

Leu Arg Gly Asp Asn
1               5

<210> SEQ ID NO 6
<211> LENGTH: 4
<212> TYPE: PRT
<213> ORGANISM: Homo sapiens

<400> SEQUENCE: 6

Arg Gly Asp Thr
1

<210> SEQ ID NO 7
<211> LENGTH: 5
<212> TYPE: PRT
<213> ORGANISM: Homo sapiens

<400> SEQUENCE: 7

Tyr Ile Gly Ser Arg
1               5

<210> SEQ ID NO 8
<211> LENGTH: 6
<212> TYPE: PRT
<213> ORGANISM: Homo sapiens

<400> SEQUENCE: 8

Thr Thr Ser Trp Ser Gln
1               5

<210> SEQ ID NO 9
<211> LENGTH: 8
<212> TYPE: PRT
<213> ORGANISM: Homo sapiens

<400> SEQUENCE: 9

Ala Glu Ile Asp Gly Ile Glu Leu
1               5

<210> SEQ ID NO 10
<211> LENGTH: 6
<212> TYPE: PRT
<213> ORGANISM: Homo sapiens

<400> SEQUENCE: 10

Trp Tyr Arg Gly Arg Leu
1               5

<210> SEQ ID NO 11
<211> LENGTH: 7
<212> TYPE: PRT
<213> ORGANISM: Homo sapiens

<400> SEQUENCE: 11
```

```
Ser Ile Lys Val Ala Val Ser
1               5

<210> SEQ ID NO 12
<211> LENGTH: 5
<212> TYPE: PRT
<213> ORGANISM: Homo sapiens

<400> SEQUENCE: 12

Pro Asp Ser Gly Arg
1               5

<210> SEQ ID NO 13
<211> LENGTH: 10
<212> TYPE: PRT
<213> ORGANISM: Homo sapiens

<400> SEQUENCE: 13

Arg Asn Ile Ala Glu Ile Ile Lys Asp Ile
1               5                   10

<210> SEQ ID NO 14
<211> LENGTH: 4
<212> TYPE: PRT
<213> ORGANISM: Homo sapiens

<400> SEQUENCE: 14

Asp Gly Glu Ala
1

<210> SEQ ID NO 15
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Val Thr Xaa Gly
1

<210> SEQ ID NO 16
<211> LENGTH: 6
<212> TYPE: PRT
<213> ORGANISM: Homo sapiens

<400> SEQUENCE: 16

Pro Arg Arg Ala Arg Val
1               5

<210> SEQ ID NO 17
<211> LENGTH: 19
<212> TYPE: PRT
<213> ORGANISM: Homo sapiens

<400> SEQUENCE: 17

Tyr Glu Lys Pro Gly Ser Pro Pro Arg Glu Val Val Pro Arg Pro
1               5                   10                  15

Pro Gly Val

<210> SEQ ID NO 18
<211> LENGTH: 28
```

```
<212> TYPE: PRT
<213> ORGANISM: Homo sapiens

<400> SEQUENCE: 18

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 19
<211> LENGTH: 17
<212> TYPE: PRT
<213> ORGANISM: Homo sapiens

<400> SEQUENCE: 19

Arg Ile Gln Asn Leu Leu Lys Ile Thr Asn Leu Arg Ile Lys Phe Val
1               5                   10                  15

Lys

<210> SEQ ID NO 20
<211> LENGTH: 5
<212> TYPE: PRT
<213> ORGANISM: Homo sapiens

<400> SEQUENCE: 20

Ile Lys Val Ala Val
1               5

<210> SEQ ID NO 21
<211> LENGTH: 6
<212> TYPE: PRT
<213> ORGANISM: Homo sapiens

<400> SEQUENCE: 21

Ile Lys Val Ala Val Ser
1               5
```

BIODEGRADABLE POLY(ESTER AMIDE) ELASTOMERS AND USES THEREFOR

CROSS REFERENCE TO RELATED APPLICATIONS

This application claims the benefit of Unites States Provisional Patent Application No. 62/200,364, Filed Aug. 3, 2015, which is incorporated herein by reference in its entirety.

The Sequence Listing associated with this application is filed in electronic format via EFS-Web and is hereby incorporated by reference into the specification in its entirety. The name of the text file containing the Sequence Listing is 6527_1603011_ST25.txt. The size of the text file is 3,399 bytes, and the text file was created on Aug. 2, 2016.

Provided herein are novel biodegradable poly(ester amide) elastomers and methods of making and using those elastomers.

Biomaterials used for tissue engineering should provide structural integrity and support within a mechanically dynamic in vivo environment without significant adverse effect. Consequently, there is a need and interest in developing biodegradable elastomers which exhibit mechanical properties similar to those of soft tissue and degradation rates similar to the tissue regeneration. Synthetic biodegradable elastomers are promising candidates for tissue engineering because their physical, chemical, mechanical and degradation properties can be tailored by the rational design of the elastomer structures.

One goal of tissue engineering is to fabricate extracellular matrix (ECM)-mimetic biomaterial scaffolds that can provide initial structural support and guidance to the seeded or recruited cells and allow for diffusion of nutrients and waste through the porous matrix. Through appropriate biochemical and/or biomechanical guidance cues, cells can migrate, proliferate and differentiate in the scaffold and eventually, degrade the scaffold matrix and replace it with de novo synthesized ECM. In addition to the scaffold architecture, another important design principle for tissue engineering scaffolds is to create mechanically analogous tissue substitutes. Specifically, for soft tissues such as skeletal muscle and heart valves, biodegradable synthetic elastomers are considered to be one of the most promising materials because of their outstanding mechanical compliance and the ability to withstand cyclic mechanical loading without early structural failure. Moreover, synthetic elastomers offer many advantages over natural polymers such as facile production with less batch-to-batch variation and less immunogenicity.

There is a growing interest in developing novel biocompatible and biodegradable materials for multiple biomedical applications such as tissue engineering and drug delivery. For successful regeneration of soft and mechanically demanding tissues like heart valves and myocardium, it is important that tissue engineered scaffolds 1) are biodegradable and promote cell growth and tissue regeneration; 2) have tunable mechanical and degradation properties to match the regeneration/healing rate of the target tissue; and 3) endure the dynamic in vivo microenvironment and mechanically mimic the native extracellular matrix (ECM) to maintain tissue integrity. Biodegradable synthetic elastomers stand out as one of the most promising materials for soft tissue engineering because of their tunable mechanical compliance, biodegradation rates and excellent biocompatibility. Previous research has focused on thermoplastic polymer/elastomers such as polyurethanes (PU), poly (lactic acid) (PLA), poly (glycolic acid) (PGA), poly (ε-caprolactone) (PCL) and their block copolymers. Although crystalline segments in the structures of these thermoplastic elastomers provide mechanical strength, they resist degradation. Therefore, these materials suffer from heterogeneous degradation profiles and demonstrate non-linear loss of mechanical strength during degradation. Such degradation profile is usually not preferred in tissue engineering applications because it may lead to sudden mechanical failure of the scaffold before substantial degradation and tissue regeneration.

Recent years witnessed significant advances in the development of biodegradable thermoset elastomers. Poly (glycerol sebacate) (PGS) is a benchmark polymer in this class and has been extensively studied for its synthesis and fabrication, biocompatibility, degradation, and tissue engineering applications. Rapid in vivo degradation rates of PGS limits its potential use for applications in regeneration of tissues that regenerate slowly. To circumvent this limitation, poly (1,3-diamino-2-hydroxypropane-co-polyol sebacate) (APS) elastomers were synthesized by incorporating amide bonds in the PGS backbone to reduce the in vivo degradation rate. APS elastomers possess tunable degradability and mechanical properties, as well as excellent in vitro and in vivo biocompatibility. Airway stents made from APS via microfabrication method have shown good biocompatibility. However, due to their poor solubility in common organic/aqueous solvents, APS elastomers are amenable only to few fabrication methods, such as thermally cured films or microfabrication. Moreover, the poor solubility of APS pre-polymer restricts further chemical modification to fine-tune the physicochemical properties. Importantly, altering the selection of polyols, monomer ratio, and curing conditions of APS elastomers has provided a relatively narrow range of elastic modulus (0.56-4.34 MPa) and tensile strength (0.24-1.69 MPa). Thus, it is worthwhile to broaden the spectrum of physicochemical, mechanical, and degradation properties of APS by chemical modification.

However, current elastomers are limited in number and property spectrum. In addition, some of those elastomers such as APS has undesired physicochemical properties. Therefore, there is still a strong need in the field to widely tune the chemical, physical, mechanical, degradation and biological properties for their wider use in bioengineering.

SUMMARY

Provided herein are polyethylene glycol (PEG)-modified, biodegradable poly(ester amide) elastomers and methods of making and using those elastomers. This class of elastomers possesses a wide range of mechanical properties that can be carefully tuned to suit the desired application by tuning curing time, PEG content, and monomer feed ratio. Compared to available thermoset elastomers such as PGS and APS, whose mechanical properties can also be tuned, the mechanical property (ultimate tensile strength, elastic modulus and elongation) of this series of novel elastomers can be lower or higher than those of the benchmark elastomers. This class of elastomers also is more hydrophilic and has a higher water uptake level than the benchmark thermoset elastomers. The degradation rates of this class of elastomers are widely tuned by PEG content. They can exhibit higher or lower in vitro degradation rates via surface erosion mechanism. This class of elastomers demonstrates comparable mechanical properties before and after degradation, which is not often seen in other elastomers. This significantly expands the palette of compositions useful in tissue engineering.

In one aspect, a polymer composition is provided comprising a copolymer comprising residues of a poly ($C_2$-$C_4$) alkylene glycol (e.g., [($CH_2$)$_2$—O]—, [($CH_2$)$_3$—O]—, [$CH_2$—$CH(CH_3)$—O]—, [($CH_2$)$_4$—O]—, [$CH(CH_3)$—$CH_2$—$CH_2$—O]—, [$CH(CH_3)$—$CH(CH_3)$—O]—, [$C(CH_3)_2$—$CH_2$—O]—), such as PEG, a $C_8$-$C_{12}$ aliphatic dicarboxylic acid (e.g., —C(O)—($CH_2$)$_{6-10}$—C(O)—), an aliphatic $C_3$-$C_7$ polyol with at least 3 hydroxyl groups, such as glycerol, and 1,3-diamino-2-hydroxy-propane. A medical device or prosthesis, comprising the polymer is provided, such as a heart valve leaflet, a heart valve, cartilage, myocardium, blood vessels, smooth muscle, skeletal muscle, or other tissues, and which optionally comprises anisotropic fibers of the polymer composition.

According to another aspect, a method of preparing a biocompatible elastomer copolymer is provided, comprising: condensing in a reaction mixture a C8-C12 aliphatic dicarboxylic acid (e.g., —C(O)—(CH2)6-10-C(O)—) with a poly(C2-C4 alkylene glycol) to produce a first product; and adding an aliphatic C3-C7 polyol with at least 3 hydroxyl groups and 1,3-diamino-2-hydroxy-propane to the reaction mixture and condensing the first product with the glycerol and 1,3-diamino-2-hydroxy-propane (DAHP) to produce the elastomer.

According to another aspect, a method of culturing cells is provided, comprising placing a composition of any of claims 1-9 in a suitable cell growth medium; contacting cells with the composition; and culturing cells under conditions suitable for cell growth.

In another aspect, a method of determining either the crosslinking density or relative quantities of amide or ester bonds in a polymer composition comprising one or both of amide and ester bonds is provided, comprising preparing the polymer composition, performing a semiquantitative FTIR assay on a sample of the polymer composition that determines carbonyl bond and amide bond peaks and optionally a pre-polymer or pre-crosslinking sample of the polymer, calculating a ratio of amide bonds to carbonyl bonds in the sample based on the semiquantitative FTIR assay, producing an output based on the semiquantitative FTIR assay, wherein the calculating and producing an output step are optionally computer-implemented, and the output is optionally stored on a non-transitory data medium.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
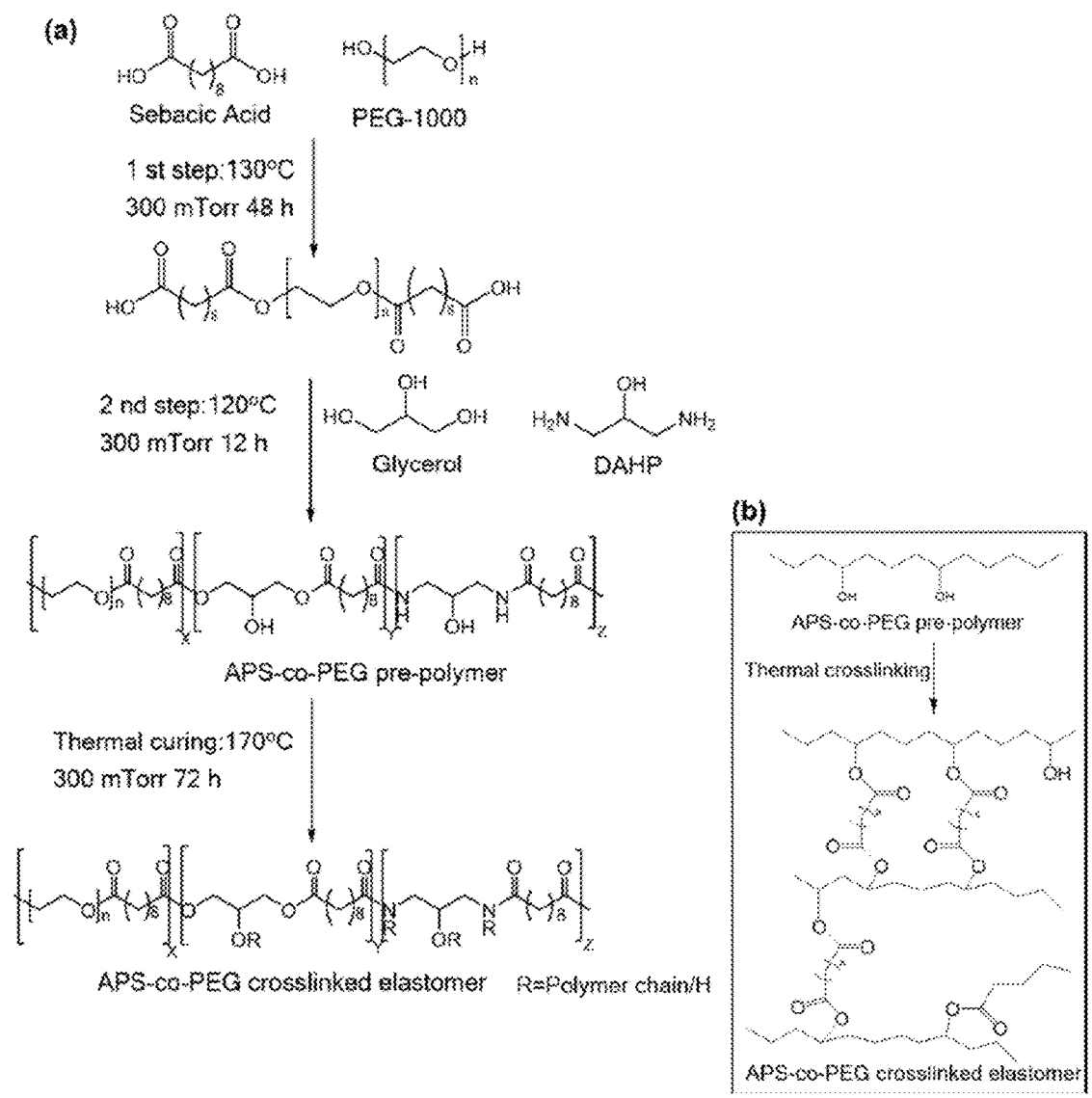
FIG. 1. The synthesis scheme of APS-co-PEG elastomers. Nomenclature of APS-co-PEG: APS-xPEGy, where "x" represents the PEG/sebacic acid molar percentage (15%, 25%, 40%) and "y" represents the PEG molecular weight (400 Da, 1 kDa, 2 kDa, 4 kDa). The molar ratio between DAHP and glycerol is kept constant at 2:1.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

By "bio compatible", it is meant that a device, scaffold composition, etc. is essentially, practically (for its intended use) and/or substantially non-toxic, non-injurous or non-inhibiting or non-inhibitory to cells, tissues, organs, and/or organ systems that would come into contact with the device, scaffold, composition, etc.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

The term "alkyl" refers to both branched and straight-chain saturated aliphatic hydrocarbon groups. These groups can have a stated number of carbon atoms, expressed as Cx-y, where x and y typically are integers. For example, $C_{5-10}$, includes $C_5$, $C_6$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. Aromatic groups include one or more benzene rings. As used herein, "halo" or "halogen" refers to fluoro, chloro, bromo, and iodo. An amine is a group having the structure —N(R1)(R2). Where R1 and R2 are H, the group is amino.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or are removed in the polymerization process. A polymer is said to comprise a specific type of linkage if that linkage is present in the polymer. An incorporated monomer is a "residue", thus, in the context of the described copolymer, sebacic acid (HO—(O)C—$(CH_2)_8$—C(O)—OH) is a monomer, while a residue of sebacic acid omits, e.g., the terminal hydroxyl groups (e.g., —C(O)—$(CH_2)_8$—C(O)—, as shown in Scheme 1), which are removed during condensation.

The polymers described herein are said to be bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzymatic cleavage. The polymers described herein contain labile ester linkages. The polymer or polymers may be selected so that it degrades over a time period. Non-limiting examples of useful in situ degradation rates include between 12 hours and 5 years, and increments of hours, days, weeks, months or years there between. For example, in the context of a drug product, the polymer may preferably degrade over 1, 2, 3, 4, 5, 6, 7, 8, 9, 10, 11, or 12 months, or longer, for example losing at least 75%, or 75-80%, of its weight at 37 degrees or at least 60%, or 60-70% of its weight at 14 days in vivo or in vitro, e.g. in PBS.

There is a growing interest in developing novel biocompatible and biodegradable materials for multiple biomedical applications such as tissue engineering and drug delivery. For successful regeneration of soft and mechanically demanding tissues like heart valves and myocardium, it is important that tissue engineered scaffolds 1) are biodegradable and promote cell growth and tissue regeneration; 2) have tunable mechanical and degradation properties to match the regeneration/healing rate of the target tissue; and 3) endure the dynamic in vivo microenvironment and mechanically mimic the native extracellular matrix (ECM) to maintain tissue integrity. Biodegradable synthetic elastomers stand out as one of the most promising materials for soft tissue engineering because of their tunable mechanical compliance, biodegradation rates and excellent biocompatibility. Previous research has focused on thermoplastic polymer/elastomers such as polyurethanes (PU), poly (lactic acid) (PLA), poly (glycolic acid) (PGA), poly (ε-caprolactone) (PCL) and their block copolymers. Although crystalline segments in the structures of these thermoplastic elastomers provide mechanical strength, they resist degradation. Therefore, these materials suffer from heterogeneous degradation profiles and demonstrate non-linear loss of mechanical strength during degradation. Such degradation profile is usually not preferred in tissue engineering applications because it may lead to sudden mechanical failure of the scaffold before substantial degradation and tissue regeneration.

Recent years witnessed significant advances in the development of biodegradable thermoset elastomers. Poly (glycerol sebacate) (PGS) is a benchmark polymer in this class and has been extensively studied for its synthesis and fabrication, biocompatibility, degradation, and tissue engineering applications. Rapid in vivo degradation rates of PGS limits its potential use for applications in regeneration of tissues that regenerate slowly. To circumvent this limitation, poly (1,3-diamino-2-hydroxypropane-co-polyol sebacate) (APS) elastomers were synthesized by incorporating amide bonds in the PGS backbone to reduce the in vivo degradation rate. APS elastomers possess tunable degradability and mechanical properties, as well as excellent in vitro and in vivo biocompatibility. Airway stents made from APS via microfabrication method have shown good biocompatibility. However, due to their poor solubility in common organic/aqueous solvents, APS elastomers are amenable only to few fabrication methods, such as thermally cured films or microfabrication. Moreover, the poor solubility of APS pre-polymer restricts further chemical modification to fine-tune the physicochemical properties. Importantly, altering the selection of polyols, monomer ratio, and curing conditions of APS elastomers has provided a relatively narrow range of elastic modulus (0.56-4.34 MPa) and tensile strength (0.24-1.69 MPa)[4]. Thus, it is worthwhile to broaden the spectrum of physicochemical, mechanical, and degradation properties of APS by chemical modification.

Polyethylene glycol (PEG) is an FDA approved biocompatible amphiphilic polyether that has been widely applied in drug delivery and implantation. PEG incorporation will enable the fine tuning of physicochemical, mechanical, and degradation properties to broaden the properties spectrum of APS elastomers. The pre-polymers of proposed elastomers are synthesized via one-pot two steps condensation polymerization. According to one example, the first step is the polycondensation between an alkanedioic acid (dicarboxylic acid), such as a $C_8$-$C_{12}$ aliphatic dicarboxylic acid and poly(ethylene glycol) (PEG) or another poly(oxyalkylene), such as a poly($C_2$-$C_4$ alkylene glycol). The mixture is charged in a round bottom flask and heated at 130° C. under Argon atmosphere for 2 h and under vacuum of 300 mTorr for 48 h. The product of the first step reaction is used without further purification. In the second step, a specific amount of polyol and/or polyamine is added into the round bottom flask and mixed thoroughly with the reactant. The reaction was stirred at 120° C. under Argon atmosphere and then further under reduced pressure of 300 mTorr for 12 h. The pre-polymer products are thermally crosslinked at 170° C. in vacuum for various periods of time. The resulting polymer films won't flow upon heating and are insoluble in water, indicating successful crosslinking.

The synthesis of the polymer compositions as described herein requires affordable starting materials and the synthesis process is unsophisticated and easy to scale up. The pre-polymers of proposed elastomers exhibit good solubility in common solvents which is due to the hydrophilicity of PEG. This property enables their chemical characterization by NMR spectroscopy and GPC by using commonly used solvents and potentially increased the processability of the polymers. The chemical composition of the polymer is biocompatible. The synthesis process requires no solvents or catalysts and each monomer is non-toxic, which ensures that as prepared polymers and the degradation products have minimal adverse effect.

Two prominent problems previously seen in tissue engineering are that 1) the materials cannot provide the suitable mechanical cues to the cells during regeneration and 2) have improper degradation rates which impede the regeneration process. The incorporation of PEG, or another poly($C_2$-$C_4$ alkylene glycol) incorporation to the structure backbones of benchmark thermoset elastomers largely broadens the mechanical properties and degradation rates of currently available elastomers, which are two key factors determining the application of certain elastomers. Broadening these two property spectrum enables the potential application of biodegradable elastomers for a variety of soft tissues including but not limited to cartilage, myocardium, heart valve leaflet, blood vessels, and smooth muscles. Importantly, this class of elastomers shows steady degradation rates and maintained mechanical properties after degradation, which means that the desired mechanical cues can be consistently delivered. This is distinctive to thermoplastic materials widely used currently whose mechanical properties are largely differed in dry, wet and degraded status.

APS elastomers are reported to have poor pre-polymer solubility in common solvents which limited its processability and potential chemical modification. PEG segments increase the poor pre-polymer solubility and therefore this class of elastomers can be processed by classical fabrication methods such as salt leaching and can be further developed into photo-crosslinkable materials to realize drug/cell delivery.

This class of elastomers possesses a wider range of mechanical properties that could be carefully tuned to suit the desired application. PEG segments increase the poor APS pre-polymer solubility and therefore this class of elastomers can be processed by classical fabrication methods, such as, without limitation by electrospinning or thermally-induced phase separation.

According to one aspect, a polymer composition is provided, comprising a copolymer comprising residues of a poly ($C_2$-$C_4$)alkylene glycol (e.g., [($CH_2$)$_2$—O]—, [($CH_2$)$_3$—O]—, [$CH_2$—CH($CH_3$)—O]—, [($CH_2$)$_4$—O]—, [CH($CH_3$)—$CH_2$—$CH_2$—O]—, [CH($CH_3$)—CH($CH_3$)—O]—, [C($CH_3$)$_2$—$CH_2$—O]—), a $C_8$-$C_{12}$ aliphatic dicarboxylic acid (e.g., —C(O)—($CH_2$)$_{6-10}$—C(O)—), an aliphatic $C_3$-$C_7$ polyol with at least 3 hydroxyl groups, such as glycerol and 1,3-diamino-2-hydroxy-propane. According to one aspect, the poly ($C_2$-$C_4$)alkylene glycol is a polyethylene glycol. According to another aspect, the poly ($C_2$-$C_4$) alkylene glycol has a $M_n$ of from 200 D (Daltons) to 10 kD (kiloDaltons), from 250 D to 5 kD, or from 400 D to 4 kD. In one aspect, the dicarboxylic acid is sebacic acid. In another aspect, the aliphatic $C_3$-$C_7$ polyol with at least 3 hydroxyl groups is glycerol. In yet another aspect, the molar feed percentage of the poly ($C_2$-$C_4$)alkylene glycol to the dicarboxylic acid ranges from 10% to 50%, or from 15% to 40%. In a further aspect, the poly ($C_2$-$C_4$)alkylene glycol is polyethylene glycol has a Mn (number average molecular mass) of from 400 D to 4 kD, the dicarboxylic acid is sebacic acid, and the feed percentage of polyethylene glycol to sebacic acid ranges from 15% to 40%. In yet another aspect, the composition has a $M_n$ of from 3 kD to 10 kD and/or a polydispersity index of less than 2.

According to another aspect of the present disclosure, a method of preparing a biocompatible elastomer copolymer is provided. The method comprising: condensing in a reaction mixture a $C_8$-$C_{12}$ aliphatic dicarboxylic acid (e.g., —C(O)—($CH_2$)$_{6-10}$—C(O)—) with a poly($C_2$-$C_4$ alkylene glycol) to produce a first product; and adding an aliphatic $C_3$-$C_7$ polyol with at least 3 hydroxyl groups, in one example glycerol, and 1,3-diamino-2-hydroxy-propane to the reaction mixture and condensing the first product with the aliphatic $C_3$-C7 polyol with at least 3 hydroxyl groups, e.g. glycerol, and 1,3-diamino-2-hydroxy-propane (DAHP) to produce the elastomer. According to one aspect, the feed molar ratio of the $C_8$-$C_{12}$ aliphatic dicarboxylic acid ranges between 90% and 110% of the sum of the feed molar ratios of the poly($C_2$-$C_4$ alkylene glycol), the glycerol and the DAHP in the reaction mixture. In other words, as illustrated in Table 2 and in reference to the reaction shown in FIG. 1, the number of moles of the $C_8$-$C_{12}$ aliphatic dicarboxylic acid, e.g., sebacic acid, fed into the reaction, and used in the first and second steps equals the sum of the number of moles of the poly($C_2$-$C_4$ alkylene glycol), e.g., PEG, glycerol and DAHP. Although it may be preferable in some instances that the feed molar ratio of the $C_8$-$C_{12}$ aliphatic dicarboxylic acid equals (substantially or essentially) the sum of the feed molar ratios of the poly($C_2$-$C_4$ alkylene glycol), the glycerol and the DAHP in the reaction mixture, understanding that the same or similar composition may be made with variation in the feed ratios, there may be variation in the feed ratios of the various ingredients, the feed molar ratio of the $C_8$-$C_{12}$ aliphatic dicarboxylic acid may range between 90% and 110% of the sum of the feed molar ratios of the poly($C_2$-$C_4$ alkylene glycol), the glycerol and the DAHP in the reaction mixture, which is a +/−10% variation, or even more so long as the composition is made by the process.

In one aspect, the feed molar ratio of the poly($C_2$-$C_4$ alkylene glycol) is between 15% and 40% of the feed molar ratio of the $C_8$-$C_{12}$ aliphatic dicarboxylic acid. In another aspect, the feed molar ratio of the DAHP is between 1- and 3-times the feed molar ratio of the glycerol, for example the feed molar ratio of the DAHP is, is about, or is approximately twice the feed molar ratio of the glycerol. According to one aspect, the poly($C_2$-$C_4$ alkylene glycol) is poly(ethylene glycol) (PEG). According to another aspect, the $C_8$-$C_{12}$ aliphatic dicarboxylic acid is sebacic acid. In a further aspect, the poly($C_2$-$C_4$ alkylene glycol) is poly(ethylene glycol), the $C_8$-$C_{12}$ aliphatic dicarboxylic acid is sebacic acid, and the feed ratios of sebacic acid:glycerol:DAHP:PEG are 3:(0.6 to 0.85):(1.2 to 1.7):(0.45 to 1.26), where the sum of the feed ratios of the glycerol, DAHP and PEG is, is approximately, or is about 3, or is 3+/−0.3, e.g., the feed ratios of sebacic acid:glycerol:DAHP:PEG are selected from 3:0.85:1.7:0.45, 3:0.75:1.5:0.75, and 3:0.6:1.2:1.2. In yet another aspect, the poly(C2-C4 alkylene glycol) has a $M_n$ of from 250 D to 5 kD, e.g., from 400 D to 4 kD, such as 400 D, 1 kD, 2 kD and 4 kD. In one further aspect, the the condensation is performed by heating the reaction mixture in an inert atmosphere, e.g. argon, optionally under reduced (less than atmospheric, e.g., less than 0.001 atm (atmosphere), e.g., 300 mTorr) pressure.

In yet another aspect, a method of culturing cells is provided. The method comprises placing a composition in any aspect described above or herein in a suitable cell growth medium; contacting cells with the composition; and culturing cells under conditions suitable for cell growth.

The polymer compositions according to any aspect described herein, may be modified to include biologically active groups or active agents either covalently bound (attached) to the polymer structure or bound to the structure non-covalently. Active agents can be admixed with the polymer composition, absorbed or adsorbed into the composition. Active agents that may be incorporated into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (.+−.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, ciprofloxacin, norfloxacin, afloxacin, levofloxacin, gentamicin, tobramycin, neomycin, erythromycin, trimethoprim sulphate, polymixin B and silver salts such as chloride, bromide, iodide and periodate.

Active agents that may be bound to the polymer composition include peptides (e.g., ECM epitopes) for functionalizing the gel with a biologically functional group. Useful peptides include or consist of the following amino acid sequences: IKLLI (SEQ ID NO: 1)(anti-apoptotic), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12), RNIAEIIKDI (SEQ ID NO: 13), DGEA (SEQ ID NO: 14), VTXG (SEQ ID NO: 15), PRRARV (SEQ ID NO: 16), YEKPGSPPREVVPRPRPGV (SEQ ID NO: 17), RPSLAK-KQRFRHRNRKGYRSQRGHSRGR (SEQ ID NO: 18), RIQNLLKITNLRIKFVK (SEQ ID NO: 19), RGD, IKVAV (SEQ ID NO: 20) and IKVAVS (SEQ ID NO: 21). In one example, these oligopeptides are linked via their amine groups to the polymeric structures described herein. In another embodiment, biomolecules are attached or bound to the polymer composition which aid in evasion of an immune response. Non-limiting examples of such peptides are:

betaine, derivatives of betaine, and other zwitterionic groups including certain amino acids and their derivatives.

The active agent or any compound or composition may be bound to the polymer in any useful manner, for instance: covalently (including by coordination and by use of a suitable linkers and linking methods as are broadly known and are broadly available in the art, for example linkers and methods of use of linkers are commercially available from Thermo Fisher Scientific, Pierce Protein Research Products, Rockford, Ill., see also Thermo Scientific Pierce Crosslinking Technical Handbook, 2009 Thermo Fisher Scientific Inc.), by affinity or charge (that is, non-covalently), or by intermixing with the polymer when the composition is in solution phase. Binding of the active agent or any compound or composition by affinity or charge, e.g., by polar, hydrogen bonding, charge (ionic/electrostatic), or van der Waals interactions, may be preferred in many instances because the compound is not free to diffuse prior to or after gelation, as in the case of the active agent being intermixed with the polymer in the composition, or is not covalently modified, which can hamper efficacy of the active agent.

In another aspect a polymer composition as described herein is used as a carrier for release of an active agent e.g., for therapeutic purposes. In certain aspects, the composition is used for release of one or more therapeutic agents within a patient's body and/or incorporates one or more therapeutic agents. For example, at least one therapeutic agent is added to the composition described herein before it is implanted in the patient or otherwise administered to the patient, for example, a therapeutic agent is added to the described composition by adsorption to or absorption into the scaffold, by chemical cross-linking after heat curing, by mixture with the polymer composition prior to heat curing provided the therapeutic agent is heat-stable, or by mixture into an electrospinning composition if the therapeutic agent is stable under such conditions. Generally, the therapeutic agents include any substance that can be coated on, embedded into, absorbed into, adsorbed to, or otherwise attached to or incorporated onto or into the composition described herein or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a composition comprising neurotrophic agents or cells that express neurotrophic agents may be applied to a wound that is near a critical region of the central nervous system, such as the spine.

Any useful cytokine or chemoattractant can be mixed into, mixed with, co-applied or otherwise combined with any composition as described herein. For example and without limitation, useful components include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

Non-limiting examples of antiangiogenic agents include: Macugen (pegaptanib sodium); Lucentis; Tryptophanyl-tRNA synthetase (TrpRS); AdPEDF; VEGF TRAP-EYE; AG-013958; Avastin (bevacizumab); JSM6427; TG100801; ATG3; Perceiva (originally sirolimus or rapamycin); E10030, ARC1905 and colociximab (Ophthotech) and Endostatin. Ranibizumab is currently the standard in the United States for treatment of neovascular AMD. It binds and inhibits all isoforms of VEGF. Although effective in many cases, treatment with ranibizumab requires sustained treatment regimens and frequent intravitreal injections. VEGF Trap is a receptor decoy that targets VEGF with higher affinity than ranibizumab and other currently available anti-VEGF agents. Blocking of VEGF effects by inhibition of the tyrosine kinase cascade downstream from the VEGF receptor also shows promise, and includes such therapies as vatalanib, TG100801, pazopanib, AG013958 and AL39324. Small interfering RNA technology-based therapies have been designed to downregulate the production of VEGF (bevasiranib) or VEGF receptors (AGN211745). Other potential therapies include pigment epithelium-derived factor-based therapies, nicotinic acetylcholine receptor antagonists, integrin antagonists and sirolimus. (See, e.g., Chappelow, A V, et al. Neovascular age-related macular degeneration: potential therapies, *Drugs.* 2008; 68(8):1029-36 and Barakat M R, et al. VEGF inhibitors for the treatment of neovascular age-related macular degeneration, Expert Opin Investig Drugs. 2009 May; 18(5): 637-46.

In another aspect, antioxidants are added to the polymeric composition, such as organic or inorganic antioxidants. In one aspect, the antioxidant is a nanoparticle incorporated by any means into the polymer composition, such as, for example, a cerium nanoparticle. As an example, an anisotropic heart valve or heart valve leaflet prosthesis is manufactured by electrospinning, or by any useful method, and cerium nanoparticles are deposited in and/or on the prosthesis either during or after manufacture.

Pharmaceutically acceptable salts of any active agent (e.g., therapeutic agent or drug), bound to or otherwise combined with the polymeric composition according to any aspect herein, may be employed. Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

In certain non-limiting aspects, cells are added to the composition. Non-limiting examples of useful cells include: stem cells, progenitor cells and differentiated cells; recombinant cells; muscle cells and precursors thereof; nerve cells and precursors thereof; mesenchymal progenitor or stem cells; bone cells or precursors thereof, such as osteoprogenitor cells, etc. Cells can be mixed into the composition or can be included on or within a substrate such as a biological scaffold, combined with the composition, for example, by seeding and growing the cells on the cured or otherwise processed scaffold. In one aspect, the substrate is seeded with cells, the cells are grown and/or adapted to the niche created by incubation in a suitable medium in a bioreactor or incubator for a suitable time period to optimally/favorably prepare the composition for implantation in a patient. The substrate can be seeded with cells to facilitate in-growth, differentiation and/or adaptation of the cells. For example and without limitation, the cells can be autologous or allogeneic with respect to the patient to receive the composition/device comprising the gel. In one example, a layer of dermis obtained from the patient is seeded on a mold, for use in repairing damaged skin and/or underlying tissue.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

According to a further aspect, a device is provided comprising a substrate including the polymer composition according to any aspect described herein. In one aspect, the composition is applied to or otherwise combined with, for example and without limitation: a woven material; a nonwoven material; a mesh; a suture; a stent; an aneurysm coil; a metallic implant; a polymeric implant; a ceramic implant; an ECM composition, substrate or device such as a sheet, thread, powder, tube, an aligned/anisotropic or isotropic fibrous structure; a composite with synthetic or natural ECM material, etc. Methods of treating a patient in need thereof also are provided, comprising implanting or otherwise administering to a patient a composition or device according to any aspect provided herein. In another aspect, a method of treating a wound or defect in a patient is provided, comprising delivering to a site in or on the patient a composition or device according to any aspect provided herein. Where the site in the patient is internal, the composition may be delivered by a needle, cannula, catheter, trocar or any similar devices, or by any suitable surgical procedure.

In a further aspect, a commercial kit is provided comprising a composition described herein. A kit comprises suitable packaging material and the composition. In one non-limiting embodiment, the kit comprises a liquid, gelled or dried polymeric composition according to any aspect described herein in a vessel, which may be the packaging, or which may be contained within packaging. The vessel may be a vial, syringe, tube or any other container suitable for storage and transfer in commercial distribution routes of the kit. Likewise, a product, such as a device, gel, scaffolding, suture, prosthetic, mesh, etc. including one or both of the soluble or structural compositions described herein may be packaged appropriately for commercial distribution.

The compositions according to any aspect described herein may find use as cell growth scaffolds. Cells may be microintegrated within a cell growth matrix using a variety of methods, such as by seeding. In one example, a polymeric composition as described herein is submersed in an appropriate growth medium for the cells to be incorporated, and then directly exposed to the cells. The cells are allowed to proliferate on the surface and interstices of the composition. The composition is then removed from the growth medium, washed if necessary, and implanted in a patient. Cells of interest also can be dissolved into an appropriate solution (e.g., a growth medium or buffer) and then sprayed onto the polymeric composition. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the polymeric composition. Electrospraying involves subjecting a cell-containing solution with an appropriate viscosity and concentration to an electric field sufficient to produce a spray of small charged droplets of solution that contain cells.

Examples of cells that may be incorporated on or into the gel includes stem cells such as adipose or neural stem cells; progenitor (precursor) cells; smooth muscle cells; skeletal myoblasts; myocardial cells; endothelial cells; endothelial progenitor cells; bone-marrow derived mesenchymal cells and genetically modified cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF or FGF-2), acidic fibroblast growth factor (aFGF), nerve growth factor (NGF), vascular endothelial growth factor (VEGF), hepatocyte growth factor (HGF), insulin-like growth factors (IGF), transforming growth factor-beta pleiotrophin protein, midkine protein.

As described above, the compositions described herein are useful for drug delivery, especially were systemic treatment is not necessary or dangerous. One or more therapeutic agents may be included in the compositions and the composition is delivered to a site in a patient. Delivery of the composition is limited at least in part, by the rate of degradation of the polymeric component of the composition. As such, the composition may be useful in treating tumors, for example, by complexing an anticancer agent with the polymeric component of the composition and delivering the composition to the site of a tumor, where it slowly releases the anticancer agent. Likewise, these compositions may find use in treating localized conditions, such as abcesses. The composition may be useful in delivering steroids at a constant rate, for example in the case of testosterone, where less than optimal injections, topical gels and patches are the norm, or contraceptives.

Example 1—PEGylated Poly(Ester Amide) Elastomers with Tunable Physicochemical, Mechanical and Degradation Properties Biodegradable synthetic elastomers such as poly(1,3-diamino-2-hydroxypropane-co-polyol sebacate)s (APS) are gaining importance in soft tissue engineering applications due to their biocompatibility and mechanical compliance. However, APS-based thermoset elastomers possess narrow spectrum of physicochemical and functional properties, limiting their biomedical applications. In this study, we overcome these limitations by incorporating biocompatible polyethylene glycol (PEG) into the polymer backbone. A series of novel APS-co-PEG copolymers were synthesized by varying PEG mole percentage (15-40%) and PEG molecular weight (400 Da to 4 kDa) to tune the physicochemical, mechanical and degradation properties. APS-co-PEG pre-polymers were characterized by nuclear magnetic resonance ($^1$H NMR), Fourier transform infrared spectroscopy (FTIR), gel permeation chromatography (GPC) and differential scanning calorimetry (DSC). The pre-polymers were thermally crosslinked into copolymer films and characterized for mechanical and degradation properties. Solubility of APS-co-PEG pre-polymers in common organic solvents was significantly improved by incorporation of PEG. Changes in molar percentage and molecular weight of PEG, monomer feed ratio and crosslinking time resulted in a wide range of ultimate tensile strength (0.07-2.38 MPa), elastic modulus (0.02-3.0 MPa) and elongation (93-993%) in crosslinked APS-co-PEG films. PEG incorporation increased the hydration of APS-co-PEG films, leading to tunable degradation rates (10-40% mass loss over 14 days). APS-co-PEG films also supported cell proliferation. The broad spectrum of properties exhibited by this novel series of elastomers indicates their promise in potential applications for soft tissue engineering.

This example addresses the question of whether incorporation of PEG into the APS structure will yield poly (1,3-diamino-2-hydroxypropane-co-glycerol sebacate)-co-poly(ethylene glycol) (APS-co-PEG) copolymers with tunable physicochemical, mechanical, and degradation properties. This will expand the repertoire and property spectrum of currently available elastomers for biomedical applications. Here, we report the synthesis and characterization of a series of APS-co-PEG polymers with varying PEG mole % ranging from 10-40% of sebacic acid (SA) and PEG molecular weight ranging from 400 Da to 4 kDa.

Materials and Methods

Pre-Polymer Synthesis: Synthesis of Poly(1,3-Diamino-2-Hydroxypropane-Co-Glycerol Sebacate) Pre-Polymer—

Sebacic acid (SA), glycerol (G) and 1,3-diamino-2-hydroxy-propane (DAHP) were purchased from Sigma-Aldrich. The APS pre-polymer was synthesized by the polycondensation reaction of DAHP, G and SA (C. J. Bettinger, et al. Amino alcohol-based degradable poly(ester amide) elastomers, Biomaterials 29 (15) (2008) 2315-2325). Briefly, a round bottom flask was charged with a molar ratio of 2:1:3 of DAHP:G:SA monomer mixture. The reactants were heated under argon atmosphere at 120° C. for 3 h. Approximately 300 mTorr vacuum was applied to the reaction system and the reaction continued for another 9 h at 120° C. to obtain APS pre-polymer. The pre-polymer samples were characterized for their chemical composition. Product yield: 77.8%.

Pre-Polymer Synthesis: Synthesis of Poly(1,3-Diamino-2-Hydroxypropane-Co-Glycerol Sebacate)-Co-Poly(Ethylene Glycol) (APS-Co-PEG) Pre-Polymers—

The synthesis of APS-co-PEG is shown in FIG. 1. Briefly, APS-co-PEG pre-polymers were synthesized via a one-pot two step condensation polymerization. The first step is the polycondensation between SA and PEG. The mixture was heated in a round bottom flask at 130° C. under Argon atmosphere for 2 h and the reaction was continued at 120° C. under reduced pressure of 300 mTorr for 24, 48 or 72 h to optimize the time of the first reaction. In the second step, specific amounts of G and DAHP (Tables 1 and 2) were added into the round bottom flask and mixed thoroughly with the reactants. The reaction was stirred at 120° C. under Argon atmosphere for 30 min and continued at 120° C. under the reduced pressure of 300 mTorr for 12 h or 48 h to obtain APS-co-PEG pre-polymers. The pre-polymers obtained were subjected to chemical and thermal characterization.

The effect of first and second step reaction time and monomer feed ratio on the molecular weight and polydispersity of APS-40PEG1K pre-polymer were explored to optimize the reaction conditions. The optimized reaction time and monomer feed ratio were then used to synthesize a library of APS-co-PEG pre-polymers by varying mole percentage of PEG to SA (15%, 25% or 40%) and molecular weights of PEG (400 Da, 1 kDa, 2 kDa, 4 kDa). The pre-polymers were denoted as APS-xPEGy, where x represents the PEG to SA mole percentage and y represents the PEG molecular weight. The detailed molar ratios of the reactants in various pre-polymers can be found in Tables 2 and 4. Product yield: 61.4-72.6%.

Chemical and thermal characterization of pre-polymers. The synthesized APS-co-PEG pre-polymers were analyzed using nuclear magnetic resonance (1H NMR) spectroscopy (Bruker 400). SA and PEG were dissolved in DMSO-d6 and the pre-polymer samples were dissolved in CDCl3. All the spectra were recorded at 400 MHz. 1H NMR (400 MHz, CDCl3, δ/ppm): 1.30 (m, —CH2-), 1.62 (m, —CH2CH2O (CO)—), 2.35 (m, —CH2O(CO)—), 3.64 (m, —OCH2CH2O—), 3.72 (m, —NCH2CHOHCH2N—), 4.22 (m, —OCH2CHOHCH2O—). The peak assignments in the 1H NMR.

spectra for APS-co-PEG pre-polymers are also denoted in FIG. 1(a). To calculate the PEG:SA ratio, peaks of methylene hydrogen within PEG (3.65 ppm) and SA (the combination of 1.30, 1.62, and 2.35 ppm) in 1H NMR spectra were integrated using TopSpin software. Chemical composition of the pre-polymers was studied using Fourier Transform Infrared (FTIR) spectroscopy with attenuated total reflection (ATR-FTIR). The FTIR spectra were recorded in absorption mode with a resolution of 4 cm$^{-1}$ using Bruker Vertex 70 FTIR spectrometer. The results are presented as an average of 256 scans. Ester, amide I and amide II peaks intensity were integrated for semi-quantitative analysis using Origin8 software. The molecular weight of APS-co-PEG pre-polymers was determined by gel permeation chromatography (GPC) using a Waters 515 HPLC pump and a Waters 2414 refractive index detector. The samples were dissolved in tetrahydrofuran (THF) (0.5% w/v), filtered and then injected into a 20 μL loop at the flow rate of 0.5 mL/min. Polystyrene standards were used for calibration. Differential Scanning Calorimeter (DSC, Mettler Toledo) was utilized to study the thermal properties of APS-co-PEG pre-polymers.

Sample (approx. 5 mg) was sealed in an aluminum pan and first heated from room temperature to 150° C. (1st cycle), then cooled to −70° C. (2nd cycle), and finally reheated to 150° C. (3rd cycle) at a heating/cooling rate of 10° C./min. All the processes were carried out under nitrogen atmosphere. Crystallization temperature (Tc) and enthalpy (DHc) were obtained from the cooling cycle (150° C. to −70° C., 2nd cycle) whereas glass transition temperature (Tg), melting temperature (Tm) and enthalpy (DHm) were obtained from the heating cycle (−70° C. to 150° C., 3rd cycle). DSC data was analyzed using STARe software.

Film Fabrication and Chemical Characterization.

APS pre-polymer was uniformly spread on a Teflon dish and thermally cured at 170° C. for 72 h in a vacuum oven to fabricate the APS polymer film. The thickness of the film was around 1.5 mm. Similarly, the APS-co-PEG pre-polymer was spread on a Teflon dish and thermally cured at 170° C. for 24, 48 or 72 h in a vacuum oven. The thickness of films was kept constant around 1.5 mm. The cured polymer films were chemically characterized by ATR-FTIR as described under characterization of pre-polymers.

Mechanical Testing—

The mechanical properties of APS and APS-co-PEG polymer films were evaluated using uniaxial tensile testing with ADMET MTEST Quattro mechanical testing system (n=4). Thermally crosslinked polymer films were cut into rectangular shape (10 mm×7 mm). Samples were stretched until failure at a constant jogging speed of 10 mm/min. The stress (MPa) was obtained by dividing the applied force (N) with cross-section area (mm$^2$) and % elongation (strain) was obtained from the displacement using ((L−L0)/L0*100), where L0 was initial gauge length and L was instantaneous gauge length. Ultimate tensile strength (UTS) was recorded as the maximum stress at sample failure. Elastic modulus was calculated from the linear stress-strain curve between 5% and 15% strain.

Hydration and Degradation Properties of Films.

The hydrophilicity of thermally crosslinked polymer films was determined by contact angle measurements and hydration study. The contact angles of polymer films were measured using VCA 2000 video contact angle goniometer (AST products, n=4). A droplet of de-ionized water was deposited on the sample film using a 21-gauge needle and high-resolution image of the droplet was captured. The contact angles were determined using the VCA software.

For hydration and degradation study, samples were cut into rectangular shape (around 15 mm*7 mm) and immersed in Dulbecco's phosphate buffer saline (DPBS, Corning) at 37° C. in a dry bath shaker (50 RPM) after recording their initial weight (W$_0$) and thickness (t$_0$) (n=3). Samples were taken out from the DPBS solution at regular time intervals, wiped with Kimwipes to remove excess surface water, and vacuum dried for 10 min. The weights (W$_t$) and thickness (t$_t$) of samples at time t as well as at equilibrium (W$_{eq}$ and t$_{eq}$) were recorded. The hydration of the polymer films was determined by Eq. (2). The degradation study was carried out for 14 days in DPBS at 37° C. after the equilibrium hydration was achieved. The mass loss of polymer films during degradation was determined by Eq. (3). The decrease in thickness of the films was determined by Eq. (4). Degraded samples were dried in desiccator and examined by FTIR to study the changes in their chemical structure. Morphology of degraded films was studied by scanning electron microscope (SEM) imaging (JEOL 6335F Field Emission SEM). Dried films before and after degradation were sputter-coated with 5 nm of gold-palladium using Cressington 108 auto sputter-coater and images were obtained using accelerated voltage of 3 kV and a working distance of 8 mm.

$$\text{Equilibrium hydration (\%)}=(W_{eq}-W_0)/W_0\times100 \quad \text{Eq. (2)}$$

$$\text{Mass loss (\%)}=(W_{eq}-W_t)/W_{eq}\times100 \quad \text{Eq. (3)}$$

$$\text{Decrease in thickness (\%)}=(t_{eq}-t_t)/t_{eq}\times10 \quad \text{Eq. (4)}$$

In Vitro Biocompatibility of Films

The mouse myoblast cells (C2C12) ATCC (CRL-1772™) were obtained. The cells were cultured in Dulbecco's Modified Eagle Medium (DMEM, Corning Cellgro) supplemented with 10% Fetal Bovine Serum (FBS, Hyclone, Thermofisher Scientific) and 1% Penicillin/Streptomycin (Corning Cellgro). Cells in passage 2-7 were used. The films (0.5 cm×0.5 cm) were sterilized by exposing to 70% isopropanol under UV light for 30 min, washed with DPBS thrice and seeded with C2C12 cells using a seeding density of 50,000 cells/scaffold. Cells were allowed to adhere for 40 min and then 500 μL of medium was added. After 24 hours, all films were transferred to new wells and the proliferation rate of adhered cells on day 1 and 3 was assessed using an AlamarBlue® assay (Invitrogen) following the standard protocol. Briefly, cell-seeded scaffolds (n=3) were treated with 10% AlamarBlue® in growth media for 3.5 h at 37° C. The fluorescence intensity was then measured using microplate reader (Gen5 Biotek) at excitation/emission wavelengths of 530/590 nm. AlamarBlue® solution (10%) incubated without any cells was used for blank correction.

The films seeded with C2C12 cells were fixed in 4% paraformaldehyde solution (20 min) after 3 day in culture to study cell adhesion and spreading. The films were then washed with DPBS three times, followed by permeabilization and blocking using 0.1% Triton X-100 and 3% bovine serum albumin (BSA) in DPBS, respectively. Cell nuclei and actin were stained using NucBlue® Fixed Cell Stain (Life Technologies) and ActinGreen™ 488 ReadyProbes® Reagent (Life Technologies), respectively. To eliminate the strong autofluorescence of APS and APS-co-PEG polymers, samples were treated with Sudan Black (I. H. Jaafar, et al. Improving fluorescence imaging of biological cells on biomedical polymers, Acta Biomater. 7 (4) (2011) 1588-1598). Briefly, 0.3% (w/v) Sudan Black solution was prepared in 70% ethanol and filtered through 0.45 μm syringe filter. Polymer films were immersed in this solution for 24 h and washed three times before imaging. Confocal images were obtained using inverted confocal laser scanning microscope (Olympus Fluoview 1000) under 20× and 40× objectives.

Statistics

Experimental data were presented as mean±standard deviation. Student's paired t-test was used for comparisons between two groups. Statistical differences between multiple groups were analyzed using one-way ANOVA followed by Tukey's post-hoc analysis. p values less than 0.05 were considered significant.

Results and Discussions

Pre-Polymer Synthesis and Chemical Characterization: Optimization of Reaction Time and Monomer Feed Ratio.

APS-co-PEG pre-polymers were synthesized by two-step polycondensation reaction (FIG. 1). The synthesis conditions of APS-co-PEG pre-polymers, such as reaction time for the first and second step as well as monomer feed ratio were first optimized based on the molecular weight characterization of APS-40PEG1K by GPC (Table 1). Among all the conditions in our trials, optimum durations for the 1st and 2nd step reaction to obtain low polydispersity index (PDI) were determined to be 48 h and 12 h, respectively. Monomer feed ratio plays an important role in determining the Mn of final product during step polymerization. As DAHP and G both have three functional groups, we also synthesized a batch with SA:G:DAHP:PEG molar ratio of 3:0.4:0.8:1.2, in which case, all free hydroxyl groups are expected to react with carboxylic groups of SA (stoichiometry balance, denoted as APS-40PEG1K STOIC). As expected, an increase in molecular weight was observed for APS-40PEG1K STOIC due to the strict stoichiometry (Table 1). However, the mechanical properties of the polymeric film were adversely affected (data discussed in the mechanical properties section). The decrease in the mechanical properties of APS-40PEG1K STOIC films was attributed to the unavailability of free hydroxyl groups required for crosslinking of polymeric chains during the thermal crosslinking step. Therefore, this monomer feed ratio was not adopted for further experiments.

TABLE 1

Molecular weight of APS-40PEG1K pre-polymers under different reaction conditions.

| Polymer | $1^{ST}$ STEP TIME | $2^{ND}$ STEP TIME | MOLAR RATIO (SA:G:DAHP:PEG) | $M_w$/PDI |
|---|---|---|---|---|
| APS-40PEG1K | 24 h | 48 h | 3:0.6:1.2:1.2 | 3536/1.43 |
| | 24 h | 12 h | 3:0.6:1.2:1.2 | 4399/1.56 |
| | 48 h | 12 h | 3:0.6:1.2:1.2 | 4997/1.26 |
| | 72 h | 12 h | 3:0.6:1.2:1.2 | 5387/1.39 |
| | 48 h | 12 h | 3:0.4:0.8:1.2 (Stoichiometry balance) | 6060/1.81 |

Figure 2A:
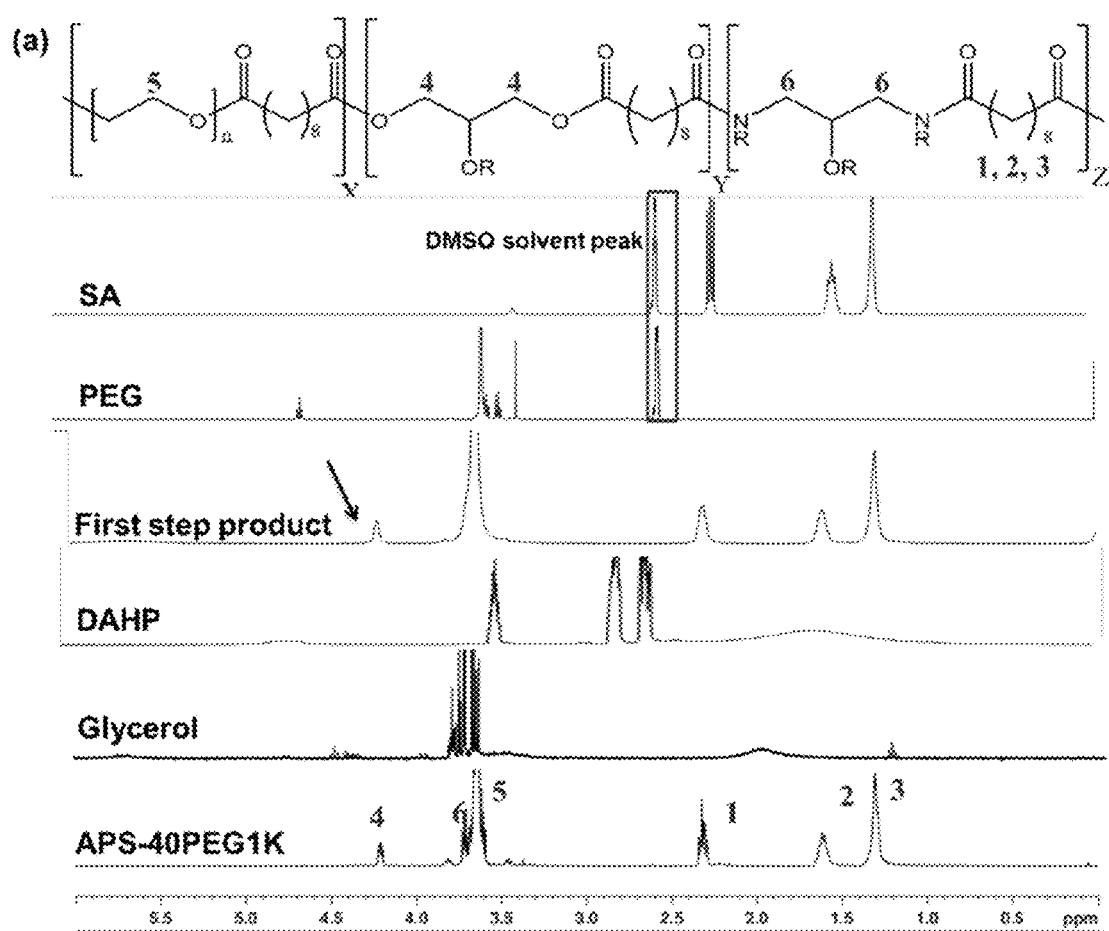
FIGS. 2A and 2B. (a) $^1$H NMR spectra of SA, PEG, DAHP, glycerol and APS-40PEG1K pre-polymer. Peak assignments for APS-40PEG1K are representative for APS-co-PEG pre-polymers. Reaction between PEG and SA resulted in the first step product with a new peak at 4.2 ppm (pointed by the arrow) corresponding to the peak of αH beside the newly formed ester bond. The αH in G and DAHP is shifted from 3.5-3.7 ppm to 4.20 ppm and 2.5-2.7 ppm to 3.72 ppm, respectively. (b) FTIR spectra of PEG1K, APS-40PEG1K pre-polymer and APS. Appearance of characteristic PEG peaks corresponding to C—H bending (1464 and 1343 cm$^{-1}$) & C—O—C stretching (1100 cm$^{-1}$) and APS peaks corresponding to carbonyl (1730 cm$^{-1}$) and amide peaks (1646 and 1552 cm$^{-1}$) in APS-40PEG1K spectrum suggests successful synthesis of the copolymer. (c) Decrease in bond intensity ratio of amide peaks I (1646 cm$^{-1}$) to carbonyl peak (1730 cm$^{-1}$) and Amide 11 (1552 cm$^{-1}$) to carbonyl peak (1730 cm$^{-1}$) suggests decreased amide formation due to reduced DAHP to SA molar ratio and increased ester formation due to PEG incorporation into APS backbone.

APS-40PEG1K (SA:G:DAHP:PEG molar ratio of 3:0.6:1.2:1.2) synthesized under optimal conditions was subjected to chemical characterization by $^1$H-NMR and FTIR. $^1$H-NMR characterization of the first step reaction product exhibited a new peak at 4.2 ppm (FIG. 2a) corresponding to the αH adjacent to the ester bond, indicating the formation of new ester bonds and a successful reaction between SA and PEG. In addition, the methylene hydrogen peaks of SA were present at 1.30 ppm and 1.62 ppm, and those of PEG at 2.35 ppm and 3.65 ppm, respectively. In the second step, G and DAHP were added to obtain APS-co-PEG pre-polymer. The 1H NMR spectrum of the copolymer APS-40PEG1K after completion of 2nd step did not show any peaks from the monomers G or DAHP (FIG. 2a). Instead, due to the ester and amide bond formation, the αH in glycerol shifted from 3.5-3.7 ppm to 4.2 ppm and that in DAHP shifted from 2.5-2.7 ppm to 3.72 ppm. Taken together, these results indicated successful completion of the reaction. The actual mole % of PEG calculated from $^1$H NMR by comparing methylene hydrogen within PEG and SA correlated well with the theoretical mole %, indicating good control over the polymer synthesis process (Table 2).

Figure 2B:
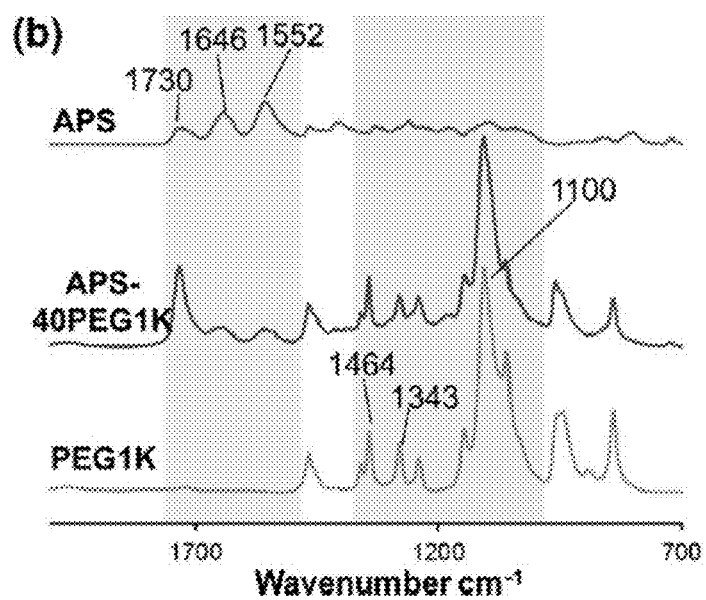

The FTIR spectra of APS-40PEG1K pre-polymer, APS pre-polymer and PEG further demonstrated successful completion of the reaction (FIG. 2b). Of note, the carbonyl peak (1730 cm$^{-1}$) observed in the spectra of APS and APS-40PEG1K indicated the formation of ester bonds between SA and G/PEG while amide (1646 and 1552 cm$^{-1}$) peaks indicated bonds between SA and DAHP in the pre-polymer chains. In addition, the intensity ratios of the amide I (1646 cm$^{-1}$) to carbonyl peak of ester bond (1730 cm$^{-1}$) and amide II (1552 cm$^{-1}$) to carbonyl peak of ester bond (1730 cm$^{-1}$) were lower in the FTIR spectrum of APS-40PEG1K than the corresponding ratios observed in the spectrum of APS (FIG. 2c). This is due to the reduced amide bond formation in APS-co-PEG pre-polymer than that in APS and may be attributed to the reduced SA: DAHP ratio with addition of PEG (Table 2). The increase in ester bond formation with addition of PEG also suggested that PEG was covalently bonded to SA and not physically blended in the copolymer structure. In addition, peaks at 1100, 1464 and 1343 cm$^{-1}$ characteristic of C—O—C stretching and C—H bending peaks of PEG were observed in the spectrum of APS-40PEG1K pre-polymer, but not in the APS pre-polymer spectrum (FIG. 2b). Taken together, these data indicated successful covalent linkage of PEG to APS backbone.

TABLE 2

Effect of PEG mole % on the molecular weight of APS-co-PEG pre-polymers

| Polymer | Molar ratio (SA:G:DAHP:PEG) | Mn/PDI | Theoretical/actual PEG molar percentage (%)$^a$ |
|---|---|---|---|
| APS | 3:1:2:0 | NA | NA |
| APS-15PEG1K | 3:0.85:1.7:0.45 | 2850/1.19 | 15/17.7 |
| APS-25PEG1K | 3:0.75:1.5:0.75 | 4024/1.35 | 25/25.5 |
| APS-40PEG1K | 3:0.6:1.2:1.2 | 4997/1.26 | 40/44.1 |

SA: sebacic acid, G: glycerol, DAHP: 1,3-diamino-2-hydroxy-propane, PEG: polyethylene glycol, PDI: polydispersity index.
$^a$Actual PEG molar percentage is calculated from the $^1$H NMR spectra by determining the ratio between methylene hydrogen within PEG and SA.

Pre-Polymer Synthesis and Chemical Characterization: Effect of PEG Mole % and Molecular Weight on Chemical Composition.

Based on the optimized reaction conditions, we synthesized a series of APS-co-PEG pre-polymers by changing PEG mole % (15, 25 and 40% of PEG1K) and PEG molecular weight (400 Da, 1 kDa, 2 kDa and 4 kDa at 25% PEG) to tune the physicochemical, mechanical and degradation properties of the copolymer. These polymers were labeled as APS-15PEG1K, APS-25PEG1K, APS-40PEG1K (Table 2), and APS-25PEG400, APS-25PEG2K, and APS-25PEG4K (Table 3). Indeed, compared to the poor solubility of APS in major solvents such as chloroform and ethanol (only soluble in 1,1,1,3,3,3-hexafluoroisopropanol, HFIP), APS-co-PEG pre-polymers exhibited increased hydrophilic nature and could be dissolved in commonly used solvents (Table 3). For instance, APS solubility was less than 5 mg/ml in ethanol and chloroform, while APS-co-PEG solubility was more than 200 mg/ml in both solvents. The increased copolymer solubility allowed for their chemical characterization by NMR spectroscopy and GPC and potentially increased the processability of the pre-polymer.

TABLE 3

Solubility of APS-co-PEG pre-polymers in commonly used solvents (mg/ml).

| Polymer | chloroform | ethanol | HFIP |
|---|---|---|---|
| APS | <5 | <5 | >150 |
| APS-15PEG1K | >100 | >200 | >150 |
| APS-25PEG1K | >100 | >250 | >150 |
| APS-40PEG1K | >250 | >300 | >150 |
| APS-25PEG400 | >100 | >250 | >150 |
| APS-25PEG2K | >250 | >300 | >150 |
| APS-25PEG4K | >250 | >300 | >150 |

Figure 3:
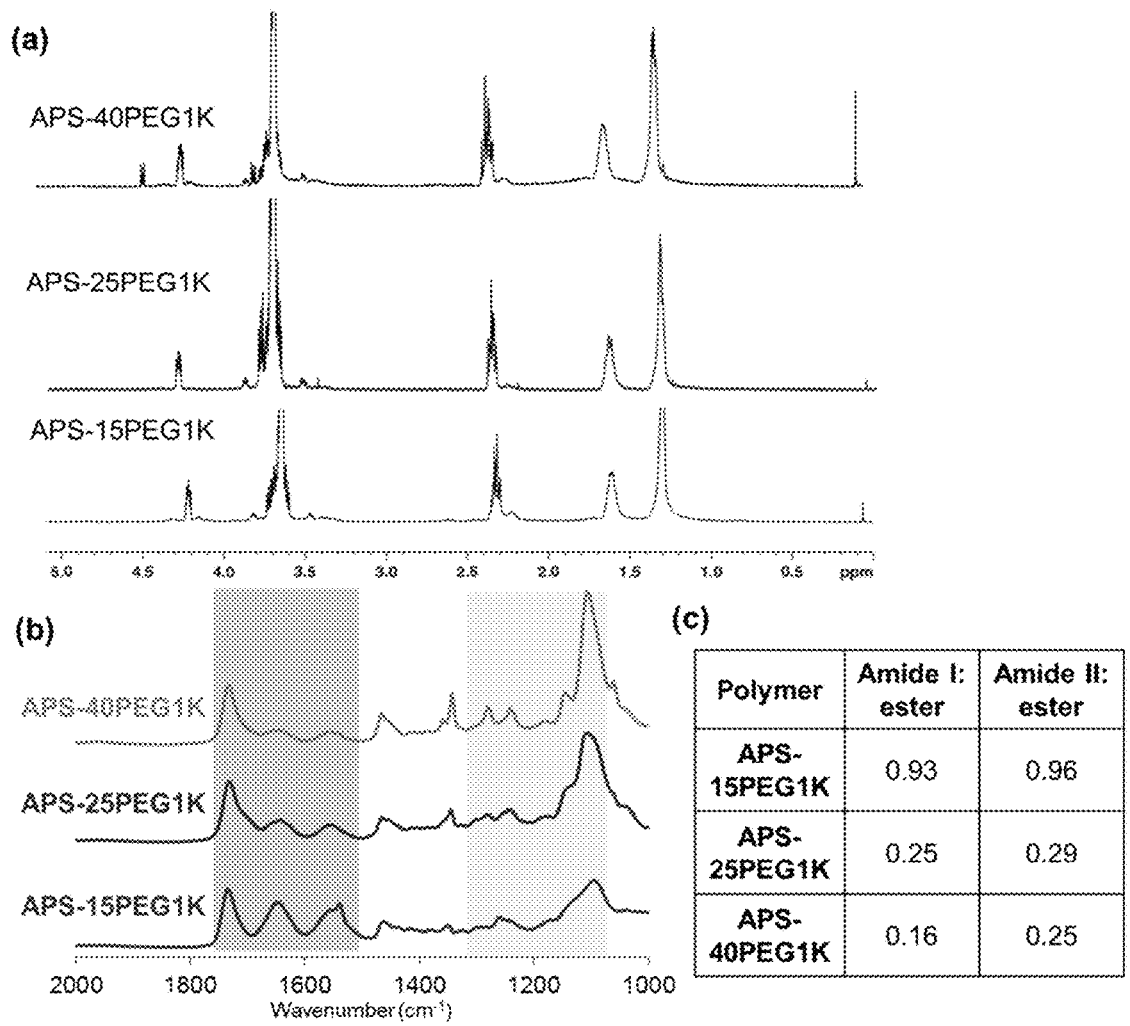
FIG. 3 Chemical characterization of APS-co-PEG pre-polymers with varying mole % of PEG 1 kDa; a) $^1$H NMR, (b) FTIR spectra of APS-15PEG1K, APS-25PEG1K, APS-40PEG1K pre-polymers. c) Intensity ratio of amide peaks I to ester peak (1646/1730 cm$^{-1}$) and amide II to ester peak (1552/1730 cm$^{-1}$) for APS-15PEG1K, APS-25PEG1K and APS-40PEG1K.

The effect of PEG mole % on the chemical properties of APS-co-PEG pre-polymers is shown in FIG. 3. Mn/PDI and actual PEG molar percentage for each pre-polymer are listed in Table 1. Molecular weight of APS-co-PEG pre-polymers increased with the increase in PEG mole %. In all batches, the actual mole % of PEG from NMR correlated well with the theoretical estimation (Table 2), indicating good control over the polymer synthesis process. As expected, the intensity ratio of the amide I to carbonyl peak (1646/1730 cm-1) and Amide II to carbonyl peak of ester bond (1552/1730 $cm^{-1}$) decreased with increasing PEG mole % in the pre-polymer (FIG. 3 (b) and (c)). With the increase in PEG mole %, intensity of C—O—C stretching peak (1110 $cm^{-1}$) and C—H bending peaks (1464 and 1343 $cm^{-1}$) of PEG also increased, indicating increased amount of PEG segments in the copolymer chains (FIG. 3).

Figure 4:
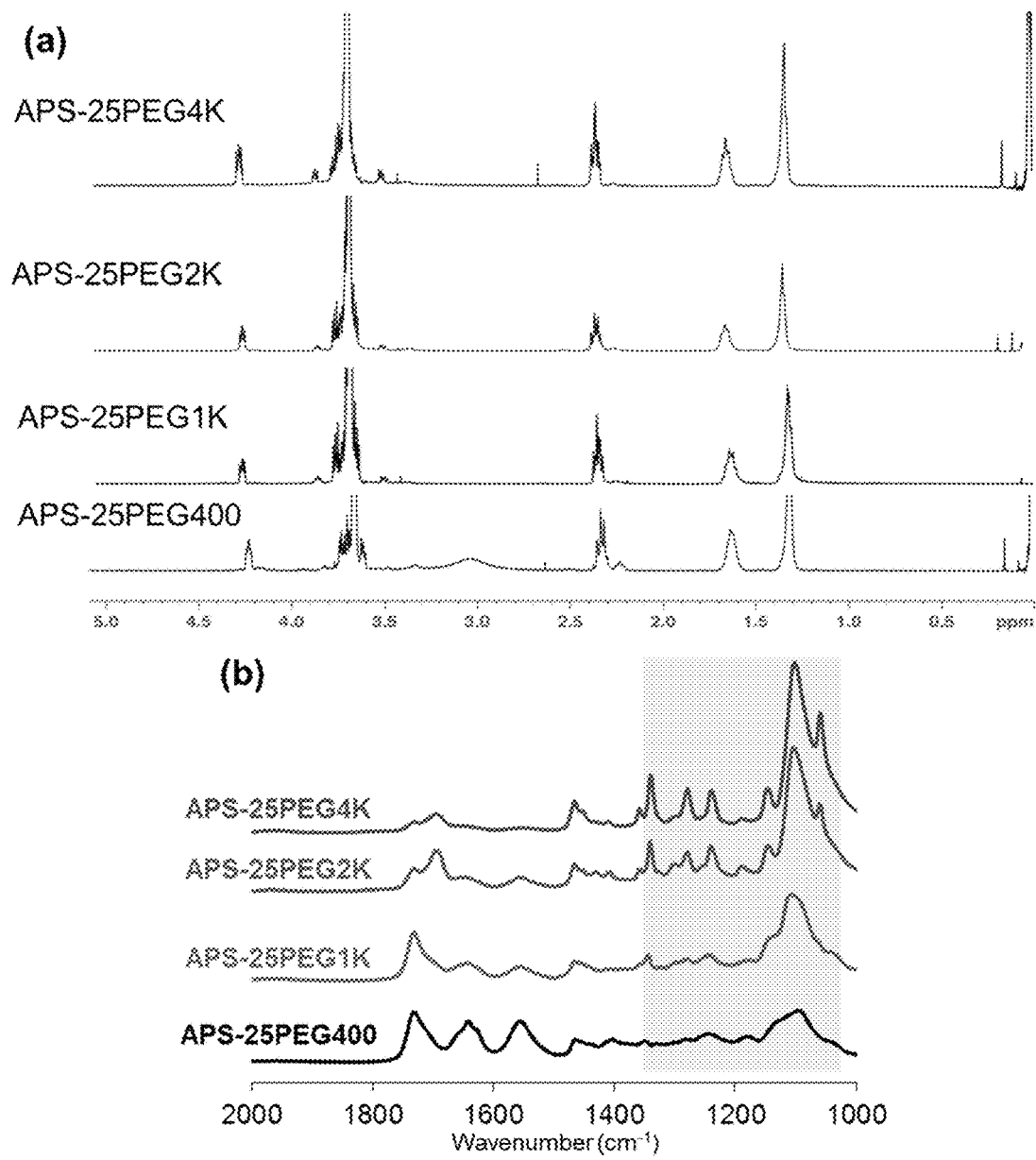
FIG. 4 Chemical characterization of APS-co-PEG pre-polymers with 25 mole % PEG and varying PEG molecular weight (a) $^1$H NMR and (b) FTIR0 spectra of APS-25PEG400, APS-25PEG1K, APS-25PEG2K, APS-25PEG4K pre-polymers.

The effect of PEG molecular weight on the chemical properties of APS-co-PEG pre-polymers is summarized in Table 4 and FIG. 4. Their analyses are similar to those obtained from Table 2 and FIG. 3. Briefly, the effect of increasing PEG molecular weight was similar to that of increasing PEG mole % and led to a predominant increase in intensity of C—O—C stretching peak (1110 $cm^{-1}$) and C—H bending peaks (1464 and 1343 $cm^{-1}$) of PEG, indicating increased amount of PEG segments in the co-polymer chains.

TABLE 4

Effect of PEG molecular weight on the molecular weight of APS-co-PEG pre-polymers

| Polymer | Molar Ratio (SA:G:DAHP:PEG) | $M_n$/PDI | Theoretical/Actual PEG molar percentage (%)* |
|---|---|---|---|
| APS-25PEG400 | 3:0.75:1.5:0.75 | 1836/1.03 | 25/31.1 |
| APS-25PEG1K | 3:0.75:1.5:0.75 | 4024/1.35 | 25/25.5 |
| APS-25PEG2K | 3:0.75:1.5:0.75 | 5064/1.17 | 25/31.3 |
| APS-25PEG4K | 3:0.75:1.5:0.75 | 5618/1.34 | 25/24.3 |

SA: sebacic acid, G: glycerol, DAHP: 1,3-diamino-2-hydroxy-propane, PEG: polyethylene glycol, PDI: polydispersity index,
*Actual PEG molar percentage is calculated from the $^1$H NMR spectra by determining the ratio between methylene hydrogen within PEG and SA.

Pre-Polymer Synthesis and Chemical Characterization: Thermal Properties of APS-Co-PEG Pre-Polymers.

DSC was used to examine the thermal properties of APS-co-PEG pre-polymers. Ideal elastomers for biomedical applications should have a $T_g$ lower than body temperature to ensure that the elastomeric properties could be exhibited in vivo. PEG is a known semi-crystalline polymer with different degree of crystallinity determined by molecular weight while APS is determined to be amorphous. Therefore, it is worthwhile to interrogate the effect of PEG incorporation on the thermal properties of newly synthesized polymers. In this study, the samples were first heated to 150° C. to eliminate thermal history. The cooling cycle (from 150° C. to −70° C.) was used to obtain Tc and DHc while the second heating cycle (−70° C. to 150° C.) was used to obtain Tg, Tm and DHm.

Figure 5:
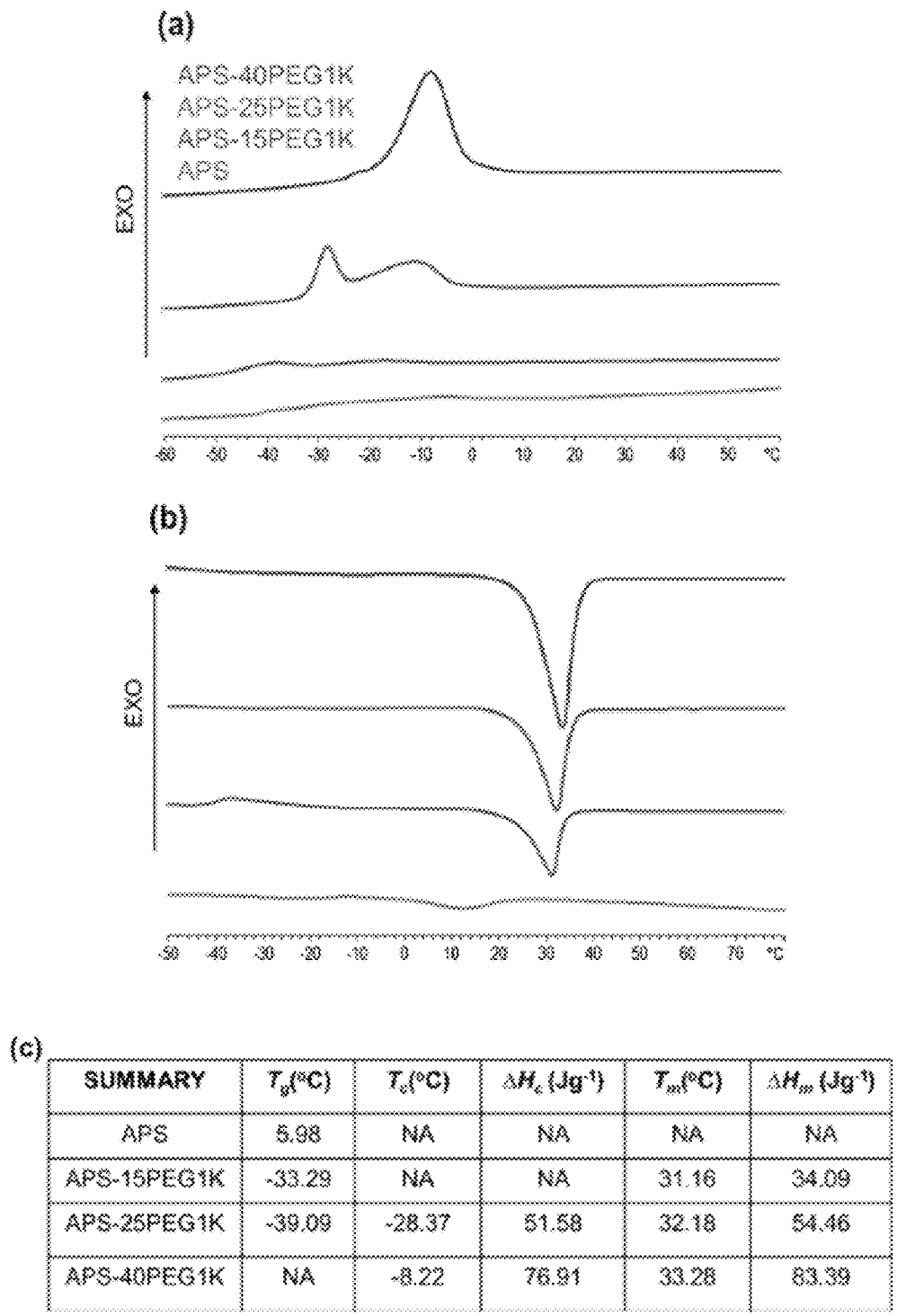
FIG. 5. Effect of PEG mole % on the thermal properties of APS-co-PEG pre-polymers (a) DSC curves of the cooling cycle ($2^{nd}$) and the heating cycle ($3^{rd}$) of APS-co-PEG pre-polymers (top to bottom in (a) and (b): APS-40PEG1K, APS-25PEG1K, APS-15PEG1K, and APS), (c) Summary of the thermal properties of APS-co-PEG pre-polymers with varying PEG mole % (0-40%).

The effect of PEG mole % on the thermal properties of APS-co-PEG pre-polymers is summarized in FIG. 5. Similar to APS pre-polymer, APS-15PEG1K did not show any crystallization peak. Increase in the PEG concentration to 25% resulted in the appearance of crystallization peak at −28.37° C. With further increase in PEG concentration to 40%, $T_c$ shifted to higher temperatures and higher $\Delta H_c$ indicated improved crystallization capacity. The $T_g$ of APS was determined to be 5.98° C. (FIG. 5 (b) and (c)). APS-15PEG1K and APS-25PEG1K were observed to have much lower $T_g$ of −33.29° C. and −39.09° C., respectively. The $T_g$ of APS-40PEG1K cannot be clearly identified in the temperature range studied here. Decrease in $T_g$ with increase in PEG mole % may be due to enhanced polymer chain flexibility by a higher number of PEG segments in the copolymer chain. This also suggests that PEG exhibits its plasticizer effect on the copolymer chains. Low $T_g$ (below body temperature) promises the application of these elastomers in tissue engineering. Also, higher $T_m$ and $\Delta H_m$ were observed with the increase in the PEG mole %. This observation was in agreement with the previous thermal study on PCL-PEG, where increasing content of PEG resulted in higher Tm and stronger melting peaks (S. Zhou, et al., Biodegradable poly(ε-caprolactone)-poly(ethylene glycol) block copolymers: characterization and their use as drug carriers for a controlled delivery system, Biomaterials 24 (20) (2003) 3563-3570). It also indicated that the crystallization tendency as well as the degree of crystallization was higher in APS-co-PEG pre-polymers with higher PEG content.

Figure 6:
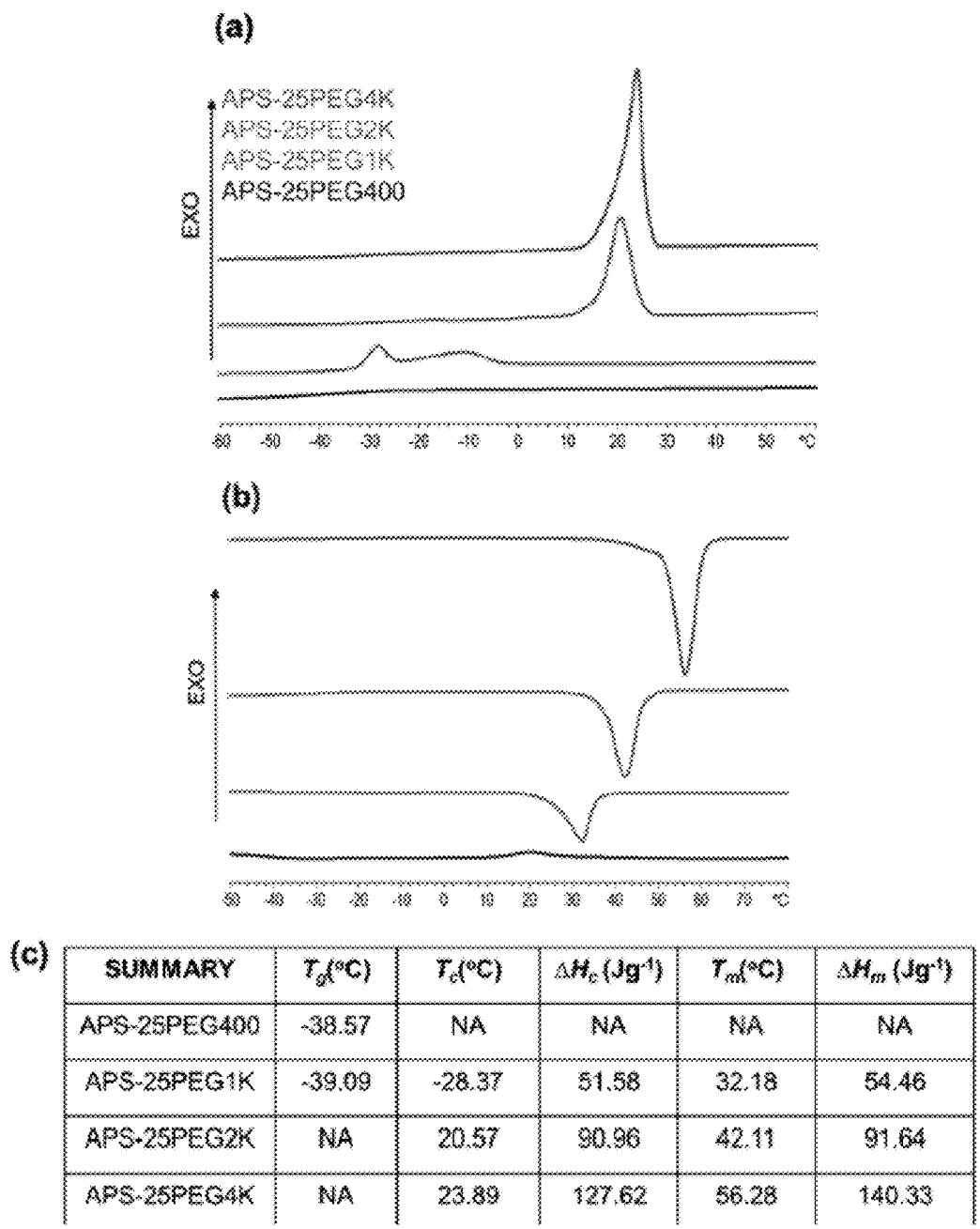
FIG. 6. Effect of PEG molecular weight on the thermal properties of APS-co-PEG pre-polymers (a) DSC curves of the cooling cycle (2nd) and (b) the heating cycle (3rd) of APS-co-PEG pre-polymers (top to bottom in (a) and (b): APS-25PEG4K, APS-25PEG2K, APS-25PEG1K, and APS-25PEG400), (c) Summary of the thermal properties of APS-co-PEG pre-polymers with varying PEG molecular weight (400-4000 Da).

The effect of PEG molecular weight on the thermal properties of APS-co-PEG pre-polymers with 25 mole % PEG is summarized in FIG. 6. APS-25PEG400, which has the lowest PEG $M_n$ (400 Da), did not show melting/crystallization peaks. Increasing PEG $M_n$ to 1000 Da, 2000 Da, and 4000 Da resulted in a dramatic shift in crystallization peaks to higher temperatures of −28.37, 20.57 and 23.89° C., respectively with simultaneous increase in DHc. A similar effect was observed for Tm and DHm (FIG. 6 (b) and (c)). In summary, addition of PEG (at high mole % or higher $M_n$) resulted in increased crystallinity of the copolymer thereby increasing crystallization enthalpies (FIGS. 5(c) and 6(c)). A similar trend was observed DHm also suggesting an increased mobility of copolymer chains in the presence of PEG.

Chemical Characterization of APS-Co-PEG Films.

The synthesized APS-co-PEG pre-polymers were subsequently fabricated into elastomer films by thermal crosslinking. In this study, pre-polymers were thermally cured under vacuum for 24 h to 72 h. Unfortunately, APS-co-PEG pre-polymers containing longer PEG chains (APS-25PEG2K and APS-25PEG4K) cannot be fabricated into polymer films even after 96 h of curing at a temperature of 170° C. It suggests that longer PEG chains may have impeded crosslinking between hydroxyl and carboxylic groups due to steric hindrance created by the long polyether chains. This problem could potentially be overcome by increasing the mole fraction of G or DAHP. All other APS-co-PEG pre-polymer series, once cured, could not be dissolved in any solvents and did not flow upon heating, indicating successful thermal crosslinking. The crosslinking process was also confirmed by comparing the FTIR spectra of the pre-polymer and cured film samples. Of note, the intensity ratios of the amide I to carbonyl peak of ester bond (1646/1730 $cm^{-1}$) and amide II to carbonyl peak (1552/1730 $cm^{-1}$) were lower in spectrum of cured elastomer than those of the pre-polymers (FIG. 7), indicating formation of new ester bonds in cured elastomer during the process of crosslinking as reported for cured APS films (C. J. Bettinger, et al., Biomaterials 29 (15) (2008) 2315-2325).

Mechanical Properties of APS-Co-PEG Films—

It is important that the APS-co-PEG polymer films maintain their elastomeric properties after PEG incorporation for their application in soft tissue engineering. It is also envisioned that different PEG ratios could widely tune the mechanical properties to broaden the narrow property spectrum of APS. Monomer feeding ratio, curing time, and curing temperature all play a role in determining the mechanical properties of polymeric materials. APSco-PEG pre-polymers could not be crosslinked at temperatures lower than 170° C., hence the curing temperature was fixed at 170° C. Hence, we explored (1) curing time; (2) PEG mole % and molecular weight; and (3) monomer feeding ratio to tune the mechanical properties of APS-co-PEG pre-polymers. It was found that APS-25PEG400 and APS-15PEG1K could be crosslinked within 24 h, while APS-25PEG1K and APS-40PEG1K required 48 h and 72 h for thermal curing, respectively. Thus, prepolymers with higher PEG mole % required a longer time for thermal crosslinking. This may suggest that longer PEG segments in the pre-polymer interfere with the crosslinking mechanism due to increased steric hindrance. These data are also in accordance with our observation that pre-polymers with higher molecular weight (PEG 2K and 4K) could not be crosslinked even after 96 h of thermal curing.

Figure 7:
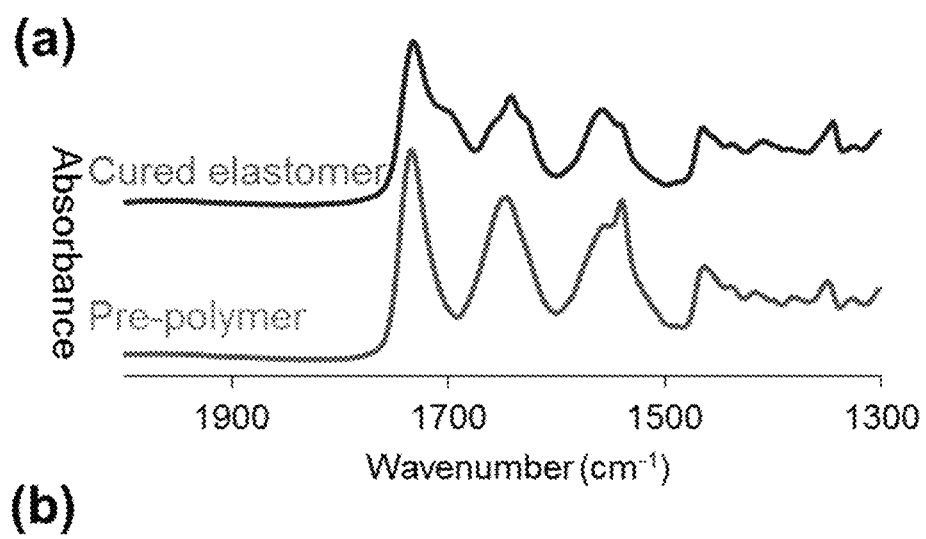
FIG. 7 (a) FTIR spectra of APS-15PEG1K pre-polymer and cured elastomer. (b) Intensity ratio of amide:ester peaks for APS-15PEG1K before and after thermal curing.

The effect of curing time on the mechanical properties of the polymer films is summarized in FIG. 7(*a*)-(*d*). APS-15PEG1K exhibited different mechanical properties after curing at 12, 48, or 72 h. The crosslinking density increased with curing time, which resulted in a significant increase in UTS (from 0.17 to 1.21 MPa) and elastic modulus (from 0.05 to 2.26 MPa), while elongation was reduced significantly from 338% to 123% ($p<0.05$, One-way ANOVA). Importantly, by only changing the curing time of the same pre-polymer, we were able to tune more than a 6-fold difference in UTS and 40 fold differences in elastic modulus. Similar trends of mechanical properties were also observed in APS-25PEG1K that was cured for 48 h and 72 h (Table 5).

Figure 8A:
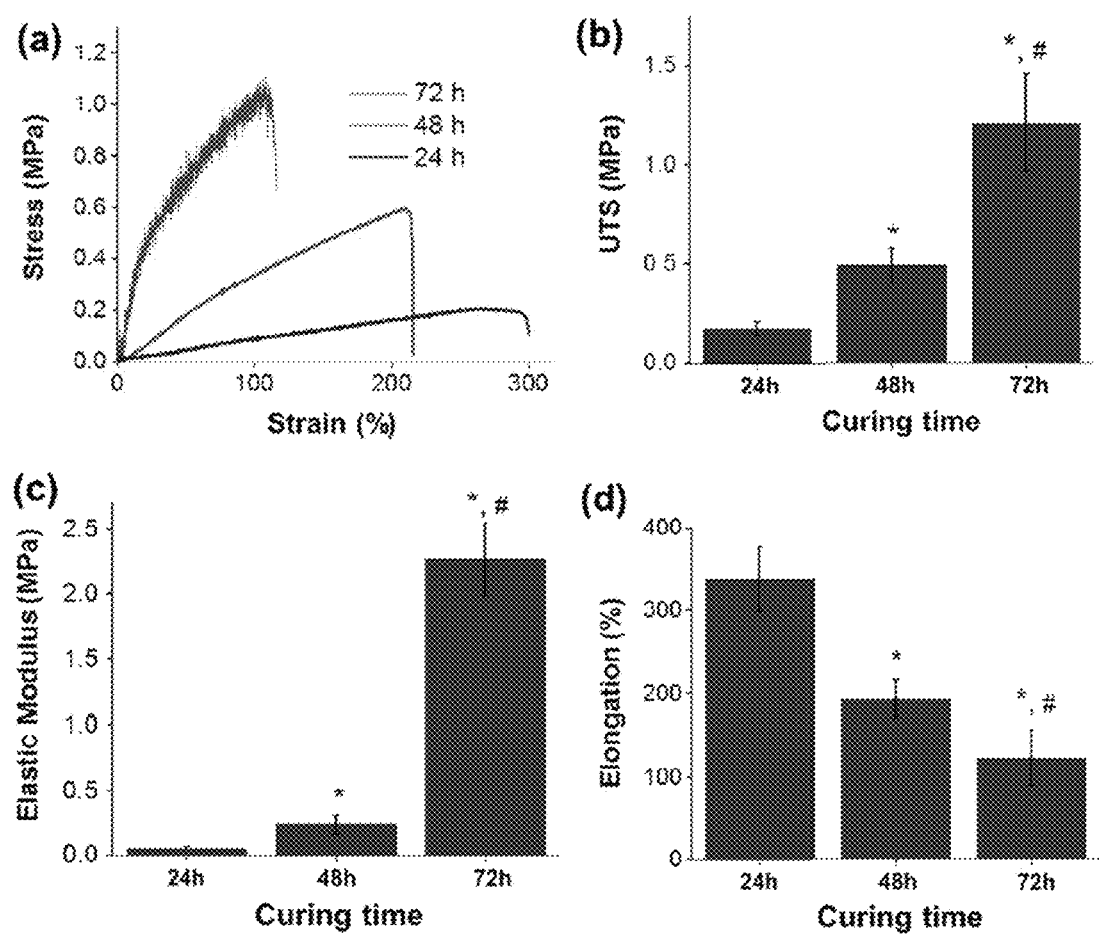
FIGS. 8A-8C. (a)-(d) Effect of curing time (24, 48 and 72 h) on a) Stress-strain curve; b) Ultimate tensile strength (UTS); c) Elastic modulus; and d) % elongation of APS-15PEG1K copolymer films (n=4). Significant differences at p<0.05 (*) compared to 24 h curing and (#) compared to 48 h curing. (e)-(h) Effect of chemical composition on: e) Stress-strain curve; f) Ultimate tensile strength (UTS); g) Elastic modulus; h) Percentage elongation of APS-co-PEG polymer films (n=4); i) Summary of the mechanical properties of PGS4 (top bar), PGS-co-PEG33 (second bar from top), AP523 (third bar from top), and APS-co-PEG (bottom bar). All films were thermally cured for 72 h. Significant differences at p<0.05 (*) compared to APS, (#) compared to APS-15PEG1K, (##) compared to APS-25PEG400, (@) compared to APS-25PEG1K, ($) compared to APS-40PEG1K, One-way ANOVA, Tukey post-hoc analysis.
Figure 8B:
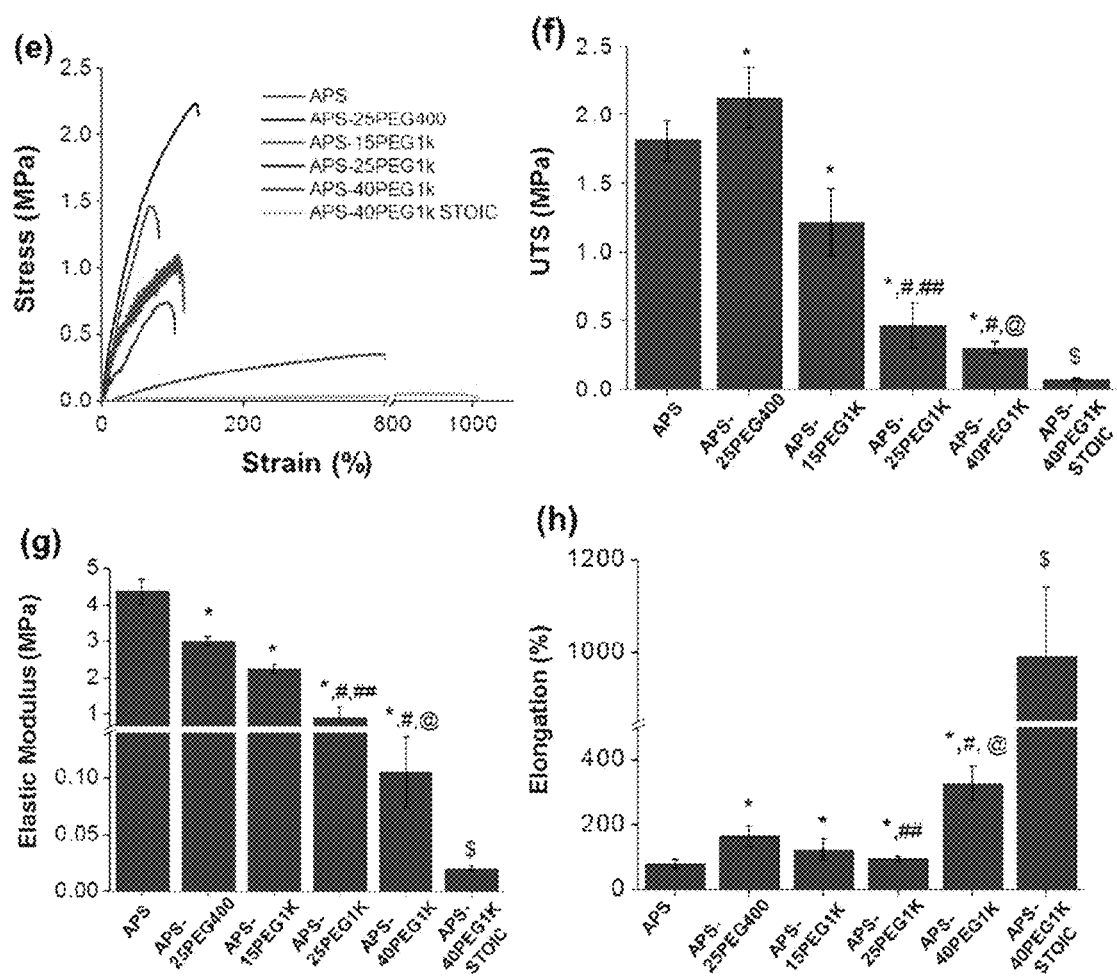
Figure 8C:
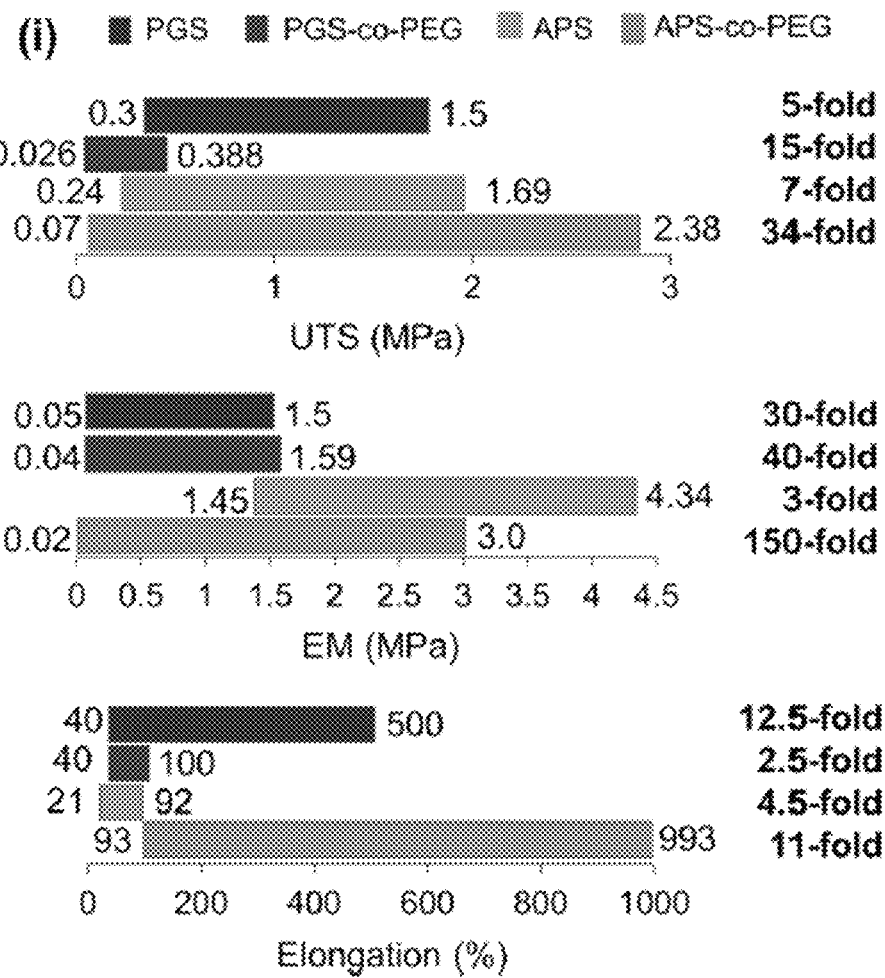

The effect of PEG content and monomer feeding ratio on the mechanical properties of the polymer films are summarized in FIG. 8 (*e*)-(*h*). Here, curing time for each copolymer film was fixed at 72 h to ensure direct comparison of different APS-co-PEG elastomers. The increase in PEG mole % from 15% to 40% resulted in the significant reduction in UTS (from 1.21 MPa to 0.30 MPa) and elastic modulus (from 2.26 MPa to 0.11 MPa) ($p<0.05$, One-way ANOVA). This also led to significant increase in elongation (123-326%) ($p<0.05$, One-way ANOVA) suggesting the formation of more elastic and ductile films. The effect of PEG molecular weight on the mechanical properties of the films was assessed by comparing APS-25PEG400 with APS-25PEG1K. APS-25PEG400 exhibited significantly higher UTS, elastic modulus, and elongation ($p<0.05$, Student's paired t-test). As the presence of higher molecular weight PEG segments in APS-25PEG1K increased its degree of crystallization (FIG. 6), it was expected that the corresponding films should be stronger and stiffer than low molecular weight PEG containing pre-polymer (APS-25PEG400). However, opposite trends were observed. These results could be explained based on the reduced crosslinking density. It is noteworthy to mention that presence of higher mole % or molecular weight of PEG segments interfered with the crosslinking of thermally cured films, leading to reduced crosslinking density at the same thermal curing condition. This result was in accordance with our observation that APS-25PEG2K and APS-25PEG4K cannot be cured due to the steric hindrance of increased PEG segments posed on the crosslinking process.

The effect of monomer feed ratio on the mechanical properties of the films was assessed by comparing APS-40PEG1K and APS-40PEG1K STOIC polymer. APS-40PEG1K STOIC exhibited significantly weaker mechanical properties as shown in Table 5 (4 fold reduction in UTS). This may be attributed to the reduced availability of free hydroxyl groups (of G and DAHP) for crosslinking, leading to a reduced crosslinking density and consequently, decreased UTS and elastic modulus, however remarkably higher extensibility (more than 1000%) ($p<0.05$, Student's paired t-test). When compared to the mechanical properties of existing elastomers, APS-40PEG1K STOIC is among the most elastic ones, with a similar elastic modulus ($0.02\pm0.002$ MPa) to that of human smooth muscle. However, its weak mechanical strength may limit its biomedical application.

In summary, these results demonstrate that the mechanical properties of APS-co-PEG elastomers could be carefully tuned by varying curing time, PEG ratio as well as monomer feeding ratio. APS-co-PEG expanded the mechanical properties of APS by increasing UTS, reducing elastic modulus and increasing elongation. APS-co-PEG polymers possessed

TABLE 5

Summary of the mechanical properties of thermally cured APS-co-PEG polymer films (n = 4)

|   | APS-15PEG1K 24 h | APS-15PEG1K 48 h | APS-15PEG1K 72 h | APS-25PEG1K 48 h | APS-25PEG1K 72 h | APS-25PEG400 72 h | APS-40PEG1K 72 h | APS-40PEG1K 72 h Stoic |
|---|---|---|---|---|---|---|---|---|
| UTS (MPa) | 0.17 ± 0.03 | 0.49 ± 0.09 | 1.21 ± 0.24 | 0.13 ± 0.02 | 0.46 ± 0.17 | 2.12 ± 0.22 | 0.30 ± 0.04 | 0.07 ± 0.008 |
| Elastic Modulus (MPa) | 0.05 ± 0.01 | 0.24 ± 0.07 | 2.26 ± 0.28 | 0.10 ± 0.01 | 0.9 ± 0.24 | 3.01 ± 0.12 | 0.11 ± 0.03 | 0.02 ± 0.002 |
| Elongation at break (%) | 338 ± 39 | 193 ± 24 | 123 ± 33 | 317 ± 74 | 93 ± 9 | 165 ± 32 | 326 ± 52 | 993 ± 149 | much wider range of mechanical properties compared to the existing thermoset elastomers such as PGS (Q. Z. Chen, et al. Elastomeric biomaterials for tissue engineering, Prog. Polym. Sci. 38 (3-4) (2013) 584-671), APS (C. J. Bettinger, et al. Amino alcohol-based degradable poly(ester amide) elastomers, Biomaterials 29 (15) (2008) 2315-2325) and PGS-co-PEG (A. Patel, et al. Highly elastomeric poly(glycerol sebacate)-co-poly(ethylene glycol) amphiphilic block copolymers, Biomaterials 34 (16) (2013) 3970-3983) (FIG. 8(i)) as evident from the comparative fold change (highest/lowest values). For example, APS-co-PEG series of elastomers offer 150-fold change in elastic modulus compared to only 40-fold change for PGS-co-PEG series. Similarly, UTS values for APS-co-PEG series showed 34-fold change vs only 14.9-fold change for PGS-co-PEG series. Such wide range of mechanical properties of APS-co-PEG elastomers and ability to further fine-tune them by changing crosslinking time, PEG amount or Mn will be useful in many applications in tissue engineering.

Hydration Properties and Physiological Degradability—

Figure 9:
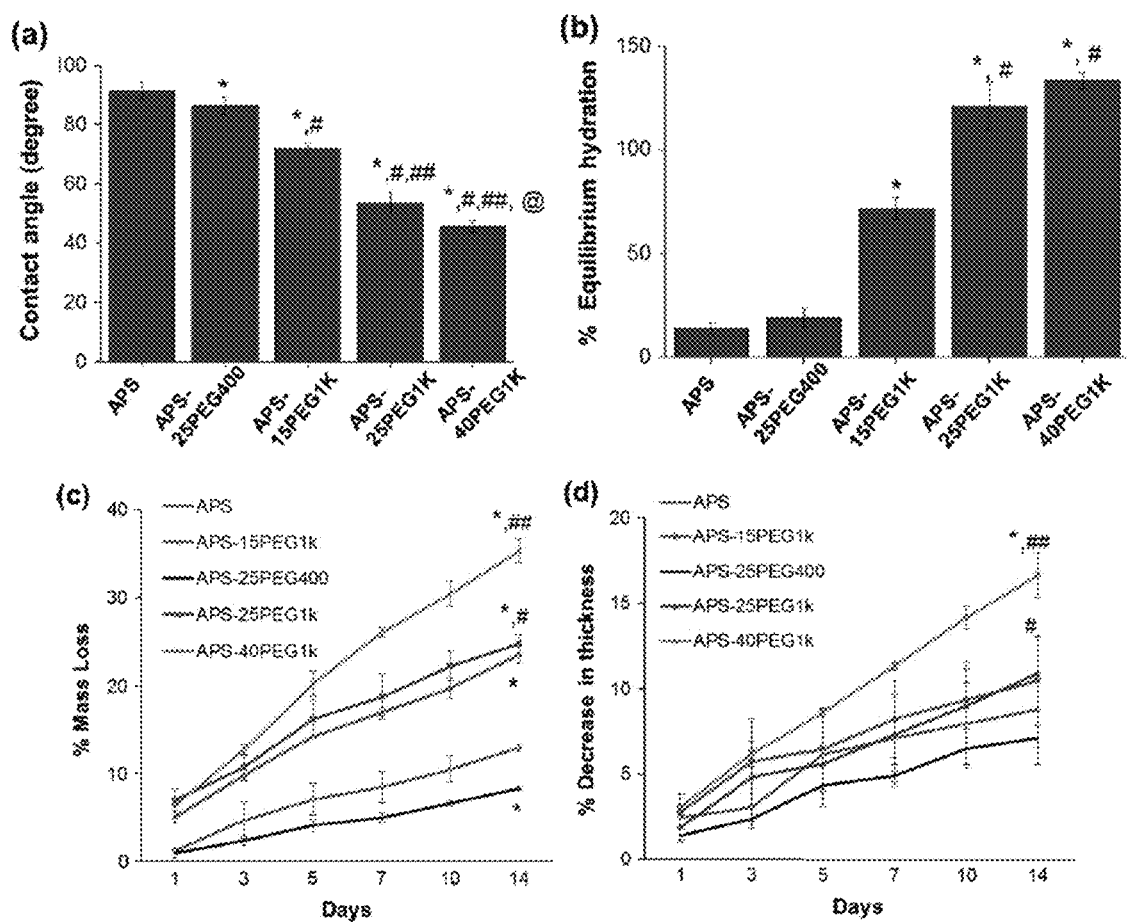
FIG. 9. a) Water in air contact angle measurement of APS and APS-co-PEG polymer films (n=4). Significant differences at p<0.05 (*) compared to APS, (#) compared to APS-25PEG400, (##) compared to APS-15PEG1K, (@) compared to APS-25PEG1K. b) Equilibrium hydration of APS and APS-co-PEG polymer films in DPBS (n=3). Significant differences at p<0.05 (*) compared to APS and (#) compared to APS-15PEG1K. c) The percent mass loss of APS and APS-co-PEG polymer films in DPBS after equilibrium hydration was reached (n=3). d) The percent decrease in thickness of APS and APS-co-PEG polymer films in DPBS after equilibrium hydration was reached (n=3). Significant differences at p<0.05 (*) compared to APS, (#) compared to APS-25PEG400, (##) compared to APS-15PEG1K, One-way ANOVA, Tukey post-hoc analysis.

Hydration and degradation studies were carried out on copolymer films cured for 72 h. Hydration is an important factor for tissue engineering applications because it influences the mechanical properties, diffusion properties, and degradation rate of the scaffolds in vivo. To assess the hydrophilicity of crosslinked polymer films, the water-in-air contact angle of the copolymer films fabricated from different pre-polymers was measured. Increase in amount or molecular weight of PEG in the copolymer chain exhibited significant decrease in contact angles (p<0.05, One-way ANOVA) due to the increase in hydrophilicity of the APS-co-PEG polymers (FIG. 9(a)). Hydration of the APS-co-PEG films was then investigated by monitoring the water uptake capacity. The swelling study under physiological conditions (DPBS, pH 7.4) revealed that APS-25PEG400 and APS-15PEG1K reached the equilibrium hydration on day 1, while copolymers containing higher PEG content (APS-25PEG1K and APS-40PEG1K) reached the equilibrium hydration on day 2. These data imply that increased amount of PEG chains in the copolymer films leads to delayed equilibrium hydration. It is possible that different crosslinking densities of APS-co-PEG may influence the kinetics of hydration. There was almost a 10-fold difference in equilibrium hydration between APS (14.0±2.3%) and APS-40PEG1K (133.5±3.7%) elastomer films (p<0.05, One-way ANOVA) (FIG. 9 (b)). A high water uptake within a tissue-engineered scaffold promotes the mechanical deformation with minimum hysteresis under dynamic in vivo conditions. Therefore, PEG incorporation enables the tuning of hydration properties.

The degradation study was conducted after each polymer film reached equilibrium hydration. On day 14 after equilibrium hydration, APS, APS-25PEG400, APS-15PEG1K, APS-25PEG1K, and APS-40PEG1K polymer films exhibited 12.93±0.5%, 8.33±0.2%, 23.5±1.0%, 24.7±1.0% and 35.2±1.3% of mass loss, respectively (FIG. 9(c)). The increase in degradation rate with the PEG molar ratio was due to the increased hydrophilicity of polymer network, resulting in higher water uptake (FIGS. 9 (a), (b)) and thus, accelerating the rate of hydrolysis. Diffusion of water into polymer chains is also determined by Tg of the polymer. In general, lower Tg leads to higher rate of water diffusion in the bulk. As shown in FIGS. 5 and 6, incorporation of PEG in the copolymers decreased their glass transition temperature from 5.98° C. (APS) to below −30° C. for APS-co-PEG polymers, thus enhancing their water uptake capacity and degradation except in APS-25PEG400. The results are consistent with previous results reported for the degradation of PEGylated elastomer (A. Patel, et al. Highly elastomeric poly(glycerol sebacate)-co-poly(ethylene glycol) amphiphilic block copolymers, Biomaterials 34 (16) (2013) 3970-3983). However, APS-25PEG400 showed slower degradation than APS and other APS-co-PEG elastomers (FIG. 9 (c)) despite of similar water uptake to that of APS, suggesting minor role of water uptake in its degradation. Further, addition of PEG may increase the crystallinity of the polymer structure and therefore, slow down the degradation rates. However, we did not observe any cold crystallization peak in the DSC of APS-25PEG400, ruling out that possibility. Thus, slower degradation observed for APS-25PEG400 cannot be explained in these studies.

Figure 10:
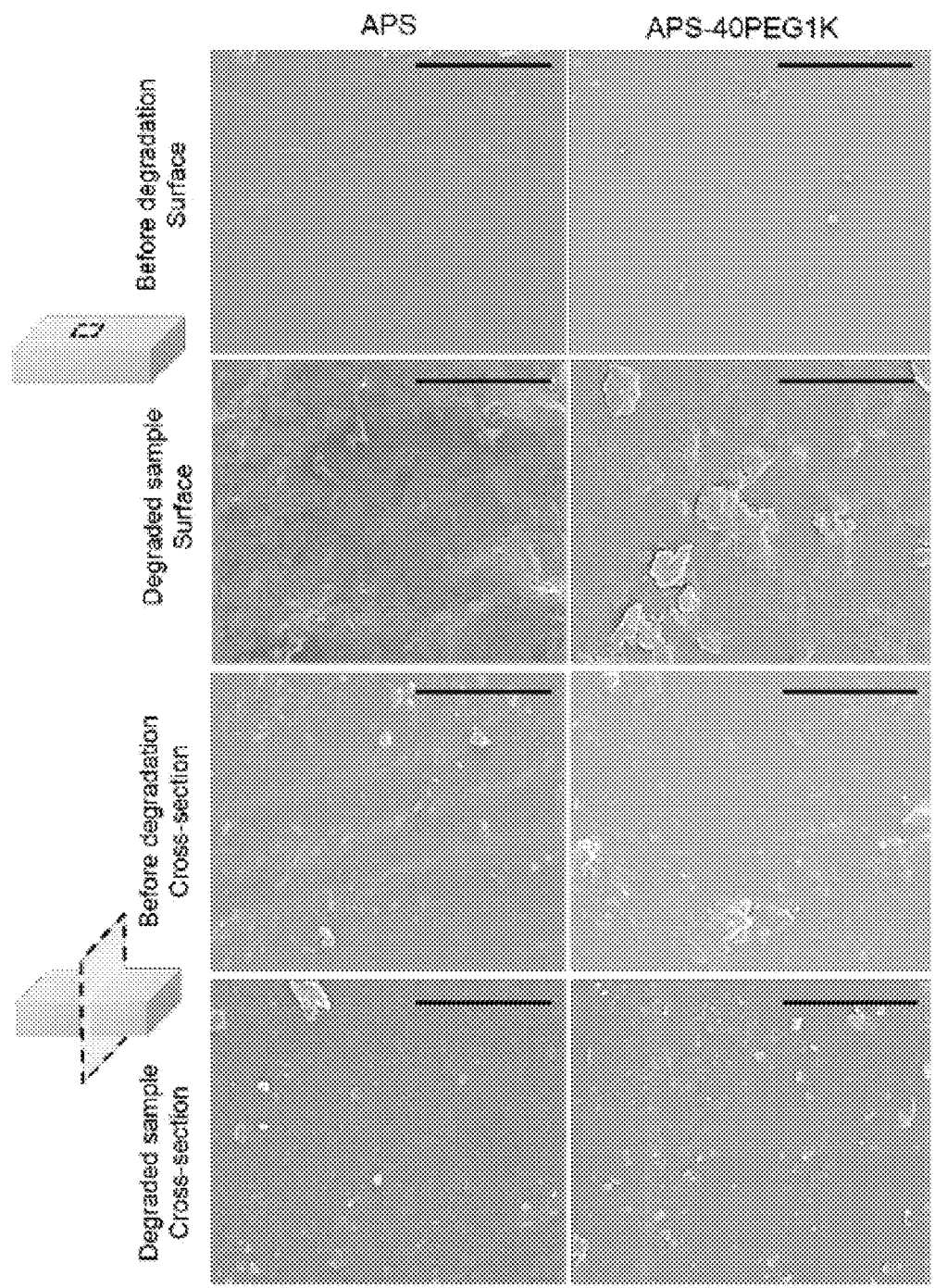
FIG. 10. SEM images of APS and APS-40PEG1K copolymer films before and after 14 days degradation in PBS showing morphology of the surface and cross-section of the films. Scale bars represent 10 µm in all images.

During degradation, there was a gradual decrease in thickness along with the mass loss in each polymer film. The percentage decrease in thickness on day 14 for APS, APS-25PEG400, APS-15PEG1K, APS-25PEG1K, and APS-40PEG1K polymer films were 8.8±2.2%, 7.13±1.5%, 10.5±2.6%, 10.9±2.1%, and 16.6±2.3%, respectively FIG. 9(d)). Almost constant rates of mass loss and linear decreases in the film thickness were observed in all series of APS-co-PEG elastomers. This suggested that the degradation of APS-co-PEG films was probably via the surface erosion mechanism. Ideally, the degradation mechanism should be further confirmed by examining the change in molecular weight of the sample during degradation. However, since APS and APS-co-PEG elastomers are thermoset elastomers, it is difficult to measure their molecular weight once they are crosslinked. Instead, the morphology of as-prepared and degraded samples were compared by SEM (FIG. 10). APS-40PEG1K, which exhibited the highest rate of degradation after 14 days, was further characterized for change in film morphology after degradation. Both APS and APS-40PEG1K samples before degradation showed almost smooth surface, while the roughness of film surface increased in degraded films.

Figure 11A:
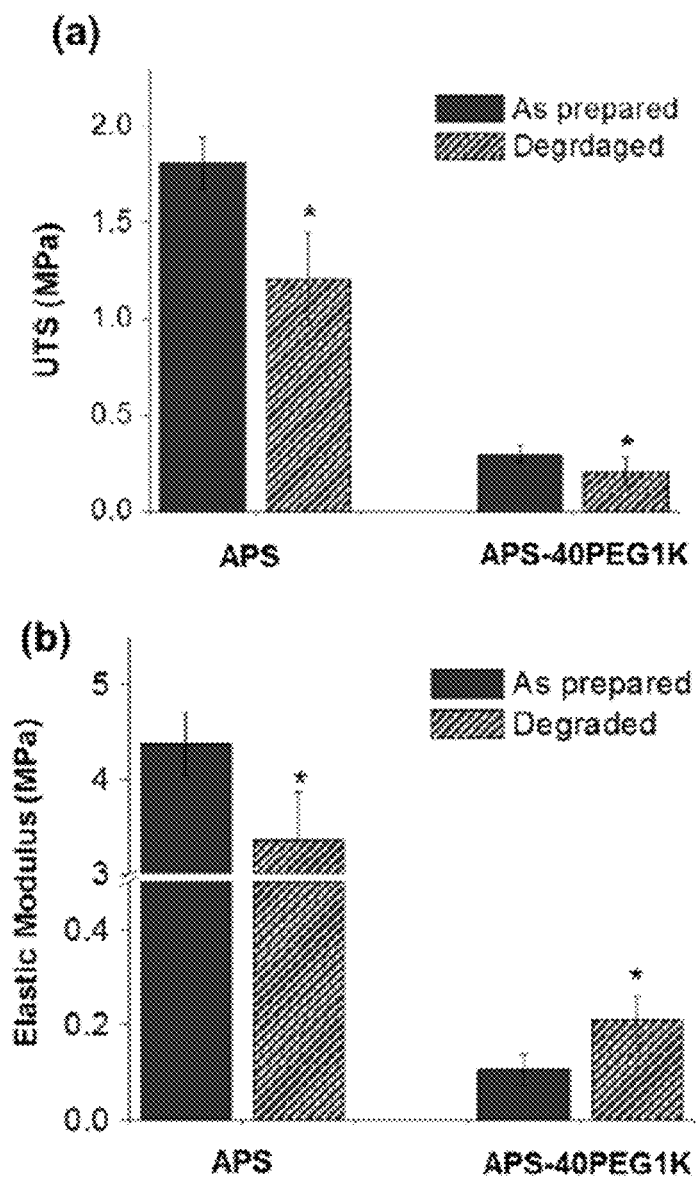
FIGS. 11A and 11B. (a)-(c) Effect of degradation on a) UTS, b) Elastic modulus, and c) % Elongation of APS and APS-40PEG1K copolymer films after 14 days degradation in PBS (n=3). p<0.05 (*) compared to as prepared samples, Student's paired t-test. d) FTIR spectra of APS and APS-40PEG1K cured polymer films before and after 14 days degradation in PBS, showing decrease in the intensity of PEG peaks and increased intensity ratio of amide:ester peaks (table) suggesting selective hydrolysis of ester bonds and preferential loss of PEG chains.

Of note, no pores or cracks were observed on the surfaces of degraded samples. Cross-section of both degraded APS and APS-40PEG1K films showed morphology similar to that of films before degradation, indicating that the central portion of the films had little or no degradation. High magnification SEM images suggested that APS-40PEG1K films might have degraded via surface erosion. Previous degradation study of PLGA, a representative thermoplastic polymer, exhibited bulk degradation, accompanying surface fracture and pore formation, a hallmark of heterogeneous degradation (C. J. Bettinger, et al., In vitro and in vivo degradation of poly(1,3-diamino-2-hydroxypropane-co-polyol sebacate) elastomers, J. Biomed. Mater. Res. A 91A (4) (2009) 1077-1088). Such degradation mechanism is usually not favored as it results in sudden and drastic change in mechanical properties during degradation, leading to mechanical failure of the scaffold. On the contrary, elastomers degraded by surface erosion are expected to exhibit gradual change in the mechanical properties due to their homogeneous surface degradation and a constant rate of mass loss, as observed in case of APS-co-PEG elastomers (FIG. 9(c), (d) and 10). Thus, mechanical properties of degraded APS and APS-40PEG1K were measured to determine the effect of degradation. APS showed almost 30% decrease in UTS after about 13% mass loss. On the other hand, APS-40PEG1K showed similar decrease in UTS even after three-fold higher (35.2±1.3%) mass loss (FIG. 11(a)). Interestingly, APS-40PEG1K exhibited increased elastic modulus after degradation (FIG. 11 (b)), which was probably due to the preferential loss of the amorphous region compared to crystalline domains. Both APS and APS-40PEG1K elastomers exhibited reduced elongation after degradation (FIG. 11 (c)). APS-co-PEG elastomers demonstrated gradual change in mechanical strength and elastic modulus after degradation, which shows their important advantage over classical polyesters such as PCL, PLGA and their copolymers since these polyesters exhibit large discrepancy in their mechanical properties in dry and wet conditions. It is suggested that this may be one of the reasons for the mechanical failure of these classical polyesters in vivo (H. K. Makadia, et al., Poly lactic-co-glycolic acid (PLGA) as biodegradable controlled drug delivery carrier, Polymers 3 (4) (2011) 1377-1397).

Further, FTIR studies were performed on the degraded samples (FIG. 11(d)) in order to determine the functional groups of copolymer films susceptible to hydrolysis during degradation. In the FTIR spectra of APS-40PEG1K after degradation, a marked increase in the intensity ratios of the amide I to carbonyl peaks of ester bond (1646/1730 $cm^{-1}$) was observed.

Figure 11B:
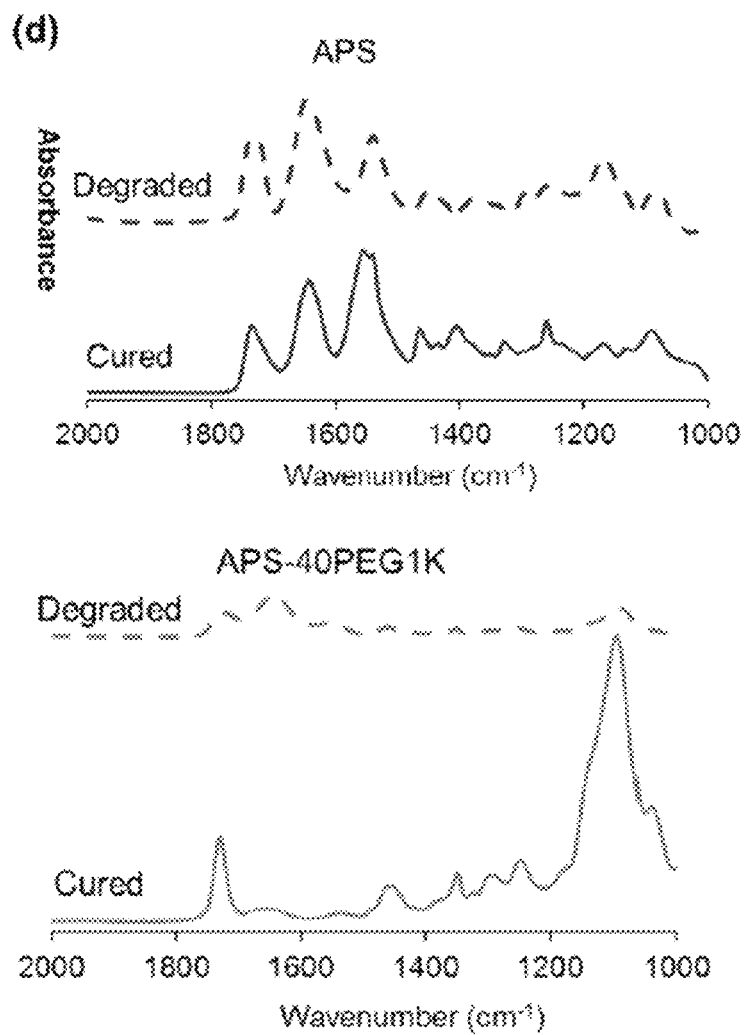

Additionally, by comparing the spectra of APS-40PEG1K before and after degradation, a marked reduction in intensity of C—O—C stretching peak (1110 $cm^{-1}$) and C—H bending peaks (1464 and 1343 $cm^{-1}$) of PEG was noted (FIG. 11 (d)). Taken together, these data indicated that APS-co-PEG copolymers degrade by preferential hydrolysis of ester bonds over amide bonds, resulting in faster loss of PEG segments, confirming the increased elastic modulus after degradation.

Overall, the preliminary degradation study demonstrated the ability to tune the degradation rates of APS-co-PEG elastomers over a wider range. Of note, the degradation of APS-40PEG1K is via surface erosion and preferential hydrolysis at the ester bonds in the APS-co-PEG backbone. The degradation of other APS-co-PEG elastomers needs to be studied individually and complete degradation study such as enzymatic degradation over longer periods of time in vitro and in vivo is required for the determination of suitable applications for this novel class of elastomers.

Cell Attachment and Viability—

Figure 12:
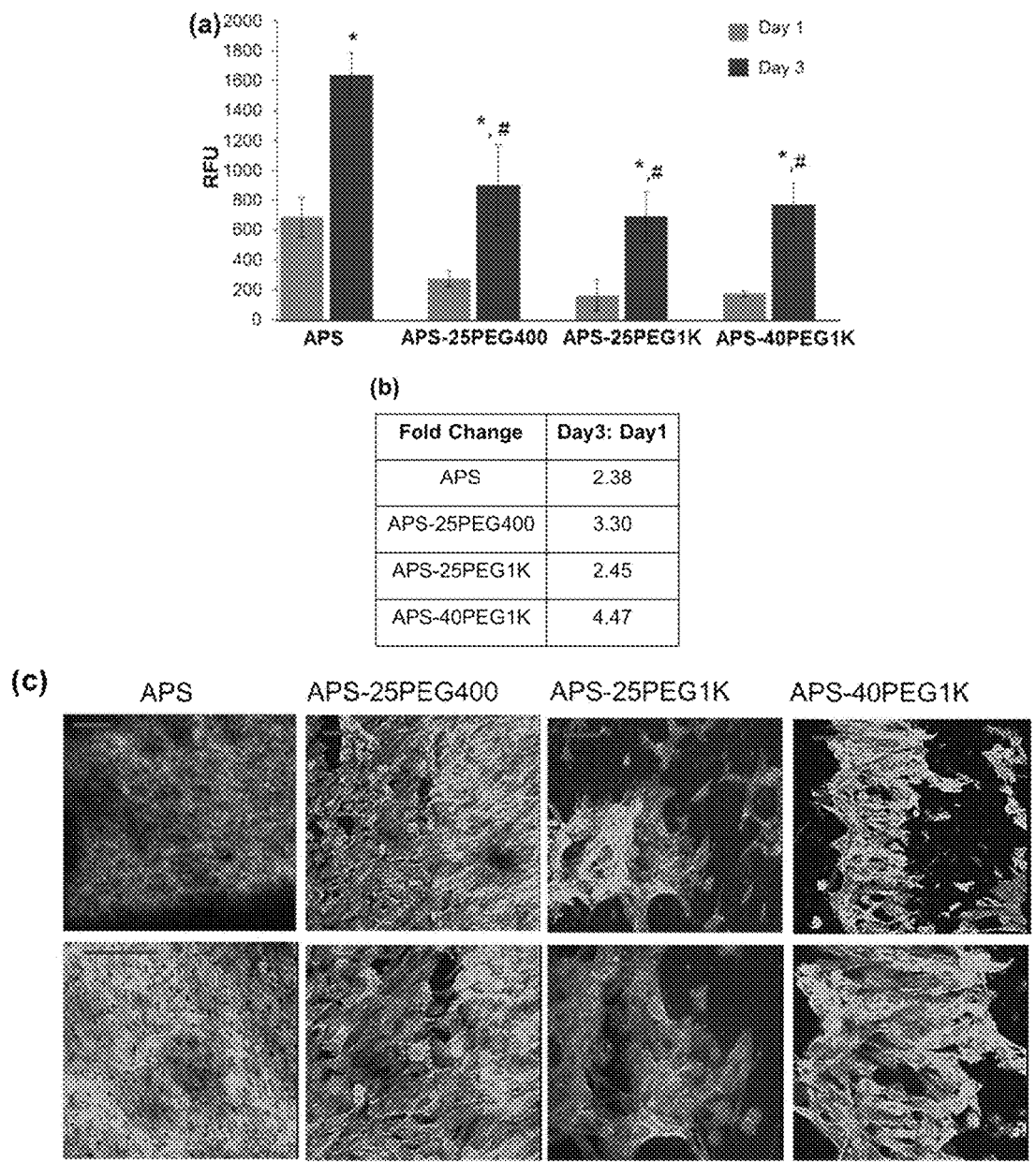
FIG. 12. (a) Metabolic activity (AlamarBlue®) of C2C12 cells on APS and APS-co-PEG films showing increased cell proliferation over 3 days on all films. (N=3) p<0.05 (*) compared to day 1 readings in each group, (#) compared to APS day 3 reading. (b) C2C12 cells on APS and APS-co-PEG films showing spreading cell morphology at day 3. Cells were fixed and actin cytoskeleton was stained with ActinGreen (green) and nuclei were stained with NucBlue (blue). Scale bars represent 100 µm in all images.

The biocompatibility of APS-co-PEG elastomers was studied by examining the cellular activities of C2C12 cells seeded on APS and APS-co-PEG elastomer films (FIG. 12). One of the most prominent properties of biodegradable elastomers is that they can withstand the dynamic stretch and relax without the mechanical failure. This property is useful for tissue engineering applications, particularly for soft tissues like skeletal muscle. APS/PCL electrospun scaffold is a promising candidate for skeletal muscle tissue engineering. C2C12 cell line is one of the widely used cell lines for the regeneration of skeletal muscle. Therefore, C2C12 cell line is chosen as the model cell line to examine the biocompatibility of APS-co-PEG. Since films were transferred to the new wells 24 h after initial seeding, cell metabolic activities measured by AlamarBlue® assay on day 1 reflect the initial cell attachment to the films. AlamarBlue® fluorescence reading on day 1 suggested that the attachment of C2C12 cells on APS-co-PEG films was lower than APS film (FIG. 12 (a)), which may be due to reduced cell adhesion on the film surface in the presence of hydrophilic PEG segments. However, cells cultured on all films exhibited significant increase ($p<0.05$) in metabolic activities on day 3 as compared to day 1 (FIG. 12 (a)). This suggests that once cells are attached to the films, the presence of PEG did not affect cell proliferation. The increase of PEG molecular weight or molar ratio did not significantly affect cell proliferation. Of note, cells seeded on APS-co-PEG films exhibited higher proliferation rates than that of APS films as indicated by the larger fold increase of AlamarBlue® fluorescence reading between day 1 and day 3 (FIG. 12 (b)). In order to minimize the strong autofluorescence of APS and APS-co-PEG polymers while imaging, the films were stained with Sudan Black. On day 3, C2C12 cells cultured on APS and APS-co-PEG films exhibited similar cell spreading (FIG. 12 (c)). Cell morphology appears different for different polymers. This may be attributed to the differences in initial cell attachment and cell number. As shown in FIG. 12 (a), APS showed the highest metabolic activity and thus, cell number compared to PEGylated polymers on day 1 and 3 which is also evident in FIG. 12 (c), showing completely confluent cells on APS. On the other hand, APS-25PEG1K and APS-40PEG1K had less number of cells and hence, more available area for spreading, which may have resulted in the observed 'differences' in their morphology. These results suggest that APS-co-PEG elastomers support cell proliferation, and can potentially be used for tissue engineering applications.

In conclusion, a series of novel APS-co-PEG elastomers were synthesized by varying the molar percentage and molecular weight of PEG. The physicochemical, mechanical, and degradation properties could be tailored by altering the amount and molecular weight of PEG within the APS backbone. APS-co-PEG films showed increased hydrophilicity and wide range of mechanical and degradation properties. Importantly, APS-40PEG1K degraded by surface erosion with gradual change in mechanical properties during degradation. The incorporation of PEG reduced the initial attachment of C2C12 cells but supported cell growth and spreading. This study demonstrated that APS-co-PEG elastomers have broadened the property spectrum of currently available elastomers and allows fine-tuning of physicochemical, mechanical and degradation properties of tissue engineered scaffolds to match that of a wide range of tissues to facilitate their regeneration.

Example 2

Figure 13:
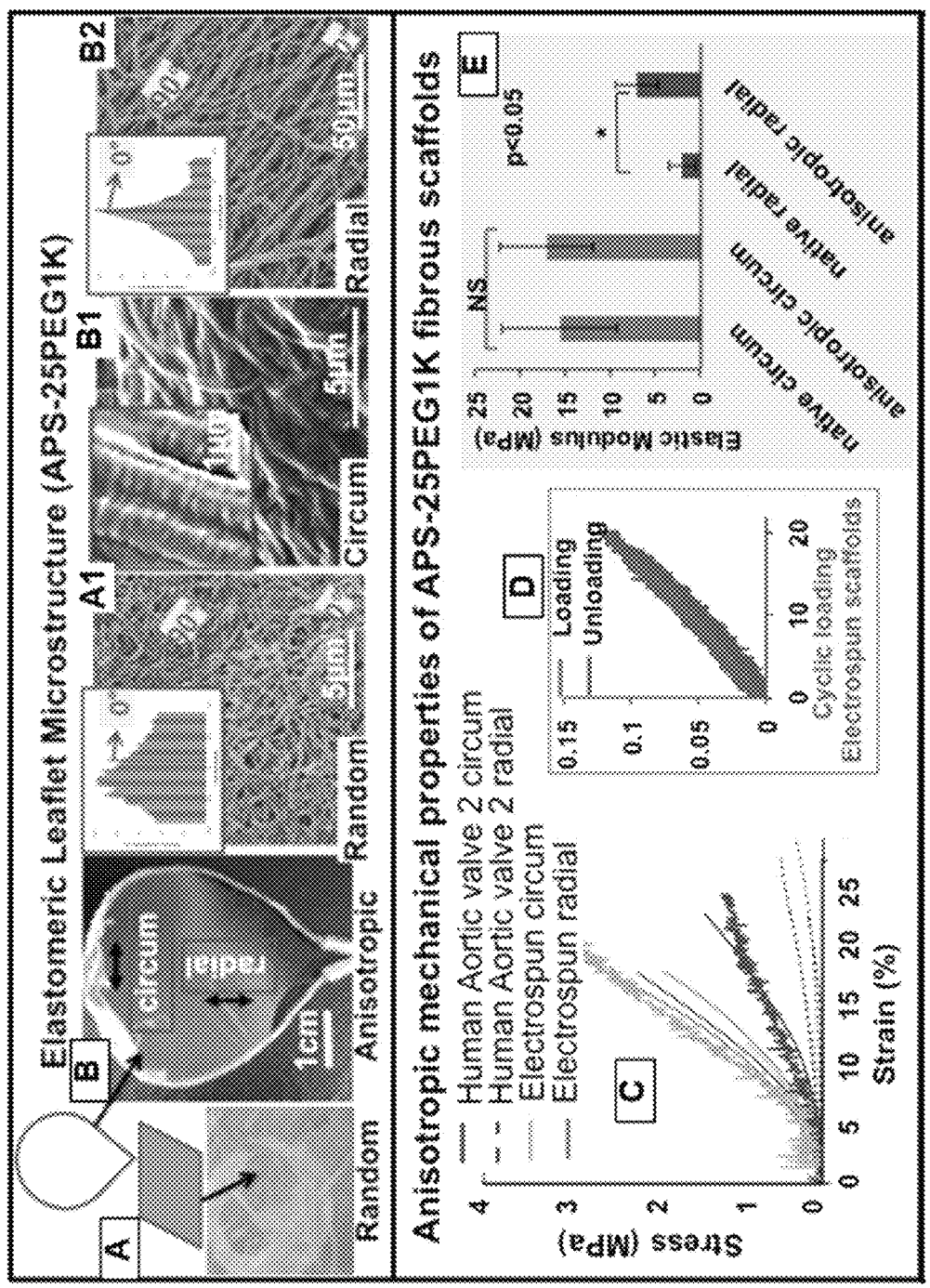
FIG. 13. A. Random and B. Anisotropic fibrous scaffolds prepared from APS-25PEG1K/PCL (80/20) collected on aluminum foil or leaflet-shaped collector showing random (A1), crimped collagen-like (B1 and inset) and radial elastin-like (B2) fibrous alignment. C. Stress-strain curves of APS-25PEG1K/PCL scaffolds collected on leaflet-shaped collector in circumferential (orange) and radial (purple) direction are compared with those of native aortic valves. D. Cyclic tensile testing (10 reproducible cycles of loading and unloading) on APS-25PEG1K/PCL scaffolds); E. APS-25PEG1K/PCL anisotropic scaffolds exhibit comparable Elastic moduli in circumferential direction but are much stiffer in radial direction.
Figure 14:
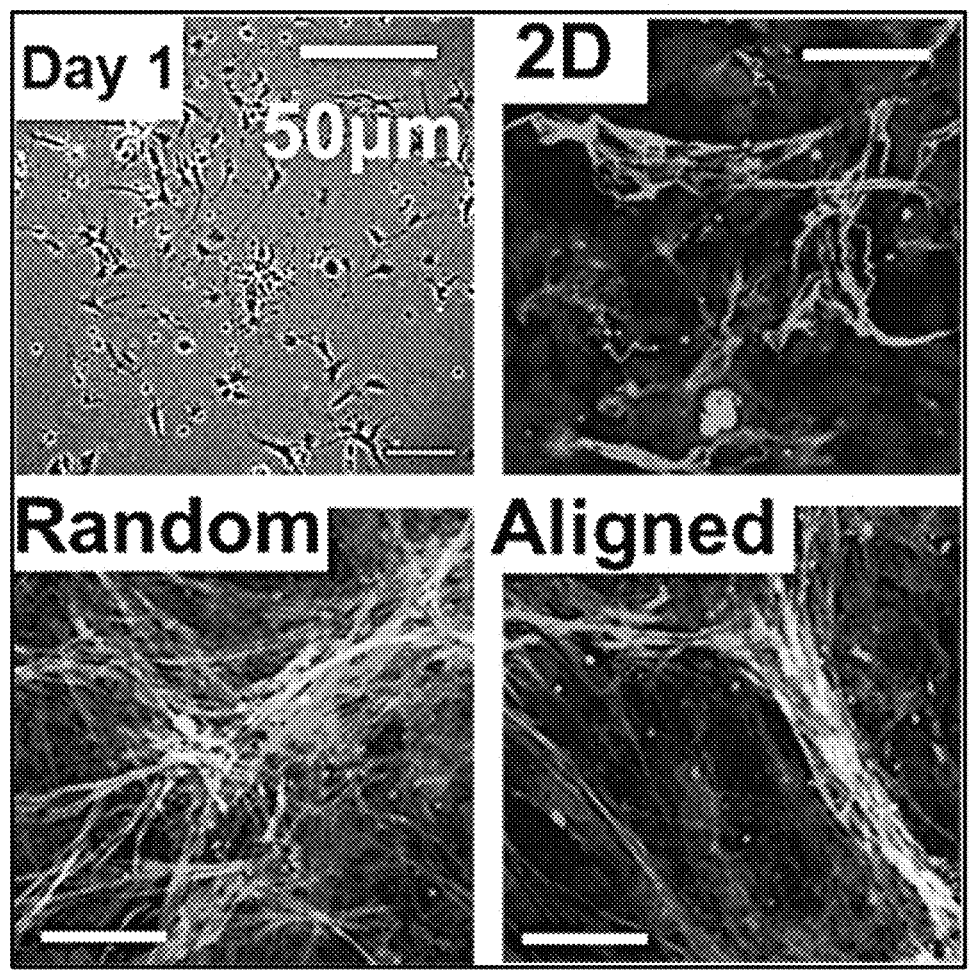
FIG. 14 are VICs isolated from an 80 year old ascending aortic aneurysm female patient were grown in 2D and on random and aligned scaffolds (250,000 cells/cm$^2$) for 4 days and stained with Hoechst (blue, nuclei), SMA (Red) and Actin (green). Scaffolds allow attachment/spreading of VICs with aligned fibers promoting alignment.

The applications of these materials in soft tissue engineering like cardiac patch, skeletal muscle, heart valve etc. is foreseen. These materials are currently being tested for scaffolds for valve leaflet tissue engineering. Anisotropic electrospun scaffolds are being developed using these materials. The following data supports this. FIG. 14 are VICs isolated from an 80 yr old ascending aortic aneurysm female patient were grown in 2D and on random and aligned scaffolds (250,000 cells/$cm^2$) for 4 days and stained with Hoechst (blue, nuclei), SMA (Red) and Actin (green). Scaffolds allow attachment/spreading of VICs with aligned fibers promoting alignment. The materials described herein are compatible with C2C12 myoblast cells (see Example 1), as well as with valvular interstitial cells (VICs), as shown in FIG. 14, seeded on random and aligned electrospun scaffolds as shown in FIG. 13.

Electrospun Fiber Fabrication:

Composite APS-PEG/PCL (1:1, w/w) fibrous scaffolds were fabricated using a conventional electrospinning setup interfaced with ring-like wire loop as collector. Important electrospinning parameters such as total polymer concentration, solvent, voltage, flow rate and distance of needle to collector were optimized to be 24% w/v, 9:1 (v/v) chloroform/ethanol, 16 kV, 1 ml/h and 6 cm, respectively. The obtained electrospun scaffolds were dried and then soaked in deionized water to allow for the removal of any sprayed polymer and remaining solvent.

SEM:

Scaffold morphology and porosity was characterized using scanning electron microscopy (SEM) (JEOL 6335F Field Emission SEM, Japan). Fibrous scaffolds were sputter-coated with 5 nm of gold-palladium using Cressington 108 auto sputter-coater (Cressington Scientific Instruments, UK) and images were obtained using accelerated voltage of 3 kV.

Uniaxial Mechanical Testing:

Scaffold mechanical properties were studied using uniaxial tensile tests with ADMET MTEST Quattro mechanical testing system (ADMET, Norwood, Mass.). Scaffolds were cut into rectangular shapes (15×6 mm$^2$, n=4 per group) from circumferential and radial direction and stretched until failure at a constant jogging speed of 10 mm/min. Ultimate tensile strength (UTS) and elastic modulus in the linear region at 5-15% strain were recorded for each scaffold tested.

Degradation:

In vitro degradation properties were studied by submerging whole scaffold samples in 10 mL PBS solution in 50 mL falcon tubes. Solutions were maintained in a shaking incubator at 37° C. and 50 rpm. At specific time points, scaffolds were subject to uniaxial mechanical testing.

Figure 15:
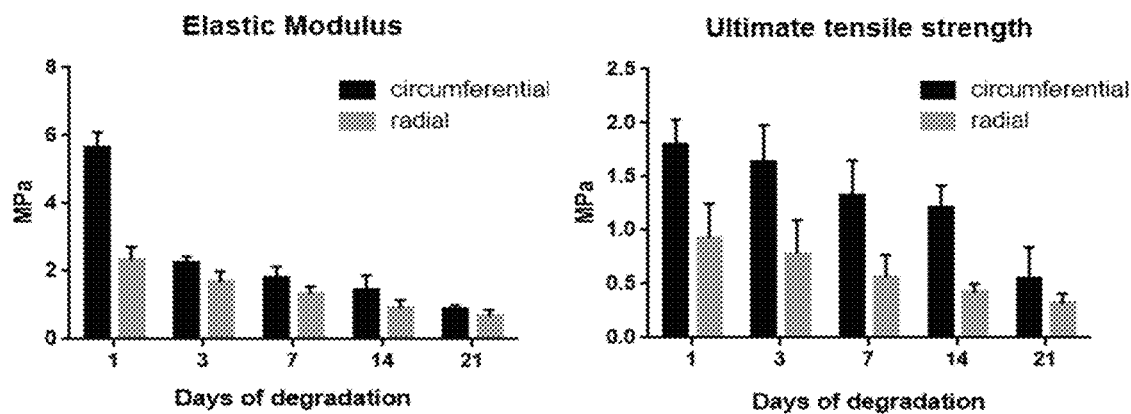
FIG. 15: Mechanical properties of anisotropic fibers during degradation in phosphate buffered saline.

Anisotropic heart valve leaflets were prepared using an elastomer as described herein. The anisotropic fibers exhibited significantly different mechanical properties (elastic modulus and ultimate tensile strength) during degradation test in phosphate buffered saline based on radial or circumferential fiber orientation as shown in FIG. 15.

Figure 16:
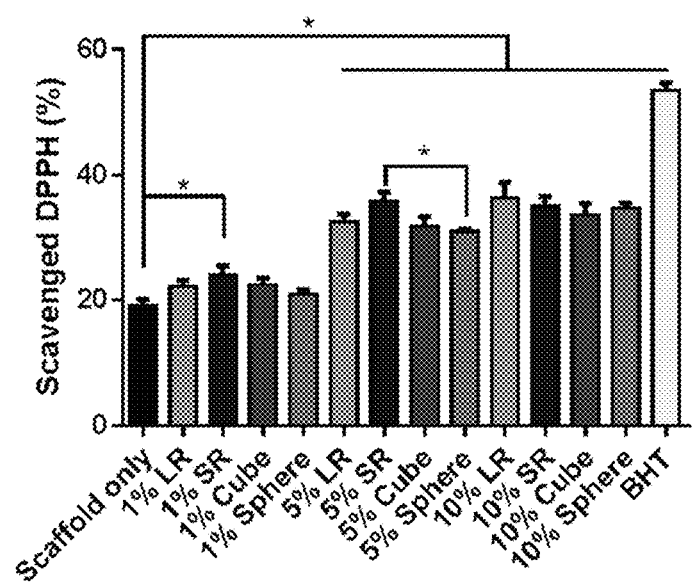
FIG. 16: Antioxidant activity of cerium nanoparticles (NPs) loaded APS-PCL elastomeric scaffolds using DPPH assay (LR: long rods of cerium NPs, SR: short rods of cerium NPs, cube: cube shaped cerium NPs, Spheres: Spherical cerium NPs).

Further, reactive oxygen species can be detrimental in tissue regeneration. To address this problem, we have incorporated cerium nanoparticles of different shapes (spheres, cubes, rods etc) were incorporated into these elastomeric fibers to exploit antioxidant properties of cerium in heart valve tissue engineering. The preliminary characterization of antioxidant activity using DPPH assay indicates increased antioxidant activity in scaffolds containing cerium nanoparticles as compared to control scaffolds as shown in FIG. 16. Butylated hydroxytoluene (BHT) is used as a positive control in these experiments.

Example 3—Semiquantitative FTIR Analysis

Thermoset elastomers represent a class of polymers for a wide range of biomedical applications. Crosslinking density of thermoset elastomers is considered as an important parameter. Here, semiquantitative Fourier transform infrared (FTIR) analysis is developed as a novel method to determine crosslinking density of poly (ester amide) thermoset elastomers. Poly(1,3-diamino-2-hydroxypropane-co-polyol sebacate) (APS) is an example of poly(ester amide) thermoset elastomer. Polyethylene glycol (PEG) has been recently incorporated into APS polymer structure to obtain novel PEGylated APS-based elastomers with tunable properties. The crosslinking densities of different APS and APS-co-PEG films are determined by the theory of rubber elasticity and FTIR. These results show that the intensity ratios between amide and carbonyl peak correlate well with the calculated crosslinking density from the elastic modulus. Thus, semiquantitative FTIR analysis offers a direct, facile, and less variable method to determine the crosslinking density and guide the consistent synthesis of poly(ester amide) thermoset elastomers.

Biodegradable synthetic elastomers represent one of the most promising materials for a wide range of biomedical applications including soft tissue engineering and drug delivery. Of different biodegradable elastomers, thermoset elastomers can maintain network architecture during degradation and gradually lose their mechanical properties in a relatively linear manner. This property has been considered as a major advantage of thermoset elastomers over thermoplastic materials. Typical preparation of thermoset elastomers requires thermal/photocrosslinking of a prepolymer to obtain crosslinked elastomeric network. The crosslinking density of thermoset elastomers plays an important role in determining their mechanical and degradation properties, which are two key parameters for the biomedical applications. Currently, the estimation of crosslinking density of thermoset elastomers is mainly based on the calculation from the theory of rubber elasticity. In this theory, the elastic modulus is independent of the chemical structure of the elastomer and depends primarily on the tightness of the network structure. The application of theory of rubber elasticity for measuring crosslinking density has been shown in polymer networks such as epoxy and polyester. Such calculation requires mechanical testing on large quantity of prepared material samples (usually in grams), which in most cases, leads to the deformation or rupture of the materials. It is disadvantageous if the materials are available in small quantities or difficult to synthesize. Also, mechanical testing has an intrinsic variability, which may result in different elastic moduli for the same material produced among batches and labs. Importantly, this calculation is only accurate in reflecting the crosslinking density of an ideal elastomer. Each polymer chain of ideal elastomer is free to rotate, coil or uncoil without changing the internal energy. However, not all real thermoset elastomers can be treated as "ideal elastomers" and especially for highly crosslinked systems, the calculation based on theory of rubber elasticity may not be true. Consequently, there is a critical need to develop a method for assessing the crosslinking density of thermoset elastomers to circumvent these drawbacks and guide the consistent synthesis of thermoset elastomers with desired mechanical and degradation properties.

Poly(1,3-diamino-2-hydroxypropane-co-polyol sebacate) (APS) is one of the promising classes of biodegradable thermoset elastomers that has been well characterized and explored for fabrication of airway stent, microfluidic scaffolds, and electrospun scaffolds. The crosslinking density of APS can be tuned by monomer ratios, crosslinking temperature, and crosslinking time. The crosslinking density, in turn, affects degradation and mechanical properties. APS possess both ester and amide functional groups in their chemical structures. Consequently, their FTIR spectra exhibit characteristic absorption peaks representing carbonyl and amide groups. These peaks are usually strong and without interference from other peaks, thus can be exploited for semiquantitative FTIR analysis by comparing the carbonyl bond and amide bond ratio in the structure. Here, semiquantitative FTIR analysis of the amide and carbonyl peaks present in poly (ester amide)-based thermoset elastomers is used as a direct and facile method to measure the crosslinking density of this class of elastomers. To demonstrate the versatility of the proposed FTIR analysis method, two new APS-co-PEG elastomers are synthesized, their crosslinking density is determined both by the theory of rubber elasticity and semiquantitative FTIR analysis.

Synthesis of Poly(1,3-Diamino-2-Hydroxypropane-Co-glycerol Sebacate) Prepolymer—

Sebacic acid (SA), glycerol (G), and 1,3-diamino-2-hydroxy-propane (DAHP) were purchased from Sigma-Aldrich. The APS prepolymer was synthesized by the polycondensation reaction of DAHP, G, and SA. The molar ratio of DAHP:G in APS polymer was kept constant at 2:1.

Briefly, a round-bottom flask was charged with a molar ratio of 2:1:3 of DAHP:G:SA monomer mixture. The reactants were heated under argon atmosphere at 120° C. for 3 h. Approximately 300 mTorr vacuum was applied to the reaction system and the reaction continued for another 9 h at 120° C. to obtain APS prepolymer. To obtain the crosslinked elastomer, the prepolymer was uniformly spread on a Teflon dish and thermally cured at 170° C. for 12, 24, 48, or 72 h in a vacuum oven to fabricate thermally crosslinked APS film. The thickness of the film was around 1.5 mm.

Synthesis of Poly(1,3-Diamino-2-Hydroxypropane-Co-glycerol Sebacate)-Co-Poly(Ethylene Glycol) (APS-Co-PEG) Prepolymers—

The synthesis scheme of APS-co-PEG is shown in FIG. 1. Two APS-co-PEG prepolymers were synthesized by varying molar percentage of PEG to SA (10% and 50%), but keeping the molecular weight of PEG constant at 1 kDa. Briefly, APS-co-PEG prepolymers were synthesized via a two-step condensation polymerization. The first step is the polycondensation reaction between SA and PEG (Dow, Mn=1 kDa). The mixture was heated in a round-bottom flask at 130° C. under Argon atmosphere for 2 h and the reaction was continued at 120° C. under reduced pressure of 300 mTorr for 48 h. In the second step, specific amounts of G and DAHP were added into the round bottom flask and mixed thoroughly with the reactants (Molar ratio of SA:PEG:DAHP:G for APS-10PEG: 3:0.3:1.8:0.9; APS-50PEG: 3:1.5:1:0.5). The reaction was stirred at 120° C. under Argon atmosphere for 30 min and continued for 12 h at 120° C. under reduced pressure of 300 mTorr to obtain APS-co-PEG prepolymers. To obtain the crosslinked elastomer, the APS-co-PEG prepolymer was spread on a Teflon dish and thermally cured at 170° C. for 12, 24, 48, or 72 h in a vacuum oven. The thickness of films was kept constant around 1.5 mm.

FTIR Characterization of the Prepolymer and Thermally Cross-Linked Polymer Films—

Chemical composition of the prepolymers was studied using nuclear magnetic resonance (1H NMR) spectroscopy (Bruker 400) and Fourier transform infrared (FTIR) spectroscopy with attenuated total reflection (ATR-FTIR). The prepolymer samples were dissolved in $CDCl_3$ and the spectra were recorded at 400 MHz. $^1$H NMR (400 MHz, $CDCl_3$, δ/ppm): 1.30 (m, —$CH_2$—), 1.62 (m, —$CH_2CH_2O(CO)$—), 2.35 (m, —$CH_2O(CO)$—), 3.64 (m, —$OCH_2CH_2O$—), 3.72 (m, —$NCH_2CHOHCH_2$ N—), 4.22 (m, —$OCH_2CHOHCH_2O$—). The FTIR spectra were recorded in the absorption mode with a resolution of 4 cm$^{-1}$ using Bruker Vertex 70 FTIR spectrometer. The results are presented as an average of 256 scans. Carbonyl, amide I and amide II peak intensities were integrated for semiquantitative analysis using Origin8 software. Peak intensity ratio of amide I:carbonyl (ratio 1) and peak ratio of amide II:carbonyl (ratio 2) was calculated.

Mechanical Testing of the Thermally Cross-Linked Polymer Films—

The mechanical properties of APS and APS-co-PEG polymer films cured for various time points (12-72 h) were evaluated by uniaxial tensile tests using ADMET MTEST Quattro mechanical testing system equipped with 10 lb load cell (n=3). Thermally crosslinked polymer films were cut into rectangular shape (10 mm×7 mm) for uniaxial tensile tests. Samples were stretched until failure at constant jogging speed of 10 mm/min. The stress (MPa) was obtained by dividing the applied force (N) with cross-section area (mm 2), and percentage elongation (% strain) was obtained from the displacement using $(L-L_0)/L_0 \times 100$, where $L_0$ was initial gauge length and L was instantaneous gauge length. Ultimate tensile strength (UTS) was recorded as the maximum stress at sample failure. Elastic modulus was calculated from the linear stress-strain curve between 5% and 15% strain regions.

Calculation of the Crosslinking Density of Polymer Films from Elastic Modulus—

Elastic modulus calculated from the linear stress-strain curve was used to calculate the crosslinking density based on the theory of rubber elasticity using the Equation (5): N=E/3RT (5), where N is the crosslinking density (mol m$^{-3}$), E is the Young's modulus (Pa), R is the universal gas constant (8.3144 J mol$^{-1}$ K$^{-1}$), and T is the absolute temperature, which is 298° K.

Statistics—

Experimental data were presented as mean±standard deviation. Student's paired t-test was used for comparisons between two groups. Statistical differences between multiple groups were analyzed using one-way ANOVA followed by the Tukey post-hoc analysis. Relative standard deviations (RSDs) were calculated to compare the variation. Two-tailed Pearson's correlation tests were performed to examine the correlation between calculated crosslinking density and FTIR ratio. Pearson product-moment correlation coefficient (Pearson's r) was used to measure the linear correlation (dependence) between the crosslinking density and FTIR peak intensity ratios. p values less than 0.05 were considered significant.

Results

Synthesis of APS and APS-Co-PEG Polymers—

APS elastomers with varied monomer selection, monomer feed ratio, and curing time have been developed as described herein. The APS polymer formulation 2DAHP-1G (molar ratio of DAHP and G is constant at 2:1) was selected as a representative elastomer in this study (FIG. 1). Curing time was varied from 24 to 72 h to tune the crosslinking density. Based on APS polymer (2DAHP-1G), two PEGylated APS elastomers (APS-co-PEG) were synthesized by varying molar percentage (10% and 50%) of PEG (molecular weight 1 kDa) to SA. The APS-co-PEG elastomers were denoted as APS-xPEG, where "x" represents molar percentage of PEG with respect to SA. APS-co-PEG prepolymers were synthesized by the two-step polycondensation reaction (FIG. 1). The first step of the reaction is the polycondensation reaction between SA and PEG, which yielded polyester with SA-PEG repeating. In the second step, DAHP and G were added to the reaction mixture where α-hydroxyl groups of G or α-amino groups of DAHP continued to react with carboxyl groups of SA forming ester or amide bonds, respectively. This is because the α-hydroxyl groups and α-amino groups have higher reactivity than β-hydroxyl groups. During the final crosslinking stage, an elevated temperature (170° C.) was used to promote the crosslinking of polymer chains by esterification reaction between the less-reactive β-hydroxyl groups of G and DAHP with carboxyl groups of SA. This synthetic route is consistent with the previous reports on the polycondensation reaction between tri-functionalized alcohol and dicarboxylic acid, where the prepolymers with unreacted β-hydroxyl groups were obtained prior to the crosslinking process. Similar to APS prepolymer, APS-10PEG and APS-50PEG prepolymers were not elastic due to the lack of crosslinking among individual polymer chains. APS-10PEG prepolymer could be cured in about 12 h at the same temperature used for APS curing (170° C.). The cured/crosslinked polymer could not be melted upon heating and exhibited elastic mechanical properties. However, APS-50PEG prepolymer could not be cured even after 96 h of thermal crosslinking. In this case, APS-50PEG cannot be processed into film for mechanical testing to obtain elastic modulus. Therefore, its crosslinking density, if there is some, cannot be estimated by the theory of rubber elasticity.

Chemical Characterization of Prepolymers and Thermally Crosslinked Polymers—

Figure 17A:
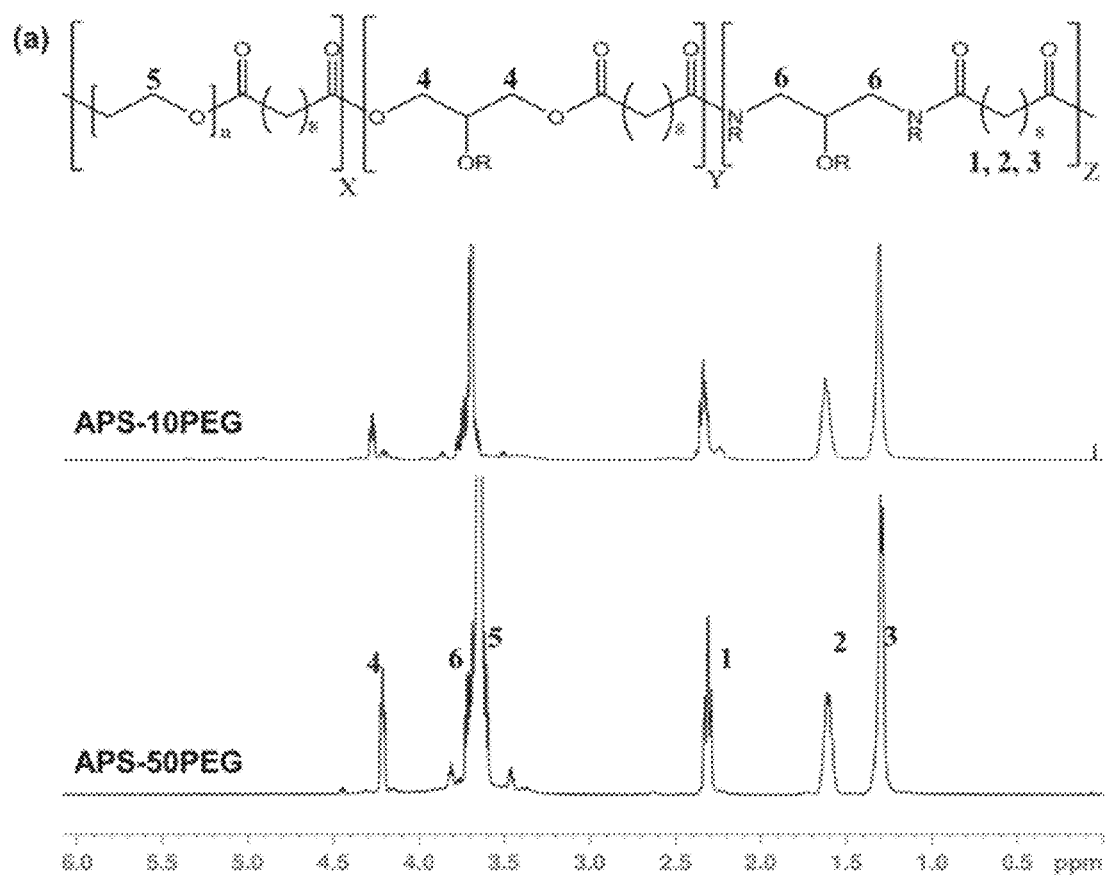
FIGS. 17A and 17B. a) Structure and $^1$H NMR spectra of APS-10PEG and APS-50PEG prepolymer. Peak assignments for APS-50PEG are representative for APS-co-PEG prepolymers. b) FTIR spectra of APS prepolymer, APS-10PEG prepolymer and APS-50PEG prepolymer. Carbonyl, amide I and amide II peaks are highlighted and used for quantification. c) Ratio of peak intensity between amide peaks and carbonyl peak for APS prepolymer, APS-10PEG prepolymer and APS-50PEG prepolymer.
Figure 17B:
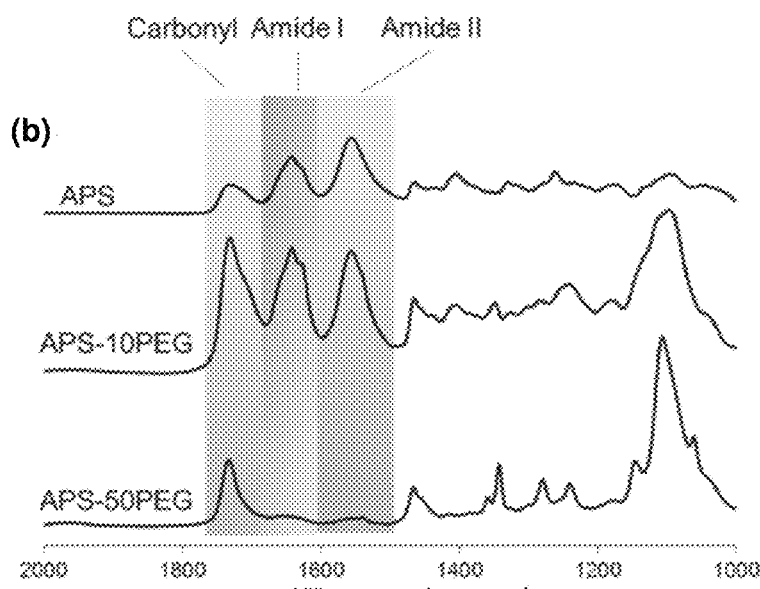

The $^1$H NMR spectra of APS-10PEG prepolymer and APS-50PEG prepolymer as well as the FTIR spectra of PEG, APS prepolymer, APS-10PEG prepolymer, and APS-50PEG prepolymer demonstrated the successful synthesis of prepolymers (FIG. 17). The $^1$H NMR spectra of both APS-10PEG and APS-50PEG did not show any peak from the monomers G or DAHP (FIG. 17 (a). Instead, due to the ester and amide bond formation, the αH in glycerol shifted from 3.5-3.7 ppm to 4.2 ppm and that in DAHP shifted from 2.5-2.7 ppm to 3.72 ppm (FIG. 17 (a). In FTIR spectra (FIG. 17 (b)), the carbonyl peaks (1730 cm$^{-1}$) observed in the spectra of APS, APS-10PEG, and APS-50PEG indicated successful formation of ester bonds between SA and glycerol and/or PEG while amide I and amide II peaks (1646 and 1552 cm$^{-1}$, respectively) indicated bonds between SA and DAHP in the prepolymer chains. Additionally, characteristic C—O—C stretching and C—H bending peaks of PEG were observed at 1100, 1464, and 1343 cm$^{-1}$ in the spectra of APS-10PEG and APS-50PEG prepolymer, but not in the APS prepolymer spectrum. More importantly, the intensity ratios of the amide I (1646 cm$^{-1}$) to carbonyl peak (1730 cm$^{-1}$) and amide II (1552 cm$^{-1}$) to carbonyl peak (1730 cm$^{-1}$) were lower in the FTIR spectra of APS-10PEG and APS-50PEG than the corresponding ratios observed in the spectrum of APS (FIG. 17 (c)). This is because of the reduced amide bond formation and the increased ester bond formation in APS-co-PEG prepolymer compared to those in APS. These results suggested that PEG was covalently linked to SA instead of physically blended in the polymer structure. These results are in accordance with our previous results where higher mole % as well as molecular weight of PEG resulted in reduced amide bond formation and increased ester bond formation.

Figure 18A:
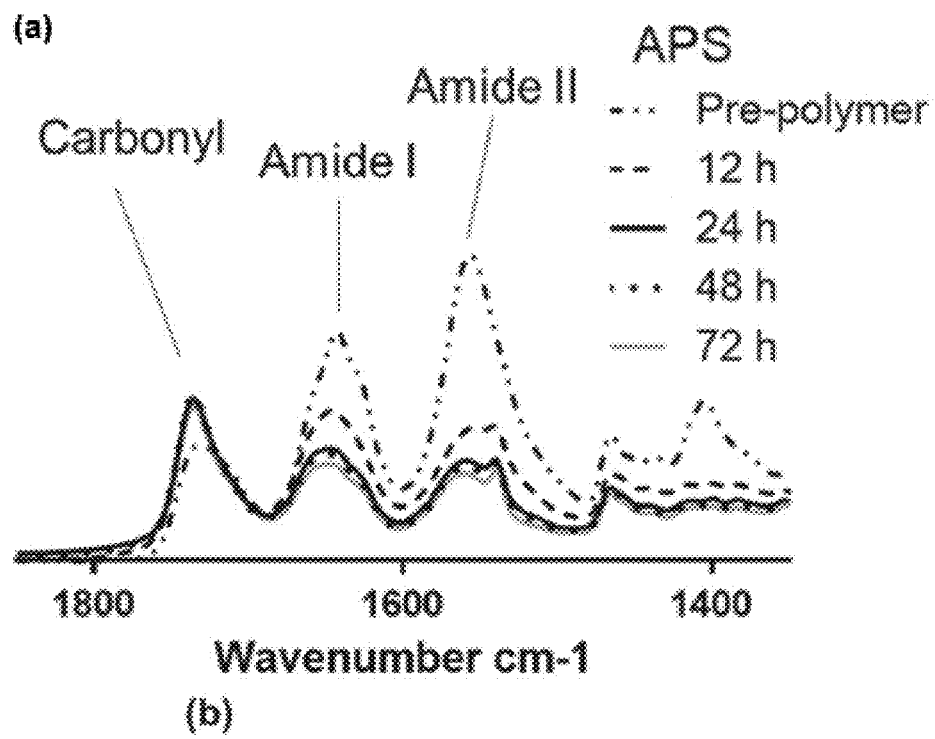
FIGS. 18A and 18B. a) FTIR spectra of APS prepolymer and polymer after thermal crosslinking for different time. b) Ratio of peak intensity between amide peaks and carbonyl peak at different crosslinking times. c) FTIR spectra of APS-10PEG prepolymer and polymer after thermal crosslinking for different time. d) Ratio of peak intensity between amide peaks and carbonyl peak at different crosslinking times.
Figure 18B:
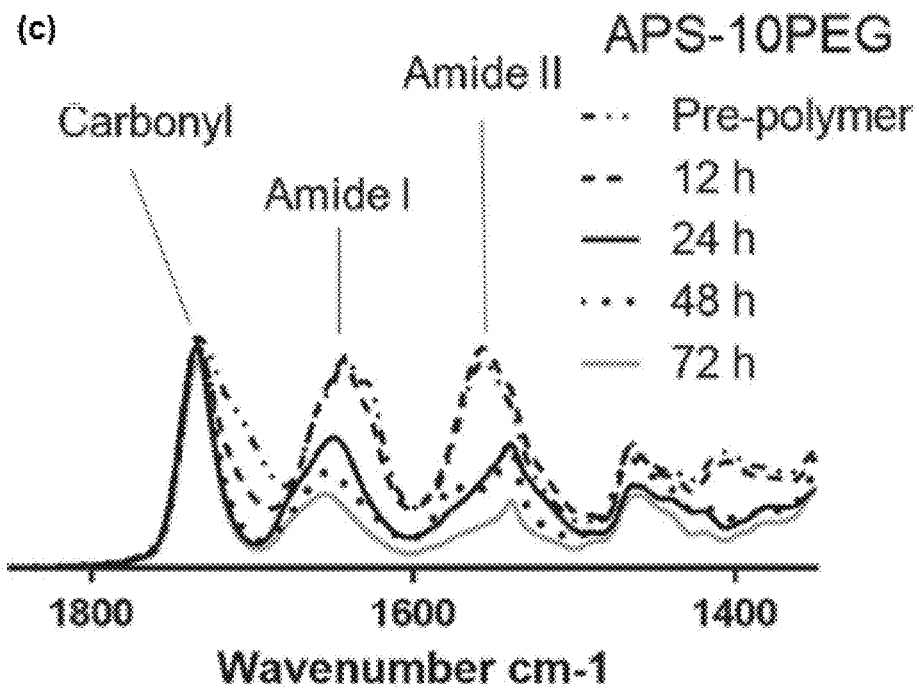

During the crosslinking process of APS and APS-co-PEG, β-hydroxyl groups of G and DAHP, having lower reactivity than α-hydroxyl groups, further reacted with SA. Therefore, there is an increase in the number of ester bonds throughout the polymer structure while amide bonds showed little or no change during crosslinking. The changes in the amide and carbonyl bond ratio can be clearly reflected by semiquantitative FTIR analysis. In FTIR curves, carbonyl peak of ester has stronger intensity than carbonyl peak of carboxylic acid. Therefore, ester bonds formed during crosslinking resulted in an increase in the carbonyl peak intensity. Indeed, comparison between the FTIR spectra of the prepolymer and cured polymers of APS and APS-10PEG showed that the intensity ratios of the amide I to carbonyl peak (1646/1730 cm$^{-1}$) and amide II to carbonyl peak (1552/1730 cm$^{-1}$) in spectra of the cured elastomers were lower than those of the prepolymers, respectively. Overall, the esterification reaction during crosslinking process led to increase in the carbonyl peak intensity measured by FTIR without affecting amide peak intensity causing decrease in amide to carbonyl peak ratio. Consequently, these results suggested that there were newly formed ester bonds during crosslinking process, which could chemically connect single polymer chains into network structure, and eventually confer elasticity to the polymeric films. Intensity ratios of the amide to carbonyl peaks gradually reduced during the crosslinking process of APS (FIG. 18 (a,b)) and APS-10PEG (FIG. 18 (c,d)), which illustrated the increase in ester bonds due to the reaction between SA and the β-hydroxyl groups of G and DAHP and therefore, the increased crosslinking density. Thus, semi-quantitative FTIR analysis using intensity ratios of amide to carbonyl peaks can serve as an alternative method to monitor the crosslinking density in real time.

Figure 19:
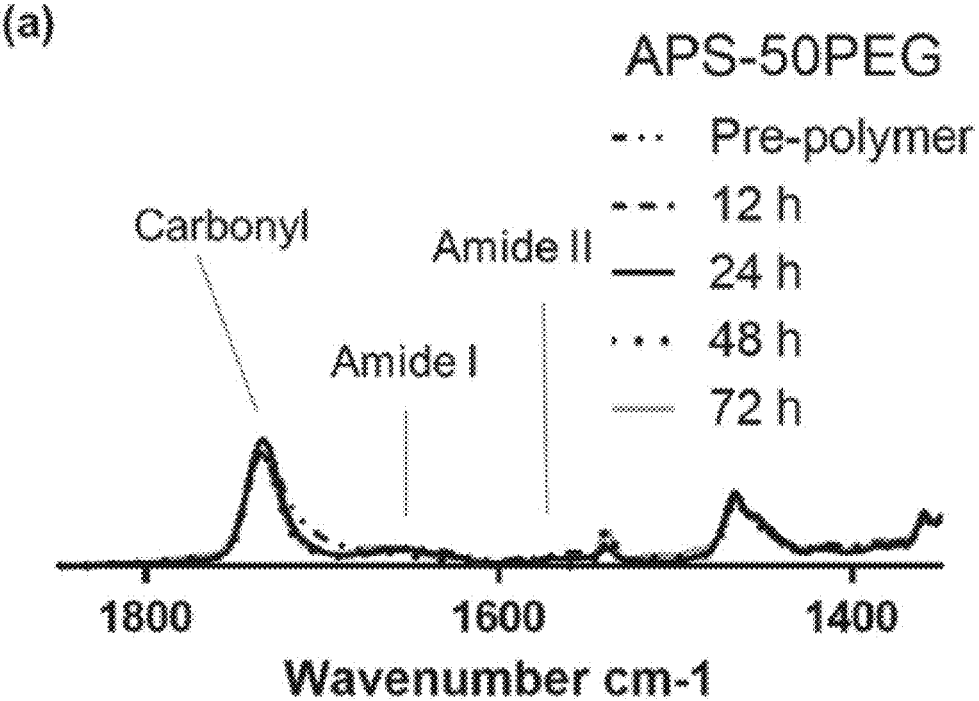
FIG. 19. a) FTIR spectra of APS-50PEG prepolymer and polymer after thermal crosslinking for different time. b) Ratio of peak intensity between amide peaks and carbonyl peak at different crosslinking times.

When comparing the FTIR spectra of the prepolymer and thermally cured polymers of APS-50PEG, intensity ratios of the amide I to carbonyl peak and amide II to carbonyl peak of ester bond in the spectra of thermally cured polymers were similar to those of prepolymer, indicating little or no newly formed ester bonds and low degree of crosslinking density (FIG. 19). This result was in accordance with our observation that APS-50PEG could not be thermally cured even after 96 h, suggesting the potential and robustness of semiquantitative FTIR analysis in assessing the crosslinking density of non-ideal elastomers. It has been shown that semiquantitative FTIR analysis on amide:carbonyl peak intensity ratios directly monitored the change in the polymer structure during crosslinking process at molecular level and therefore, may serve as a new method of measuring crosslinking density.

Correlation of FTIR Results and Crosslinking Density—

Figure 20:
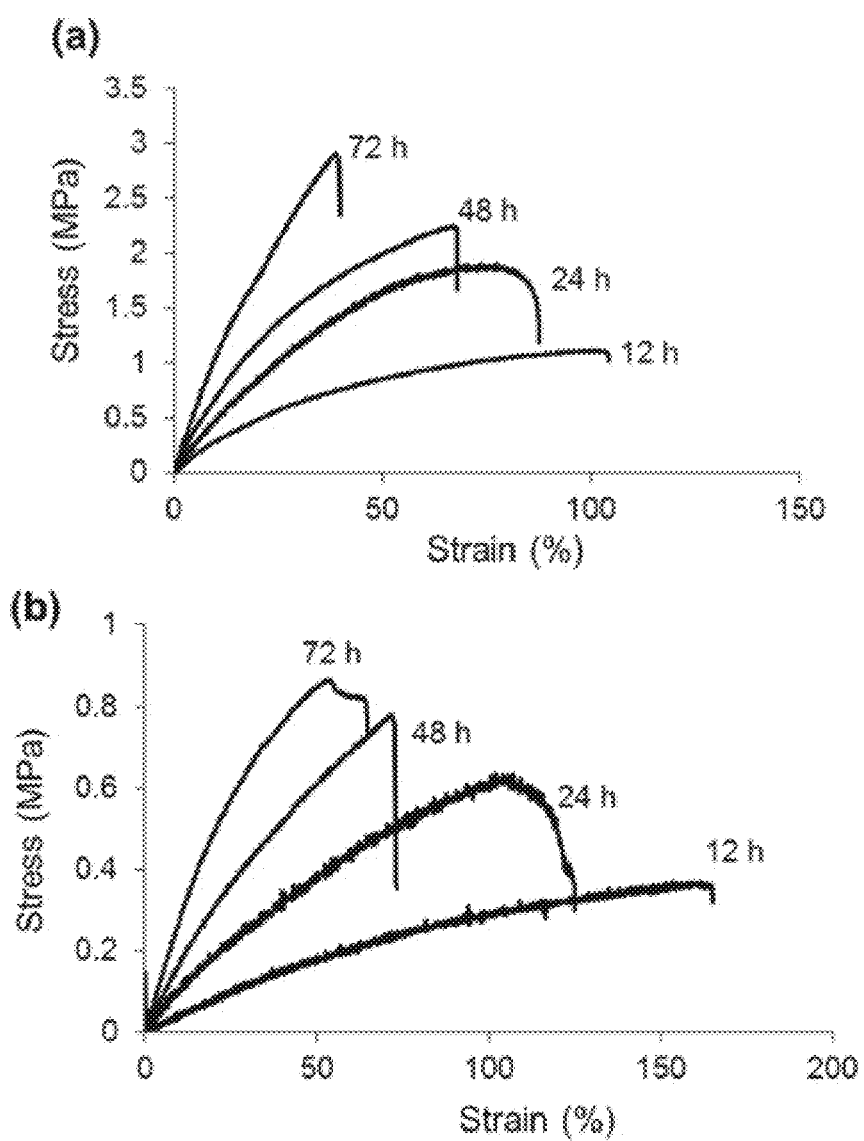
FIG. 20. Representative stress-strain curve of a) APS films after different crosslinking time; and b) APS-10PEG films after different crosslinking time.
Figure 21A:
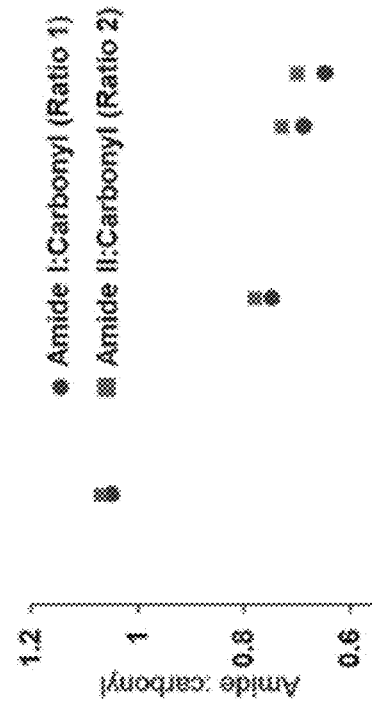
FIGS. 21A and 21B. The correlation between the calculation of crosslinking density from theory of rubber elasticity and peak ratio of a) APS elastomers (n=3) b) APS-10PEG elastomers (n=3).
Figure 21B:
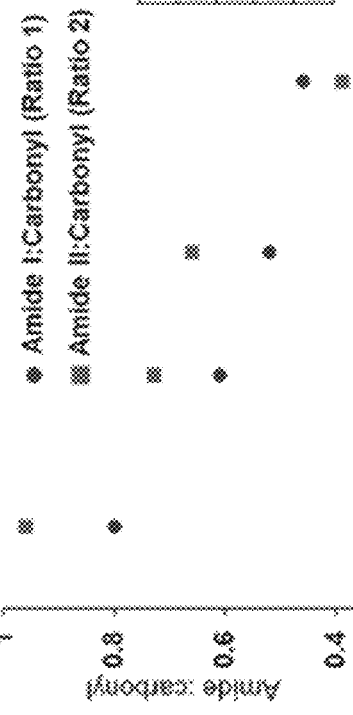

To further investigate the relationship between calculated crosslinking density and the amide to carbonyl peak intensity ratios, APS and APS-10PEG elastomers cured for different time to obtain varying crosslinking density were tested for their mechanical properties by uniaxial tensile test. Both APS and APS-10PEG elastomer films cured for different times showed varying mechanical properties as a consequence of different crosslinking density (FIG. 20). In accordance with existing literature reporting the crosslinking density of thermoset elastomers such as poly(polyol sebacate), (J. P. Bruggeman, et al., Biodegradable poly (polyol sebacate) polymers, *Biomaterials* 2008, 29:4726-35) APS, (C. J. Bettinger, et al., Biomaterials 29 (15) (2008) 2315-2325) and poly(diol malates) (L. Y. Lee, et al., Biodegradable elastomer for soft tissue engineering, *Eur. Polym. J.* 2009, 45, 3249-56), the crosslinking density of APS and APS-10PEG was calculated from the corresponding elastic modulus obtained from the stress-strain curve (from 5% to 15% strain region) using Equation 5 (FIGS. 21A and 21B, table). Subsequently, amide I: carbonyl (ratio 1) and amide II: carbonyl (ratio 2) peak intensity ratios were plotted against calculated crosslinking density. Correlation between ratio 1/ratio 2 and crosslinking density were examined by a two-tailed Pearson's correlation test. A negative correlation between ratio 1/ratio 2 and crosslinking density was observed for both APS and APS-10PEG, as indicated by a negative Pearson's r. For APS elastomers, there was a significant correlation between ratio 1 and crosslinking density (p=0.0483), while ratio 2 and crosslinking density did not exhibit significant correlation (p=0.0561). For APS-10PEG elastomers, there was significant correlation between ratio 1 and crosslinking density (p=0.0402) as well as ratio 2 and crosslinking density (p=0.0111). These results demonstrated that amide: carbonyl peak intensity ratios, especially ratio 1, could be used as an alternative to the values calculated based on the theory of rubber elasticity for assessing the crosslinking density of poly(ester amide)-based thermoset elastomers. More importantly, the RSD of each crosslinking density calculated from elastic modulus was much higher than that of ratio 1 and ratio 2 (n=3). This highlighted another advantage of semiquantitative FTIR analysis over traditional calculation of crosslinking density from elastic modulus. The relatively larger intrinsic variability of mechanical testing than FTIR analysis has been demonstrated in the literature. Usually, RSD of elastic modulus of a typical elastomer obtained from uniaxial mechanical testing system ranges from 5 to 25%. Meanwhile, quantitative and semiquantitative FTIR analyses are known to have low RSD ranging from 0.5 to 5%. Our mechanical and FTIR results showed similar RSD as reported in the literature and further demonstrated that semiquantitative FTIR analyses of amide: carbonyl peak intensity ratios can be used to determine the crosslinking density of poly(ester amides) with less variability.

In conclusion, a semiquantitative FTIR analysis method is provided based on amide: carbonyl peak intensity ratios for assessing the crosslinking density of poly(ester amide)-based thermoset elastomers. It showed significant correlation with the calculated values based on the classical theory of rubber elasticity. In addition, this method has several advantages over classical method, including: 1) less quantity of materials required; 2) better preservation of sample during the testing; and 3) direct reflection of the change in chemical structure at molecular level during crosslinking and avoid the use of theorized model. This method can potentially predict the mechanical properties of specific poly(ester amide)-based thermoset elastomers under different synthetic conditions and will guide the consistent synthesis of these materials with tailored mechanical properties. We envision that this method can be further applied to a variety of poly (ester amide)-based thermoset elastomers and provide the uniformity of their characterization among different batches and labs.

Example 4—Platelet Adhesion

A hybrid APS-co-PEG/polycaprolactone (PCL) porous scaffold was fabricated by electrospinning. The fiber morphology, chemical composition, mechanical properties, degradability, and cytocompatibility of hybrid APS-co-PEG/PCL electrospun scaffolds were characterized. These scaffolds exhibited a wide range of mechanical properties and similar cytocompatibility to PCL scaffolds. PEGylation inhibited platelet adhesion on all APS-co-PEG/PCL electrospun scaffolds when compared to PCL and APS/PCL scaffolds, suggesting a potential role in mitigating thrombogenicity in vivo. Additionally, APS-25PEG/PCL scaffolds were found to be mechanically analogous to human heart valve leaflet and supported attachment of human aortic valve cells. These results reveal that hybrid APS-co-PEG/PCL scaffolds may serve as promising constructs for soft tissue engineering, especially heart valve tissue engineering.

It is demonstrated above, that the mechanical properties of APS-co-PEG elastomers can be tuned by the choice of PEG molar percentage, PEG molecular weight, monomer feed ratio and cross-linking time. Specifically, cross-linked APS-co-PEG elastomeric films exhibited a wide range of ultimate uniaxial tensile strength (0.07-2.38 MPa), elastic modulus (0.02-3.0 MPa) and elongation (93-993%). Additionally, the solubility of APS-co-PEG pre-polymers in common organic solvents was significantly improved compared to non-PEGylated APS elastomers.

Electrospinning has been comprehensively investigated for applications in tissue engineering due to its versatility and ease in processing porous scaffolds with high surface area-to-volume ratio that can mimic native fibrous ECM (Bhardwaj N, Kundu S C. Electrospinning: A fascinating fiber fabrication technique. Biotechnol Adv. 2010; 28(3): 325-47). It has been shown that the electrospinning of thermoset elastomer pre-polymer along with a carrier polymer can result in elastomeric electrospun scaffolds (Sant S, et al. Hybrid PGS-PCL microfibrous scaffolds with improved mechanical and biological properties. Journal of Tissue Engineering and Regenerative Medicine. 2011; 5(4): 283-91; Mukundan S, et al. Nanofibrous composite scaffolds of poly(ester amides) with tunable physicochemical and degradation properties. Eur Polym J. 2015; 68:21-35; Masoumi N, et al. Electrospun PGS:PCL Microfibers Align Human Valvular Interstitial Cells and Provide Tunable Scaffold Anisotropy. Adv Healthc Mater. 2014; 3(6):929-39; Gaharwar A K, et al. Anisotropic poly (glycerol sebacate)-poly (ε-caprolactone) electrospun fibers promote endothelial cell guidance. Biofabrication. 2014; 7(1):015001; and Fu W, et al. Electrospun gelatin/PCL and collagen/PLCL scaffolds for vascular tissue engineering. International journal of nanomedicine. 2014; 9:2335-44). As an example, poly(glycerol sebacate) (PGS), a benchmark biodegradable thermoset elastomer, has been studied extensively as electrospun scaffolds (Sant S, et al. Journal of Tissue Engineering and Regenerative Medicine. 2011; 5(4):283-91; Masoumi N, et al. Adv Healthc Mater. 2014; 3(6):929-39; Sant S, et al. Effect of biodegradation and de novo matrix synthesis on the mechanical properties of valvular interstitial cell-seeded polyglycerol sebacate polycaprolactone scaffolds. Acta biomaterialia. 2013; 9(4):5963-73; Tong Z, et al. Controlling the fibroblastic differentiation of mesenchymal stem cells via the combination of fibrous scaffolds and connective tissue growth factor. Tissue engineering Part A. 2011; 17(21-22):2773-85; and Soliman S, et al. Controlling the porosity of fibrous scaffolds by modulating the fiber diameter and packing density. J Biomed Mater Res A. 2011; 96A(3):566-74), demonstrating the feasibility and effectiveness of electrospinning of thermoset elastomer prepolymer along with a carrier polymer. The electrospun PGS/PCL scaffolds have tunable mechanical properties and improved biological properties than that of PCL alone. Moreover, PGS/PCL scaffolds have been shown to promote cell attachment/spreading, promote de novo ECM synthesis and support stem cell differentiation (Id.).

The following demonstrates the fabrication and characterization of electrospun scaffolds composed of newly synthesized APS-co-PEG elastomers with varying PEG molar ratio (APS-15PEG, APS-25PEG and APS-40PEG). PCL is used as a carrier polymer. We also demonstrate that these scaffolds support adhesion/spreading of skeletal muscle cells (C2C12) and human aortic valve cells. PEGylation of elastomers markedly reduces platelet adhesion on these scaffolds while maintaining their excellent mechanical properties, demonstrating their potential for use in skeletal muscle and heart valve tissue engineering.

Materials:

All organic solvents used in the study and 1,3-diamino-2-hydroxy-propane (DAHP), glycerol (G), sebacic acid (SA), poly (ε-caprolactone) (PCL, Mn=70-90 kDa) were purchased from Sigma-Aldrich (St. Louis, Mo.). PEG (Mn=1 kDa) was obtained from Dow Chemical (Midland, Mich.). Cell culture supplies including media, trypsin-EDTA and antibiotics were obtained from Corning (Corning, N.Y.), unless otherwise mentioned.

Synthesis of Poly(1,3-Diamino-2-Hydroxypropanecopolyol) Sebacate (APS) and Poly(1,3-Diamino-2-Hydroxypropane-Co-Glycerol Sebacate)-Co-Poly(Ethylene Glycol) (APS-Co-PEG) Elastomer:

APS elastomer was synthesized as follows. Briefly, DAHP, G and SA in 2:1:3 molar ratios were mixed in a round bottom flask. The mixture was allowed to react at 120° C. for 1 h under argon atmosphere and constant stirring. The pressure was then dropped to approximately 200 mTorr and the reactants were allowed to react at 120° C. for 10 h. At the end of the reaction, a light yellow colored wax-like elastomer was obtained.

APS-co-PEG pre-polymers were synthesized via the one-pot two-step condensation polymerization as described above. The first step is the polycondensation reaction between SA and PEG. The mixture was heated in a round bottom flask at 130° C. under argon atmosphere for 2 h and the reaction was maintained at 120° C. under 300 mTorr for 48 h. In the second step, G and DAHP were added and mixed thoroughly with the reactants. The mixture was stirred at 120° C. under argon atmosphere for 30 min and continued at 120° C. under reduced pressure of 300 mTorr for 12 h to obtain APS-co-PEG pre-polymers. Here, a series of APS-co-PEG pre-polymers were synthesized by varying PEG mole percentage (15%, 25% and 40% of PEG1K) and labeled as APS-15PEG, APS-25PEG, APS-40PEG as described above.

Scaffold Fabrication by Electrospinning:

Following APS and APS-co-PEG polymer synthesis, porous scaffolds were fabricated using the electrospinning technique. Electrospinning parameters such as solvents, polymer concentration, voltage, distance and flow rate were varied to obtain the optimal electrospinning conditions as shown below. Briefly, APS or APS-co-PEG (APS-15PEG, APS-25PEG and APS-40PEG) and ε-PCL were dissolved in hexafluoroisopropanol (HFIP) in an 80:20 w/w ratio with total polymer concentration kept constant at 17.5% w/v in HFIP. Electrospinning was conducted on a conventional electrospinning setup, using aluminum foil as collector. Solutions were electrospun at 17 kV for 1 h at a rate of 1 mL/h. The distance between the needle and collector was 10 cm. The obtained electrospun scaffolds were dried in a vacuum desiccator for 1 week. Scaffolds were then soaked in deionized water to allow for the removal of any sprayed polymer and remaining solvent.

Chemical Characterization of Electrospun Scaffolds:

Chemical composition of the scaffolds was studied using Fourier Transform Infrared (FTIR) spectroscopy with attenuated total reflection (ATR-FTIR). The spectra were recorded in absorption mode with a resolution of 4 cm$^{-1}$ using Bruker Vertex 70 FTIR spectrometer (Bruker, Billerica, Mass.). The results are presented as an average of 256 scans. The intensities of ester, amide I, and amide II peaks were integrated for semi-quantitative analysis using Origin8 software as described above.

Morphology of Electrospun Scaffolds:

Scaffold morphology and porosity was characterized using scanning electron microscopy (SEM) (JEOL 6335F Field Emission SEM, Japan). Fibrous scaffolds were sputter-coated with 5 nm of gold-palladium using Cressington 108 auto sputter-coater (Cressington Scientific Instruments, UK) and images were obtained using accelerated voltage of 3 kV. Fiber diameter measurements were performed using NIH ImageJ software. 100 fibers were considered for calculating fiber diameters.

Thermal Properties of Electrospun Scaffolds:

The thermal properties of electrospun scaffolds were studied by differential scanning calorimeter (DSC) (Mettler Toledo, Allison Park, Pa.). The scaffold (approx. 5 mg) was sealed in an aluminum pan and first heated from room temperature to 150° C., then cooled to −70° C., and finally reheated to 150° C. at a heating/cooling rate of 10° C./min. All the processes were carried out under nitrogen atmosphere. Crystallization temperature (Tc) and enthalpy (ΔHc) were obtained from the cooling cycle (150° C. to −70° C.) whereas glass transition temperature (Tg), melting temperature (Tm) and enthalpy (ΔHm) were obtained from the second heating cycle (−70° C. to 150° C.). DSC data was analyzed using STARe software.

Mechanical Properties of Electrospun Scaffolds:

Scaffold mechanical properties were studied using uniaxial tensile tests with ADMET MTEST Quattro mechanical testing system (ADMET, Norwood, Mass.). Scaffolds were cut into rectangular shapes (15×7 mm$^2$, n=8 per group) and stretched until failure at a constant jogging speed of 10 mm/min. The stress (MPa) was obtained by dividing the applied force (N) with cross-section area (mm$^2$); percent elongation (strain, E) was obtained from Equation (6), where $L_O$ was initial gauge length and L was instantaneous gauge length. Ultimate tensile strength (UTS), maximum strain to total failure (% elongation), toughness (area under the curve of stress-strain curve), and elastic modulus in the linear region at 5-15% strain were recorded for each scaffold tested. Cyclic mechanical testing was performed at a jogging rate of 10 mm/min, by sample extension until 20% elongation during 10 consecutive cycles.

$$\text{Elongation}(\varepsilon,\%)=(L-L_0)/L_0 \cdot 100 \quad \text{Eq. (6)}$$

Degradability of Electrospun Scaffolds:

In vitro degradation properties were studied by submerging 10×10 mm$^2$ scaffold samples in 10 mL PBS solution in 50 mL falcon tubes. Solutions were maintained in a shaking incubator at 37° C. and 50 rpm. At predetermined intervals, the scaffolds were weighed after gentle washing in deionized water and fresh PBS solution was replaced in the falcon tubes. Mass loss, compared to the original hydrated scaffold mass, and solution pH were measured. The percentage of mass loss was calculated using Equation 7, where $W_o$ is the initial weight of as-prepared scaffold and $W_t$ is the weight of scaffold at each time point.

$$\text{Mass loss }(\%)=(W_0-W_t)/W_0 \times 100 \quad \text{Eq. (7)}$$

Cytocompatibility of Electrospun Scaffolds Using Mouse Myoblast (C2C12) Cells:

The preliminary cytocompatibility of the electrospun scaffolds was studied by evaluating attachment, spreading and metabolic activity of mouse myoblast cells (C2C12) from ATCC (CRL-1772™) seeded onto the scaffolds. The cells were cultured in Dulbecco's Modified Eagle Medium (DMEM) supplemented with 10% Fetal Bovine Serum (FBS) (Hyclone, Marlborough, Mass.) and 1% Penicillin/Streptomycin solution. Cells in passages 3-7 were used. The scaffolds (9 mm×9 mm) were sterilized by exposing to 70% isopropanol under UV light for 30 min, washed with DPBS thrice, and seeded with C2C12 cells at a density of 45,000 cells/scaffold in a 24-well plate. The media was replenished every day. The cell attachment and spreading of C2C12 cells were studied by staining actin (ActinGreen™ 488 Ready-Probes® Reagent, Life Technology, Waltham, Mass.) and nuclei of seeded cells (NucBlue® Fixed Cell Stain, Life Technology, Waltham, Mass.) after 6 h of culture. The cell-seeded scaffolds were fixed in 4% paraformaldehyde solution (30 min), washed with DPBS thrice, followed by permeabilization and blocking using 0.1% Triton X-100 and 3% bovine serum albumin (BSA) in DPBS. Confocal images were obtained using an inverted confocal laser scanning microscope (Olympus Fluoview 1000, Japan) under 20× and 40× objectives.

The metabolic activity was measured over a period of 7 days using the AlamarBlue® assay (Invitrogen, Carlsbad, Calif.) according to the manufacturer's protocol. Briefly, cell-seeded scaffolds (n=4) were treated with 10% v/v AlamarBlue® solution in growth medium for 4 h at 37° C.

The fluorescence intensity was then measured using a microplate reader (Gen5 Biotek, Winooski, Vt.) at excitation/emission wavelengths of 530/590 nm. AlamarBlue® solution (10% w/v) incubated without any cells was used for blank correction.

Platelet Adhesion Assay:

Human platelet-rich plasma (PRP) with a platelet density of 1 million/mL was obtained. Platelet adhesion assay protocol was adopted from literature (Kidane A G, et al. A novel nanocomposite polymer for development of synthetic heart valve leaflets. Acta biomaterialia. 2009; 5(7):2409-17). The scaffolds (9 mm×9 mm) were placed in 0.5 ml of PRP in a 24-well plate. All scaffolds were then incubated at 37° C. for 1 h with gentle mixing. Scaffolds were rinsed twice with PBS and fixed with glutaraldehyde solution in PBS (2.5% v/v) for 2 h at room temperature; then the samples were dehydrated in vacuum and images using SEM as described above.

Adhesion and Spreading of Human Aortic Valve Cells:

Fresh human aortic valve cells were obtained from human aortic valves. Valve tissues were digested in 2.5 mg/mL Collagenase IV with DMEM (+1% Penicillin/Streptomycin+1% Fungizone) for 30 min at 37° C. with gentle rocking. Digested tissue was passed through 70 m filter and saved at 37° C. Undigested tissue was further digested with 0.8 mg/mL Collagenase IV for 1 h at 37° C. with gentle rocking. Digested tissue was passed through 70 m filter and pool with previous digested tissue. The pooled digested tissue was centrifuged at 2000 rpm for 5 min at 4° C. and then the supernatant was discarded. Cells were resuspended in T75 flask with 12 mL Endothelial medium supplemented by Gentamicin (60 µL) and Fungizone (120 µL). The cells were propagated using Endothelial Cell Growth Media Kit (Cell Applications, San Diego, Calif.). The scaffolds (9 mm×9 mm) were sterilized by exposing to 70% isopropanol under UV light for 30 min, washed with DPBS thrice, and seeded with valve cells using a seeding density of 300,000 cells/scaffold in a 24-well plate. After 4 days in culture, the cell-seeded scaffolds were fixed and permeabilized as described above. Human valve cell adhesion and spreading were studied by staining actin (ActinGreen™ 488 Ready-Probes® Reagent), α-smooth muscle actin (α-SMA, Mouse Anti-Human Actin, Dako, Carpinteria, Calif.) and nuclei of the seeded cells (NucBlue® Fixed Cell Stain). Confocal images were obtained as described above.

Statistical Analysis:

Experimental data are presented as mean±standard deviation. Data between multiple groups were analyzed using one-way ANOVA or two-way ANOVA followed by Tukey's post-hoc analysis. P-values less than 0.05 were considered as significant.

Results and Discussion

Fabrication of Electrospun Scaffold and Scaffold Morphology:

Hybrid APS/PCL and APS-co-PEG/PCL electrospun scaffolds were successfully fabricated using optimized electrospinning parameters, namely total polymer concentration (17.5% w/v), solvents (HFIP), voltage (17 kV), flow rate (1 mL/h) and collector-to-needle distance (10 cm). PCL was used as a carrier polymer. The weight ratio between APS-co-PEG and PCL was kept constant at 4:1 throughout the study to highlight the effect of APS-co-PEG.

Figure 22:
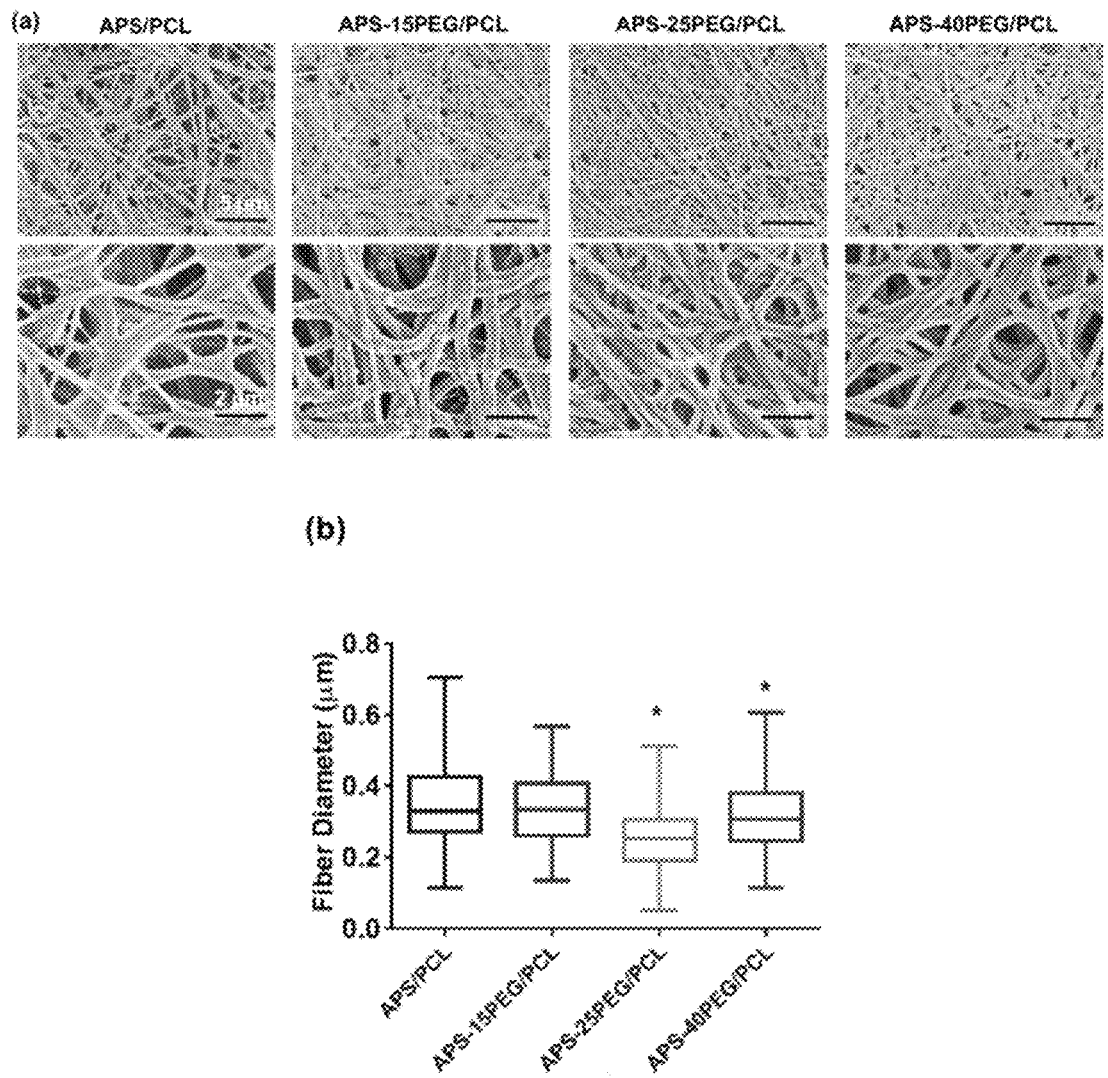
FIG. 22 (a) Fiber morphology of electrospun APS-co-PEG/PCL scaffolds studied by scanning electron microscopy at ×5000 (top) and ×15000 (bottom) magnification. Scale bars in top rows represent 5 µm; scale bars in bottom rows represent 2 µm (b) Average fiber diameters (n=100 fibers per group), *p<0.05 with respect to APS/PCL scaffolds.

Scanning electron microscopy revealed porous fibrous and porous structure of all scaffolds fabricated from different APS-co-PEG pre-polymers (FIG. 22 (a)). The nanofibrous porous structure of electrospun scaffolds mimics the fibrous structure of native ECM and has been shown to improve the exchange of nutrients and waste products and promote cell attachment/spreading, thereby leading to higher cell proliferation (Kim E S, et al. Emerging nanotechnology approaches in tissue engineering and regenerative medicine. International journal of nanomedicine. 2014; 9 Suppl 1:1-5.). SEM image analysis revealed that the average fiber diameters of all electrospun scaffolds were approximately 300 nm (FIG. 22 (b)). These scaffolds exhibit a desirable fiber diameter range since cells seeded on polymer scaffold secrete ECM proteins, like collagen, which often form fibrils of similar size. It should be noted that different PEGylated elastomers did not significantly alter fiber morphology and the average fiber diameter of all scaffolds remained in the same range (around 300 nm). This is attributed to the processing of all polymer blends using constant electrospinning parameters such as polymer concentration, voltage and needle-to-collector distance, which have been shown to be the main determinants for scaffold morphology and average diameter.

Figure 23:
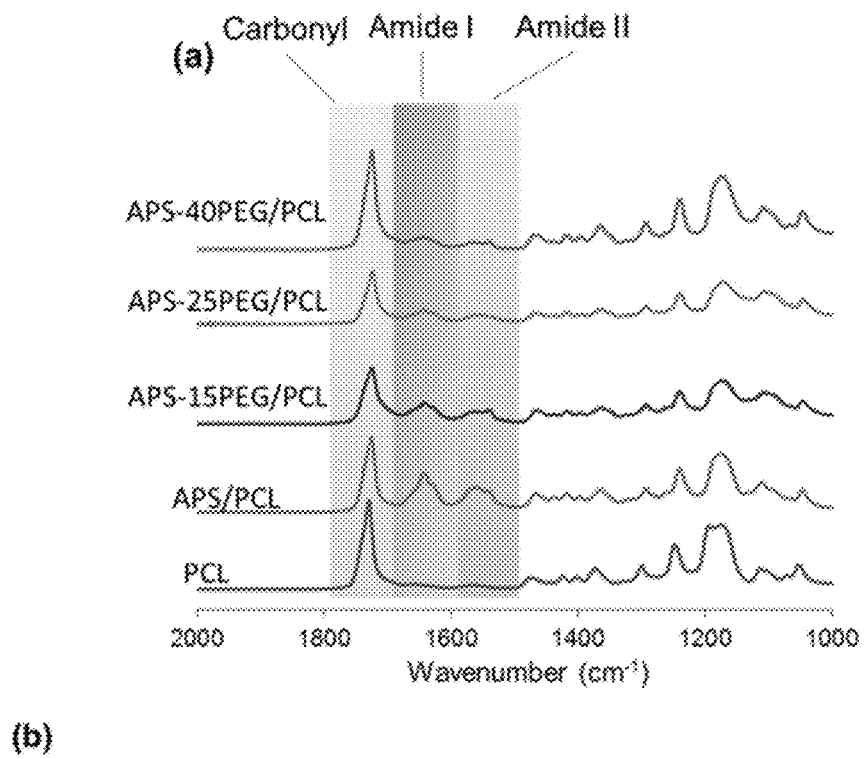
FIG. 23 (a) FTIR spectra of electrospun PCL, APS/PCL and APS-co-PEG/PCL scaffold. Ester, amide I and amide II peaks are highlighted for semi-quantitative analysis. (b) Polymer/PCL showed decreased amide peaks I (1646 cm$^{-1}$) to carbonyl peak (1730 cm$^{-1}$) and amide II (1552 cm$^{-1}$) to carbonyl peak (1730 cm$^{-1}$) intensity ratio than those of corresponding polymer alone group.

Chemical Characterization:

FTIR was used to characterize the chemical composition of electrospun scaffolds. The detailed FTIR analysis on APS-co-PEG polymers is presented above. Briefly, APS-co-PEG polymers showed characteristic carbonyl (1730 cm$^{-1}$), amide I (1646 cm$^{-1}$), amide 11 (1552 cm$^{-1}$) peak from APS moiety and C—O—C stretching (1110 cm$^{-1}$) and C—H bending (1464 &1343 cm$^{-1}$) peaks of PEG moiety in their FTIR spectra. FTIR curves of APS-co-PEG/PCL scaffolds showed peaks from both APS-co-PEG and PCL (FIG. 23 (a)). Amide to carbonyl peak intensity ratios can be used to determine the ratio of amide and ester bonds in the polymer blends (15). Since there is ester bond but no amide bond in the PCL structure, the FTIR spectra of APS-co-PEG/PCL scaffolds showed decreased amide I: carbonyl and amide II: carbonyl ratios when compared to those of APS-co-PEG polymer alone, respectively (FIG. 23 (b)). In addition, with the increase in PEG molar ratio, there is further decrease in amide: carbonyl ratio in the FTIR spectra of APS-co-PEG/PCL scaffolds, which is similar to the trend observed in APS-co-PEG elastomers (15). Overall, FTIR results suggest that PCL was physically blended in the scaffolds with no chemical interaction with APS or APS-co-PEG elastomers, as the characteristic carbonyl peaks of PCL (~1730 cm$^{-1}$) were not shifted after incorporation of PCL into the scaffolds.

Figure 24:
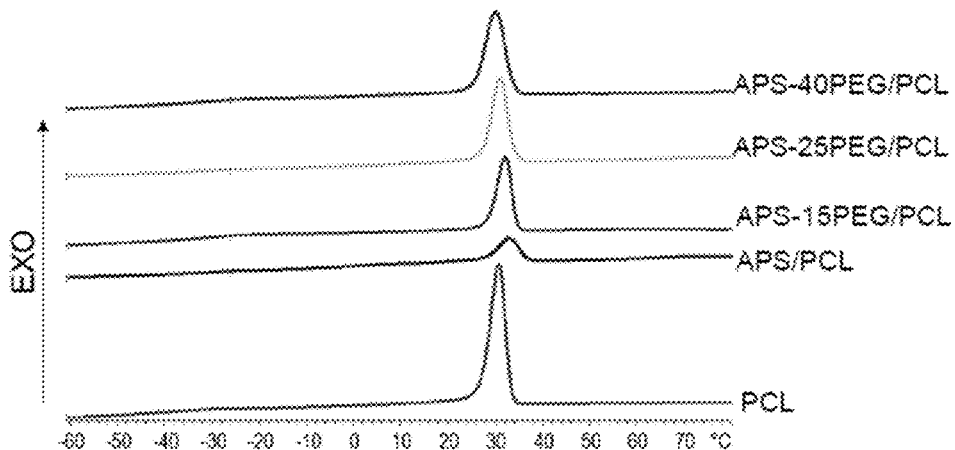
FIG. 24 Thermal properties of electrospun APS-co-PEG/PCL scaffolds. (a) DSC curves of the cooling cycle and (b) the heating cycle of APS-co-PEG pre-polymers; (c) Summary of the thermal properties of electrospun scaffolds. Tg: glass transition temperature; Tc: crystallization temperature; ΔHc: crystallization enthalpy; Tm: melting temperature; ΔHm: melting enthalpy.
Figure 24:
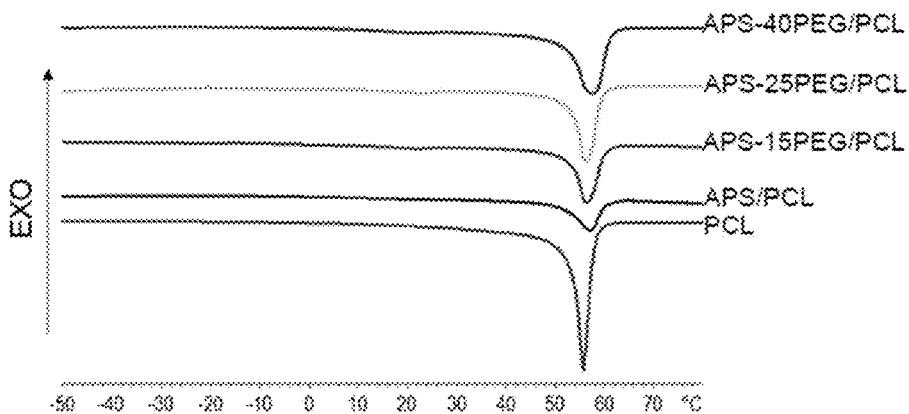

Thermal Characterization:

The thermal properties of the scaffolds were investigated by DSC (FIG. 24 (a) and (b)). In this study, the scaffolds were first heated to 150° C. to eliminate the thermal history. The cooling cycle (from 150° C. to −70° C.) was used to obtain crystallization temperature (Tc) and enthalpy (ΔHc) while the second heating cycle (−70° C. to 150° C.) was used to obtain glass transition temperature (Tg), melting temperature (Tm) and enthalpy (ΔHm). PCL, being semicrystaline polymer, did not exhibit Tg in the temperature range studied here. APS/PCL scaffolds exhibited Tg of −1.4° C., which decreased with increasing PEG molar percentage in the APS-co-PEG elastomers from 15 to 40 mole % (FIG. 24 (c)). This may be attributed to the plasticizer effect of PEG, consistent with the data above. It should be noted that all the scaffolds had a Tg in the range of −23 to −1° C., which is significantly lower than the body temperature. Low Tg is usually favorable for the elastomeric scaffold since such material will be elastic in vivo. We also examined the crystallization and melting behaviors of the scaffolds. There were no significant differences in Tc and Tm of all scaffolds, further supporting our conclusion that PCL is physically blended with APS or APS-co-PEG elastomers (FIG. 24 (a-c)). As revealed by high values of ΔHc and ΔHm, electrospun PCL scaffolds maintained crystalline nature of PCL polymers while the presence of amorphous APS polymers in APS/PCL hybrid scaffolds reduced the crystallinity of these scaffolds. Interestingly, there was an increase in ΔHc and ΔHm of APS-co-PEG/PCL hybrid scaffolds with the increase in the PEG ratio in APS-co-PEG elastomers.

Figure 25A:
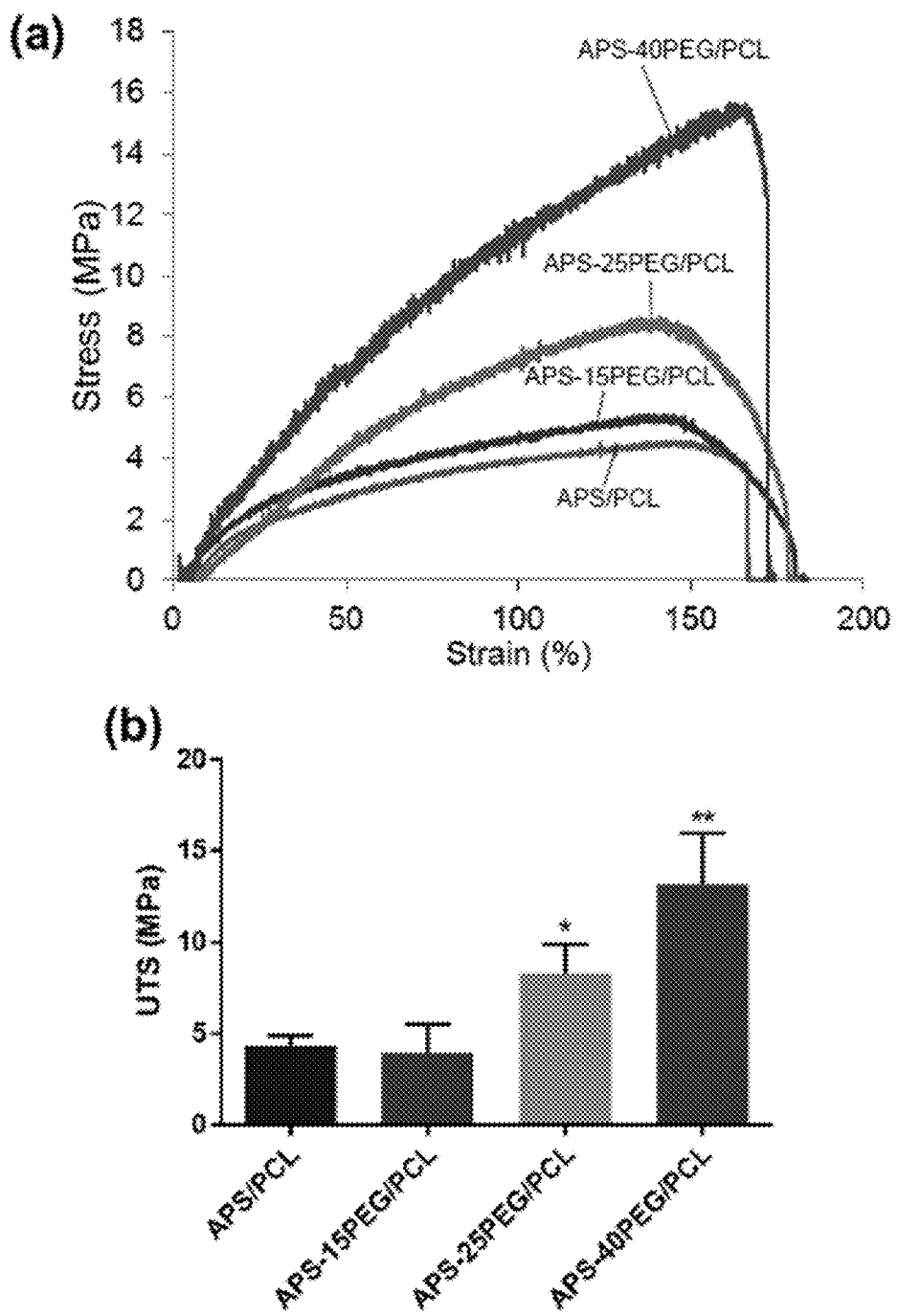
FIGS. 25A and 25B Mechanical properties of electrospun APS/PCL and APS-co-PEG/PCL scaffolds. (a) Representative stress strain curves of APS-PEG/PCL electrospun scaffold; (b) ultimate tensile strength (UTS); (c) elastic modulus; and (d) toughness of APS-co-PEG/PCL scaffolds (n=8). Significant differences at p<0.01 (*) or p<0.001 (**) when compared to APS/PCL.
Figure 25B:
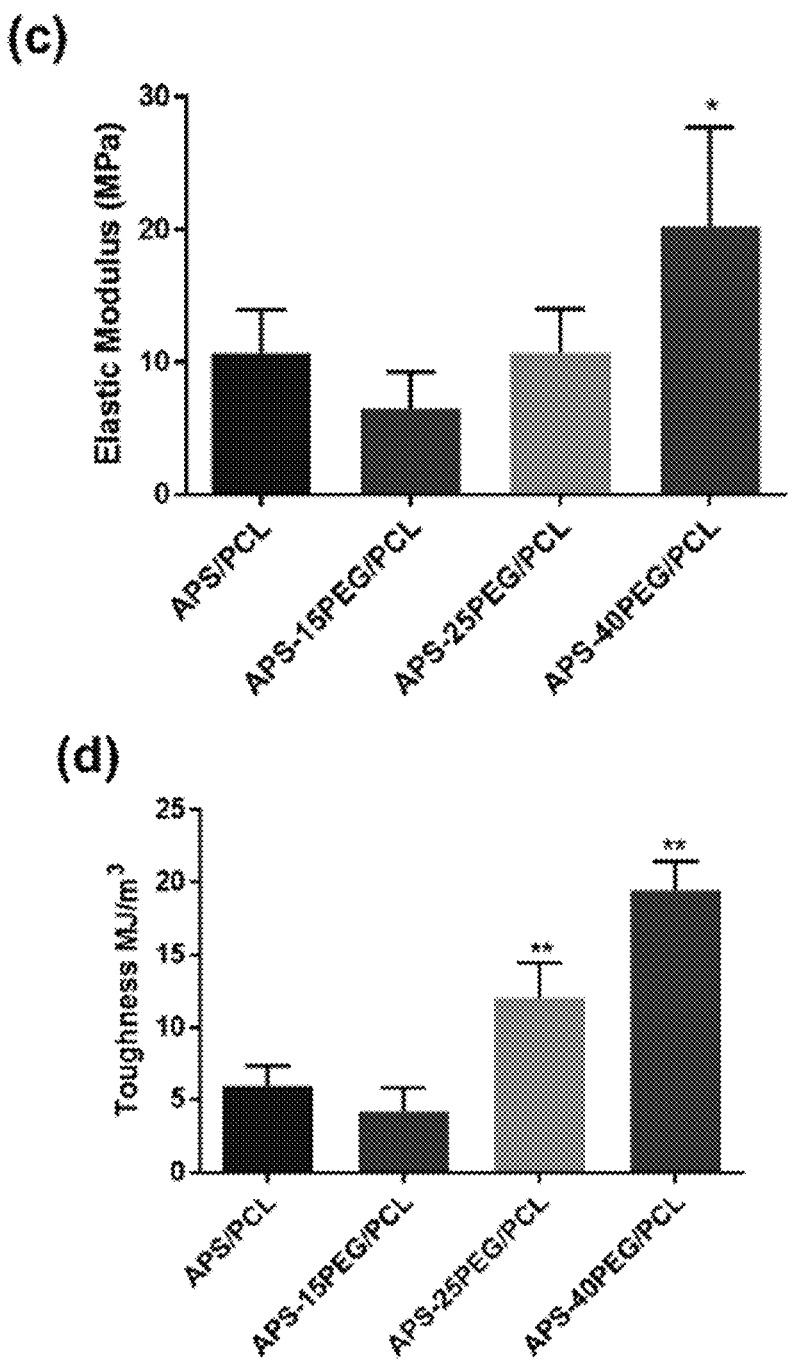

Mechanical Properties of Electrospun Scaffolds:

To test the mechanical properties of the scaffolds, uniaxial tensile test was performed (FIG. 25A (a)). The ultimate tensile stress (FIG. 25A (b)), stiffness (FIG. 25B (c)) and toughness (FIG. 25B (d)) of scaffolds increased with PEG concentration in APS-co-PEG ($p<0.05$, One-way ANOVA). Overall, APS-co-PEG/PCL scaffolds showed tunable mechanical properties. It is noteworthy that the mechanical properties of these scaffolds may be further tuned by changing the ratio of APS-co-PEG/PCL ratio and other electrospinning parameters. It has been widely acknowledged that tailoring the mechanical properties of TE scaffold with that of native tissue is crucial to guide the tissue regeneration. Therefore, APS-co-PEG/PCL scaffolds with wide range of mechanical properties might be promising constructs for TE biomaterials used in an array of tissues.

Figure 26A:
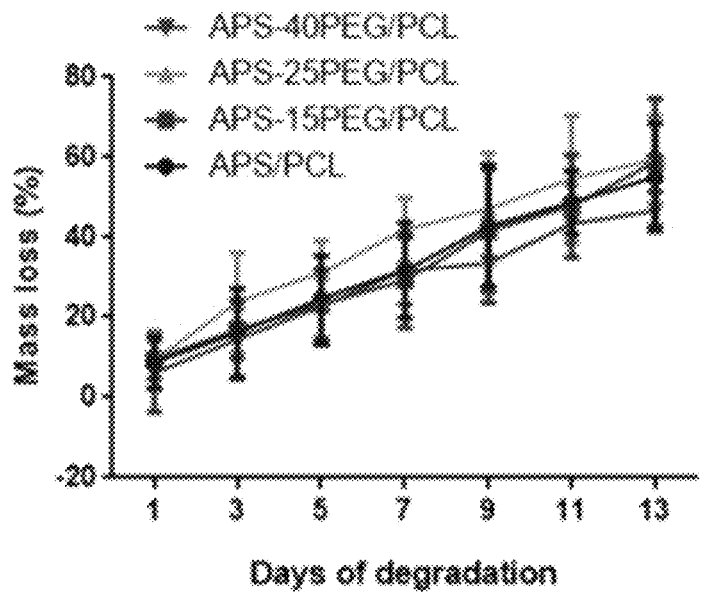
FIGS. 26A and 26B Degradation properties of electrospun APS/PCL and APS-co-PEG/PCL scaffolds. (a) Percentage mass loss of APS-co-PEG/PCL scaffold after degradation in PBS at 37° C. (n=3); (b) Change in pH of PBS during degradation (n=3); (c) Scaffold morphology after 14 days of degradation. All scale bars represent 2 µm. (d) Average fiber diameters of as prepared and degraded scaffolds. (n=100 fibers per group) *p<0.05
Figure 26A:
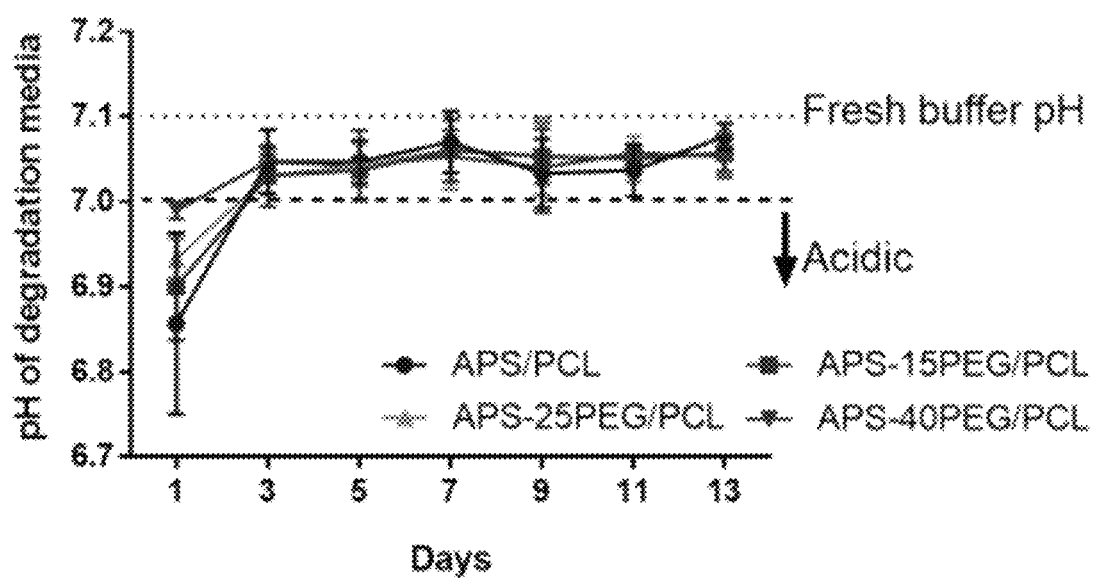

In Vitro Degradation Studies:

From the in vitro degradation study, it was found that all scaffolds degraded at a similar rate, with no statistical differences between APS-co-PEG/PCL and APS/PCL (FIG. 26A (a)). All scaffolds exhibited around 50% mass loss after 2 weeks in PBS. Degradation of all scaffolds followed a linear trend suggesting that the primary mechanism was probably through surface degradation (Lyu S, et al. Degradability of Polymers for Implantable Biomedical Devices. International journal of molecular sciences. 2009; 10(9): 4033-65). Scaffold degradation by surface erosion is generally considered advantageous since it maintains the scaffold geometry with gradual decrease in mechanical properties unlike the sudden mechanical failure observed during bulk degradation. Interestingly, the varying amounts of PEG did not influence the degradation rate of scaffolds unlike in the case of thermally crosslinked APS-co-PEG films. This may be attributed to multiple reasons. First, in the examples above, the varying degradation rates of thermally crosslinked APS-co-PEG films containing different PEG amounts were partially attributed to the different crosslinking density of the polymer structure. Here, APS-co-PEG pre-polymers were used, which rules out the possible influence of polymer crosslinking density thereby minimizing the difference in degradation rates. In addition, the presence of the carrier polymer, PCL, should not be overlooked. As APS and APS-co-PEG cannot be electrospun alone, the intertwining of its fibers with those of PCL may create a PCL coating over the APS and APS-co-PEG in the scaffolds, thus interfering with the hydrolytic degradation processes. Finally, nanofibrous APS-co-PEG/PCL scaffolds have significantly higher surface area than those of the cross-linked films, resulting in higher degradation rates than film scaffolds.

The pH change during degradation is an important parameter since acidic degradation products might cause in vivo inflammatory responses (Chapman R G, et al. Surveying for Surfaces that Resist the Adsorption of Proteins. Journal of the American Chemical Society. 2000; 122(34):8303-4). A slightly lower pH compared to the initial buffer pH of 7.1 was observed throughout the study for all experimental groups (FIG. 26A (b)), indicating that acidic degradation products were released from all scaffolds particularly at the beginning of the study. However, the pH of degradation solution in all APS-co-PEG/PCL groups was found to be near or higher than 7 at all times during degradation (FIG. 26A (b)). Of note, on day 1, all APS-co-PEG/PCL scaffolds had less pH reduction in degradation media than APS/PCL scaffold. Also, the drop of pH in degradation solution was less after day 1, despite a constant rate of mass loss rate (FIG. 26A (a)). These results suggested that APS-co-PEG/PCL scaffolds might lead to less in vivo inflammatory responses due to acidic degradation products.

Figure 26B:
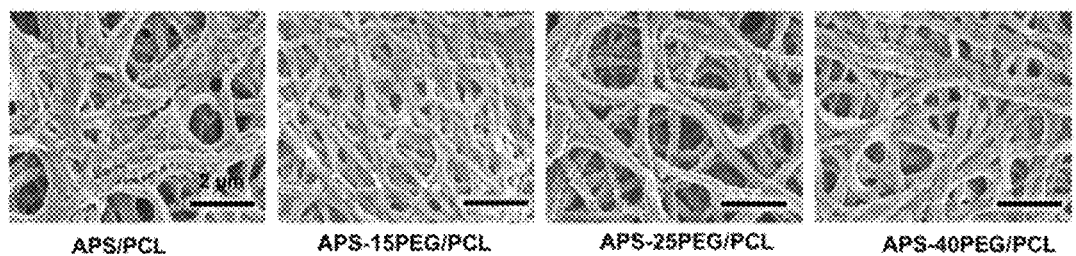
Figure 26B:
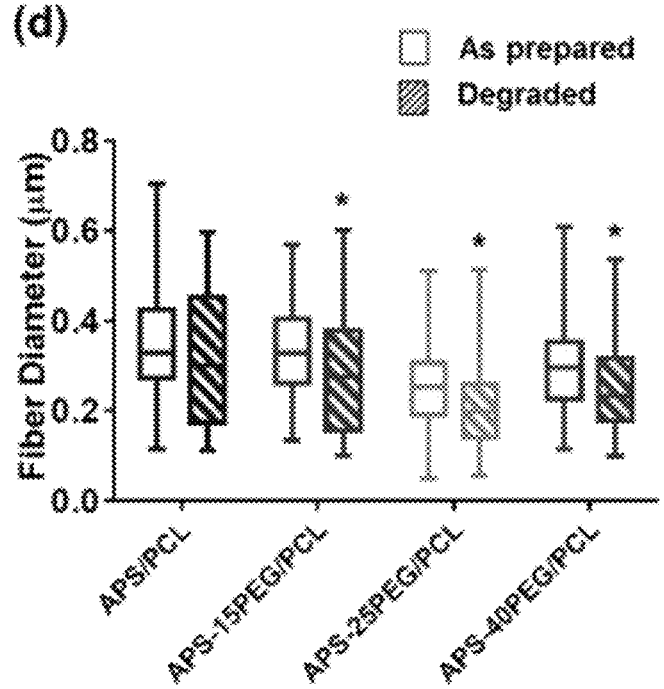

Scaffold morphology was investigated after 2-week degradation by SEM (FIG. 26B (c)). SEM images showed that all scaffolds maintained nanofibrous structure even after about 50% mass loss, although the scaffold surface showed increased roughness. Furthermore, mean fiber diameter of each group was reduced after the degradation study, affirming that the degradation was probably by surface degradation (open vs. lined squares in FIG. 26B (d)) ($p<0.05$, Two-way ANOVA).

Figure 27:
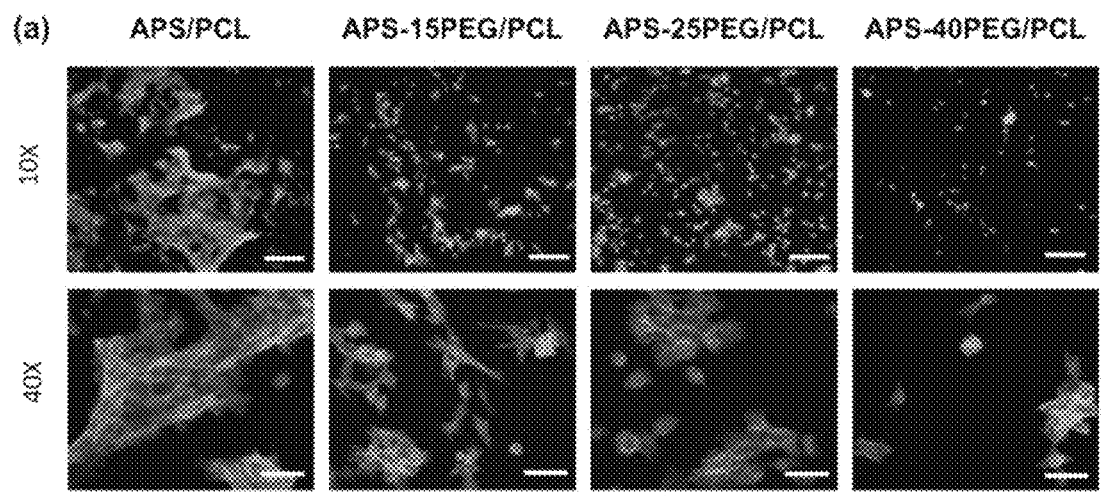
FIG. 27 Cytocompatibility of electrospun APS/PCL and APS-co-PEG/PCL scaffolds with mouse myoblast (C2C12) cells. (a) Morphology of C2C12 cells on electrospun scaffolds at 6 h after seeding. Actin cytoskeleton was stained with ActinGreen (green) and nuclei stained with NucBlue (blue). Scale bars in 10× images represent 200 µm; Scale bars in 40× images represent 50 µm; (b) Metabolic activity of C2C12 cells on electrospun scaffolds over 7 days after seeding (n=3).
Figure 27:
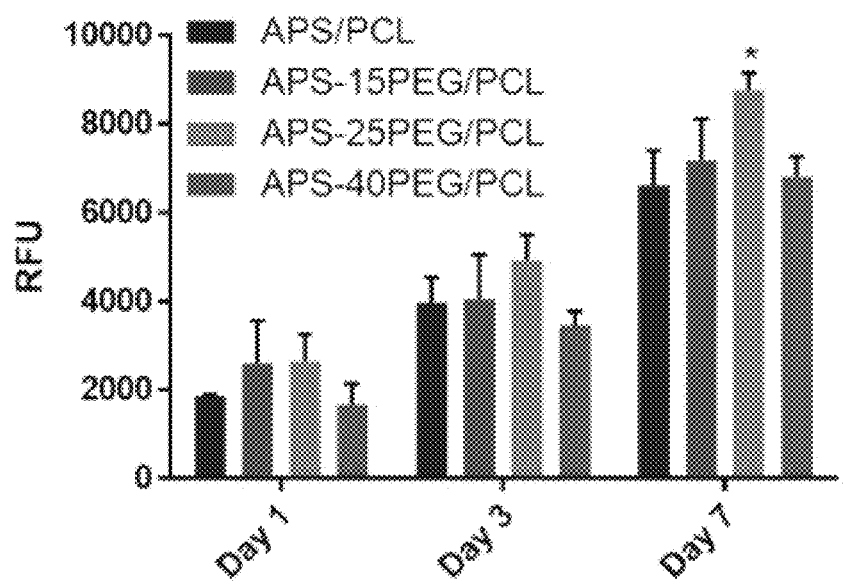

Cytocompatibility of Electrospun Scaffolds:

A mouse myoblast cell line (C2C12) was chosen as a model system to evaluate biocompatibility of different scaffolds. Initial attachment and spreading of C2C12 cells on scaffolds were examined by immunostaining of cell nuclei and cytoskeleton after 6 h of culture following cell seeding (FIG. 27 (a)). APS/PCL (control) scaffolds exhibited high initial cell attachment and spreading morphology. APS-co-PEG/PCL groups showed reduction in initial cell attachment, which may be attributed to the increased scaffold hydrophilicity resulted from the presence of PEG in the elastomer. As shown above, APS-co-PEG elastomer films also showed reduced initial cell attachment compared to APS film. However, APS-co-PEG/PCL scaffolds did support cell spreading, indicated by the stretched cell morphology similar to APS/PCL groups 6 h post cell seeding. Cell proliferation on scaffolds were investigated from day 1 to day 7 using AlamarBlue® assay, which measures the metabolic activity of cells (FIG. 27 (b)). It was observed that all the scaffolds supported cell proliferation, indicated by an increase in AlamarBlue® fluorescence reading from day 1 through day 7. Of note, there was no difference in cell proliferation between APS-co-PEG/PCL scaffolds and APS/PCL scaffolds on day 1 and day 3. However, on day 7, there was a higher metabolic activity for cells seeded on APS-25PEG/PCL scaffolds than all other scaffolds ($p<0.05$, Two-way ANOVA). All other APS-co-PEG/PCL scaffolds had similar cell viabilities to that of APS/PCL scaffold, consistent with the notion that they all support cell proliferation. These results indicate that APS-co-PEG/PCL scaffolds are biocompatible and can be explored further for soft tissue engineering.

Figure 28:
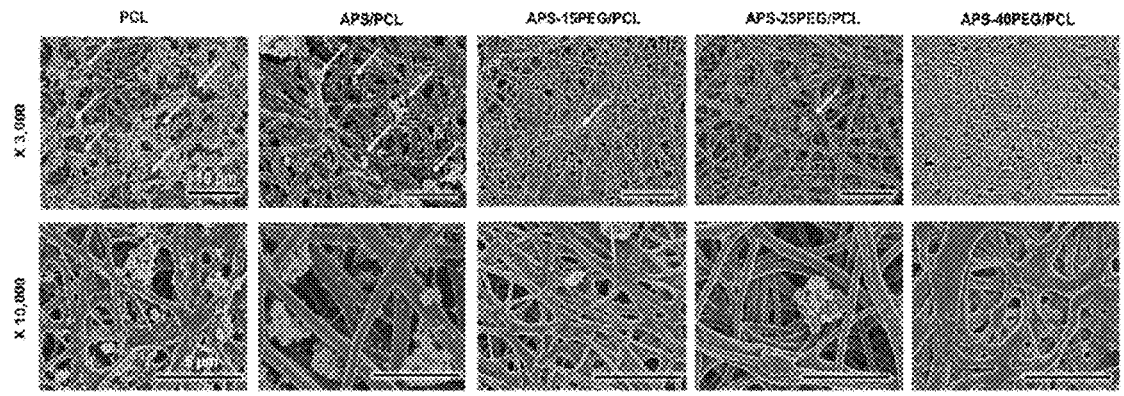
FIG. 28 SEM images of platelet adhesion assay at ×3,000 and ×10,000 magnification. Arrows indicate platelet adhesion. Scale bars in top row represent 10 µm. Scale bars in bottom row represent 5 µm.

Potential of APS-Co-PCL Scaffolds for Heart Valve Tissue Engineering:

Current heart valve substitutes such as mechanical valves have thrombogenicity issues or suffer from poor mechanical compliance, which results in the biomechanical mismatch between the device and the tissue, ultimately leading to the device failure (Korossis S A, et al. Tissue engineering of cardiac valve prostheses II: biomechanical characterization of decellularized porcine aortic heart valves. The Journal of heart valve disease. 2002; 11(4):463-71). Tissue engineered heart valve substitutes with tailored mechanical properties offer important alternative therapeutic strategy for patients with valvular heart disease. Tissue engineered heart valves can be designed from biodegradable polymers functionalized to reduce the thrombogenicity observed with mechanical valve substitutes. It has been shown that the presence of a PEG moiety can markedly decrease the thrombogenicity of polymeric materials (Karrer L, et al. PPS-PEG surface coating to reduce thrombogenicity of small diameter ePTFE vascular grafts. Int J Artif Organs. 2005; 28(10):993-1002 and Shih M F, et al. Synthesis and Evaluation of Poly (hexamethyleneurethane) and PEG-Poly(hexamethyleneurethane) and Their Cholesteryl Oleyl Carbonate Composites for Human Blood Biocompatibility. Molecules. 2011; 16(12):8181-97). PEGylated elastomers offer excellent opportunities for heart valve TE where high mechanical compliance of the elastomers can sustain dynamic mechanical environment present in the native valve tissue. Furthermore, presence of PEG in the elastomer backbone can mitigate the thrombogenicity observed for currently available heart valve substitutes. To test the hypothesis that PEGylation results in less thromobogenicity, control PCL, APS/PCL and PEGylated APS/PCL (APS-15PEG/PCL, APS-25PEG/PCL and APS-40PEG/PCL) scaffolds were exposed to PRP and investigated their ability to resist platelet adhesion. All APSco-PEG/PCL scaffolds displayed lower platelet adhesion than PCL and APS/PCL scaffolds as qualitatively assessed from SEM images (FIG. 28). Furthermore, the morphology of adhered platelets was evaluated by Cooper's classification of platelet adsorption (Shih M F, et al. *Molecules*. 2011; 16(12):8181-97 and Ko T M, et al. Surface characterization and platelet adhesion studies of plasmasulphonated polyethylene. Biomaterials. 1993; 14(9): 657-64). In PCL and APS/PCL groups, adhered platelets exhibited spreading and dendritic morphology, which represent late stage of platelet activation. On the other hand, platelets in APS-PEG/PCL groups exhibited round morphology with no pseudopodia. Overall, these results indicate the better haemocompatibility of PEGylated APS-co-PEG/PCL scaffolds.

Figure 29A:
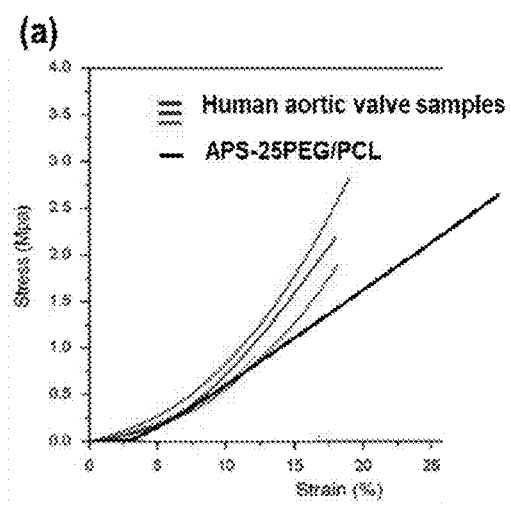
FIGS. 29A and 29B Mechanical and biological properties of electrospun APS-co-PEG/PCL scaffolds applicable to heart valve tissue engineering. (a) Overlay of the stress-strain curve of APS-25PEG/PCL with those from different human aortic valves. (b) Stress-strain curve of APS-25PEG/PCL scaffold during 10 cycles of tensile loading; (c) Spreading and morphology of human aortic valve cells seeded on APS-25PEG/PCL scaffold at 4 days after seeding. Actin cytoskeleton was stained with actinGreen (green); α-SMA was stained with anti-smooth muscle actin (red) and nuclei stained with NucBlue® (blue).
Figure 29B:
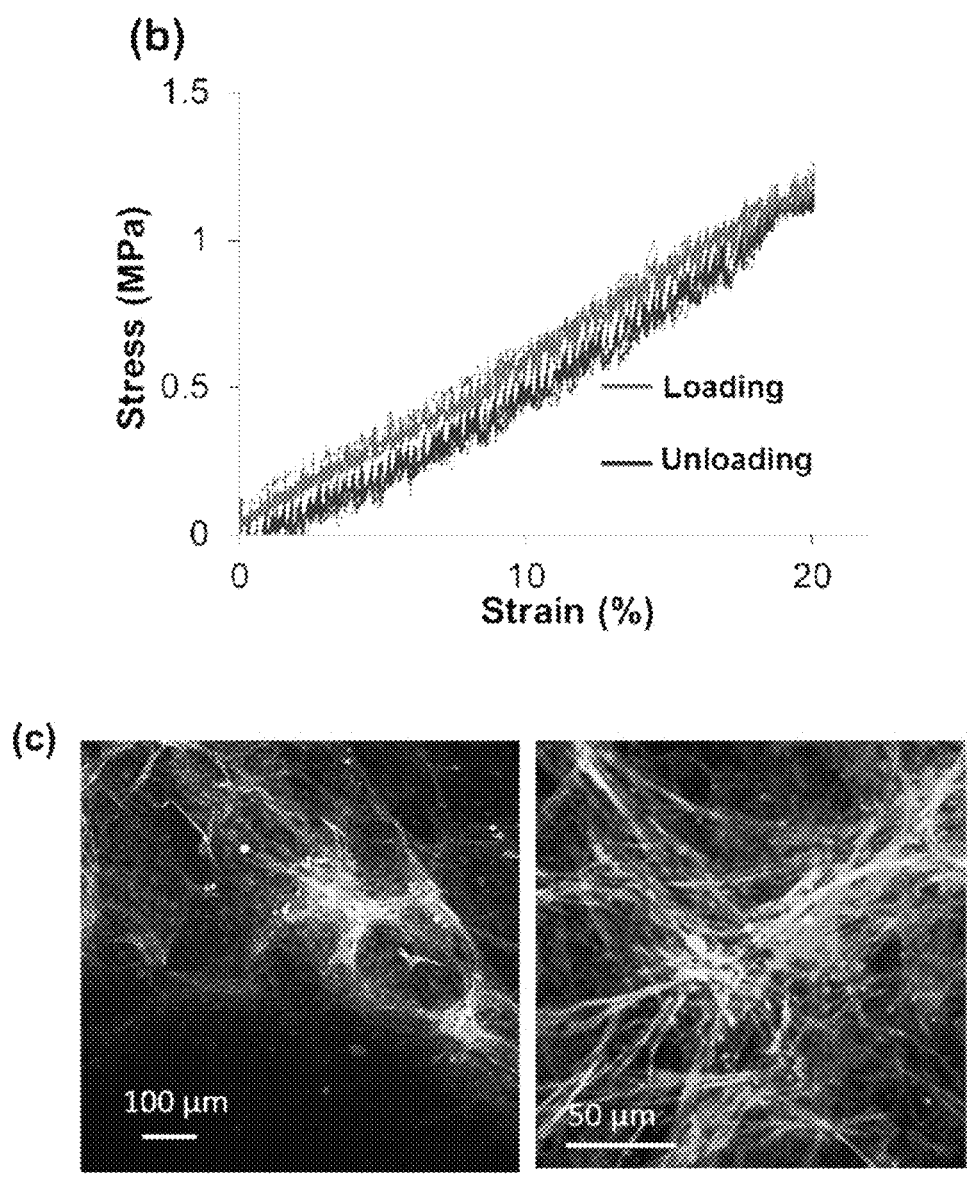

Another advantage of PEGylated elastomers as material for heart valve engineering is their elastomeric properties, which can maintain the scaffold integrity in dynamic mechanical environment in cardiovascular system. Mechanically analogous scaffolds have shown beneficial effect in maintaining the structural integrity of the scaffold in dynamic in vivo setting and guiding cell proliferation and tissue regeneration. Hence, we compared the uniaxial mechanical properties of APS-co-PEG scaffolds with that of the native valve tissue (e.g., Hasan A, et al. Biomechanical properties of native and tissue engineered heart valve constructs. Journal of Biomechanics. 2014; 47(9):1949-63). Cyclic Mechanical properties and cell attachment/spreading also were investigated as initial assessment of suitability of APS-co-PEG scaffolds for potential heart valve TE application. Comparing the APS-co-PEG/PCL scaffold properties to those of human heart valves, it was observed that the stress-strain curves of APS-25PEG/PCL overlap closely with that of human aortic valve tissues (FIG. 29A (a)). In fact, both, the scaffolds and the heart valves exhibit initial flat region in the curve, where the material undergoes strain but experiences very little stress (0-5% strain). It was also observed that APS-co-PEG/PCL scaffolds are more elastic (lower stiffness) than human heart valves, which may add the benefit of reduced chance of rupture and tearing. The resilience of APS-25PEG/PCL scaffold was further investigated by cyclic tensile tests. It was observed that APS-25PEG/PCL scaffolds could withstand 10 cycles of loading and unloading with minimal energy loss during the process (FIG. 29B (b)). This is especially important for heart valve TE application because the implanted scaffold should withstand the dynamic mechanical environment in vivo, ideally over the lifespan of the patient. As a proof of concept, human aortic valve cells were cultured on APS-25PEG/PCL scaffolds for 4 days. It was found that human valve cells could attach and spread on APS-25PEG/PCL scaffolds and express the valve interstitial cell marker α-SMA (FIG. 29B (c)). Taken together, APS-25PEG/PCL scaffolds has potential in heart valve tissue engineering, and further detailed studies are underway to investigate cellular behaviors of human valve interstitial cells seeded on these scaffolds.

Non-limiting, various aspects of the invention are described in the following clauses:

1. A polymer composition comprising a copolymer comprising residues of a poly ($C_2$-$C_4$)alkylene glycol, an aliphatic $C_3$-$C_7$ polyol with at least 3 hydroxyl groups, and 1,3-diamino-2-hydroxy-propane.
2. The polymer composition of clause 1, wherein the aliphatic $C_3$-$C_7$ polyol with at least 3 hydroxyl groups is glycerol.
3. The polymer composition of clause 1, wherein the poly ($C_2$-$C_4$)alkylene glycol is a polyethylene glycol.
4. The polymer composition of any one of clauses 1-3, wherein the poly ($C_2$-$C_4$)alkylene glycol has a $M_n$ of from 200 D (Daltons) to 10 kD (kiloDaltons).
5. The polymer composition of any one of clauses 1-3, wherein the poly (C2-C4)alkylene glycol has a $M_n$ of from 400 D to 4 kD.
6. The polymer composition of any one of clauses 1-5 wherein the dicarboxylic acid is sebacic acid.
7. The polymer composition of any one of clauses 1-6 wherein the molar feed percentage of the poly ($C_2$-$C_4$) alkylene glycol to the dicarboxylic acid ranges from 10% to 50%, or from 15% to 40%.
8. The polymer composition of clause 1, wherein the poly ($C_2$-$C_4$)alkylene glycol is polyethylene glycol having a Mn of from 400 D to 4 kD, the aliphatic $C_3$-$C_7$ polyol with at least 3 hydroxyl groups is glycerol, the dicarboxylic acid is sebacic acid, and the feed percentage of polyethylene glycol to sebacic acid ranges from 1% to 60%, and optionally from 15% to 40%.
9. The polymer composition of clause 1, having a $M_n$ of from 3 kD to 10 kD and/or a polydispersity index of less than 2.
10. The polymer composition of any one of clauses 1-9, further comprising an active agent.
11. The polymer composition of clause 10, wherein the active agent is an antioxidant.
12. The polymer composition of clause 11, wherein the active agent is a cerium nanoparticle.
13. A method of preparing a biocompatible elastomer copolymer, comprising:
   a. condensing in a reaction mixture a $C_8$-$C_{12}$ aliphatic dicarboxylic acid (e.g., —C(O)—$(CH_2)_{6-10}$—C(O)—) with a poly($C_2$-$C_4$ alkylene glycol) to produce a first product; and
   b. adding an aliphatic C3-$C_7$ polyol with at least 3 hydroxyl groups and 1,3-diamino-2-hydroxy-propane to the reaction mixture and condensing the first product with the glycerol and 1,3-diamino-2-hydroxy-propane (DAHP) to produce the elastomer.
14. The method of clause 13, wherein the feed molar ratio of the C8-$C_{12}$ aliphatic dicarboxylic acid ranges between 90% and 110% of the sum of the feed molar ratios of the poly($C_2$-$C_4$ alkylene glycol), the an aliphatic $C_3$-$C_7$ polyol with at least 3 hydroxyl groups and the DAHP in the reaction mixture.
15. The method of any one of clauses 13 and 14, wherein the feed molar ratio of the poly($C_2$-$C_4$ alkylene glycol) is between 15% and 40% of the feed molar ratio of the C8-$C_{12}$ aliphatic dicarboxylic acid.

16. The method of any one of clauses 13-15, wherein the molar ratio of the DAHP is between 1- and 3-times the molar ratio of the aliphatic $C_3$-$C_7$ polyol with at least 3 hydroxyl groups.
17. The method of clause 13, wherein the molar ratio of the DAHP is, is about, or is approximately twice the molar ratio of the an aliphatic $C_3$-$C_7$ polyol with at least 3 hydroxyl groups.
18. The method of any one of clauses 13-17, wherein the poly($C_2$-$C_4$ alkylene glycol) is poly(ethylene glycol) (PEG).
19. The method of any one of clauses 13-18, wherein the aliphatic $C_3$-$C_7$ polyol with at least 3 hydroxyl groups is glycerol.
20. The method of any one of clauses 13-19, wherein the $C_8$-$C_{12}$ aliphatic dicarboxylic acid is sebacic acid.
21. The method of clause 13, wherein the poly($C_2$-$C_4$ alkylene glycol) is poly(ethylene glycol), the aliphatic $C_3$-$C_7$ polyol with at least 3 hydroxyl groups is glycerol, the $C_8$-$C_{12}$ aliphatic dicarboxylic acid is sebacic acid, and the feed ratios of sebacic acid:glycerol:DAHP:PEG are (2.5-3.5):(0.5 to 1.2):(1.2 to 1.7):(0.45 to 1.26), where the sum of the feed ratios of the glycerol, DAHP and PEG is, is approximately, or is about 3, or is 3+/−0.3, e.g., the feed ratios of sebacic acid:glycerol:DAHP:PEG are selected from 3:0.85:1.7:0.45, 3:0.75:1.5:0.75, and 3:0.6:1.2:1.2.
22. The method of any one of clauses 13-21, wherein the poly(C2-C4 alkylene glycol) has a Mn of from 200 D to 10 kD, from 250 D to 5 kD, from 400 D to 4 kD, or 400 D, 1 kD, 2 kD and 4 kD.
23. The method of any one of clauses 13-22, wherein the condensation is performed by heating the reaction mixture in an inert atmosphere, e.g. argon, optionally under reduced (less than atmospheric, e.g., less than 0.001 atm (atmosphere), e.g., 300 mTorr) pressure.
24. A method of culturing cells, comprising placing a composition of any of clauses 1-12 in a suitable cell growth medium; contacting cells with the composition; and culturing cells under conditions suitable for cell growth.
25. A method of determining either the crosslinking density or relative quantities of amide or ester bonds in a polymer composition comprising one or both of amide and ester bonds, comprising preparing the polymer composition, performing a semiquantitative FTIR assay on a sample of the polymer composition that determines carbonyl bond and amide bond peaks and optionally a pre-polymer or pre-crosslinking sample of the polymer, calculating a ratio of amide bonds to carbonyl bonds in the sample based on the semiquantitative FTIR assay, producing an output based on the semiquantitative FTIR assay, wherein the calculating and producing an output step are optionally computer-implemented, and the output is optionally stored on a non-transitory data medium.
26. A tissue prosthesis comprising the polymer composition of any one of clauses 1-12.
27. The tissue prosthesis of clause 26, comprising at least a heart valve leaflet with anisotropic fiber orientation.

While the present invention is described with reference to several distinct embodiments, those skilled in the art may make modifications and alterations without departing from the scope and spirit. Accordingly, the above detailed description is intended to be illustrative rather than restrictive.

---

We claim:

1. A polymer composition comprising a copolymer comprising residues of polyethylene glycol, glycerol, sebacic acid, and 1,3-diamino-2-hydroxy-propane, wherein the feed ratios of sebacic acid:glycerol:DAHP:PEG are (2.5-3.5):(0.5 to 1.2):(1.2 to 1.7):(0.45 to 1.26).

2. The polymer composition of claim 1, wherein the polyethylene glycol has a $M_n$ of from 200D (Daltons) to 10 kD (kiloDaltons).

3. The polymer composition claim 1, wherein the molar feed percentage of the polyethylene glycol to the sebacic acid ranges from 15% to 40%.

4. The polymer composition of claim 1, wherein the polyethylene glycol has a Mn of from 400D to 4 kD, and the feed percentage of polyethylene glycol to sebacic acid ranges from 15% to 40%.

5. The polymer composition of claim 1, having a Mn of from 3 kD to 10 kD and/or a polydispersity index of less than 2.

6. The polymer composition of claim 1, further comprising an active agent.

7. The polymer composition of claim 6, wherein the active agent is an antioxidant.

8. The polymer composition of claim 7, wherein the active agent is a cerium nanoparticle.

9. A method of preparing a biocompatible elastomer copolymer, comprising:

a. condensing in a reaction mixture a sebacic acid with a polyethylene glycol to produce a first product; and b. adding glycerol and 1,3-diamino-2-hydroxy-propane to the reaction mixture and condensing the first product with the glycerol and 1,3-diamino-2-hydroxy-propane (DAHP) to produce the elastomer copolymer, wherein the feed ratios of sebacic acid:glycerol:DAHP:PEG are (2.5-3.5):(0.5 to 1.2):(1.2 to 1.7):(0.45 to 1.26).

10. The method of claim 9, wherein the feed molar ratio of the sebacic acid ranges between 90% and 110% of the sum of the feed molar ratios of the polyethylene glycol, the glycerol, and the DAHP in the reaction mixture.

11. The method of claim 9, wherein the feed molar ratio of the polyethylene glycol is between 15% and 40% of the feed molar ratio of the sebacic acid.

12. The method of claim 9, wherein the molar ratio of the DAHP is between 1- and 3-times the molar ratio of the glycerol.

13. The method of claim 9, wherein the polyethylene glycol has a Mn of from 200D to 10 kD.

14. The method of claim 9, wherein the condensation is performed by heating the reaction mixture in an inert atmosphere, e.g. argon, optionally under reduced (less than atmospheric, e.g., less than 0.001 atm (atmosphere), e.g., 300 mTorr) pressure.

15. A method of culturing cells, comprising placing a composition of claim 1 in a suitable cell growth medium; contacting cells with the composition;

and culturing cells under conditions suitable for cell growth.

16. A tissue prosthesis comprising the polymer composition of claim 1.

17. The tissue prosthesis of claim 16, comprising at least a heart valve leaflet with anisotropic fiber orientation.

18. The polymer composition of claim 1, wherein the feed ratio of sebacic acid:glycerol:DAHP:PEG is 3:0.85:1.7:0.45.

19. The polymer composition of claim 1, wherein the feed ratio of sebacic acid:glycerol:DAHP:PEG is 3:0.75:1.5:0.75.

20. The polymer composition of claim 1, wherein the feed ratio of sebacic acid:glycerol:DAHP:PEG is 3:0.6:1.2:1.2.

* * * * *

UNITED STATES PATENT AND TRADEMARK OFFICE
CERTIFICATE OF CORRECTION

PATENT NO. : 10,039,858 B2
APPLICATION NO. : 15/227187
DATED : August 7, 2018
INVENTOR(S) : Shilpa Sant et al.

Page 1 of 1

It is certified that error appears in the above-identified patent and that said Letters Patent is hereby corrected as shown below:

On the Title Page

Item (73) Line 2, delete "Commonweatlh" and insert -- Commonwealth --

In the Claims

Column 53, Line 50, Claim 3, after "composition" insert -- of --

Signed and Sealed this
Twentieth Day of November, 2018

Andrei Iancu
*Director of the United States Patent and Trademark Office*